(12) United States Patent
Wong et al.

(10) Patent No.: US 12,336,988 B2
(45) Date of Patent: Jun. 24, 2025

(54) **THERAPEUTIC TARGETING OF *KMT2D* MUTANT LUNG SQUAMOUS CELL CARCINOMA THROUGH RTK-RAS SIGNALING INHIBITION**

(71) Applicant: New York University, New York, NY (US)

(72) Inventors: Kwok-Kin Wong, Arlington, MA (US); Yuanwang Pan, New York, NY (US); Han Han, New York, NY (US); Hua Zhang, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 17/935,915

(22) Filed: Sep. 27, 2022

(65) Prior Publication Data

US 2023/0102398 A1 Mar. 30, 2023

Related U.S. Application Data

(60) Provisional application No. 63/248,772, filed on Sep. 27, 2021.

(51) Int. Cl.
*A61K 31/497* (2006.01)
*A61K 31/517* (2006.01)
*C12Q 1/6886* (2018.01)

(52) U.S. Cl.
CPC .......... *A61K 31/497* (2013.01); *A61K 31/517* (2013.01); *C12Q 1/6886* (2013.01); *C12Q 2600/112* (2013.01)

(58) Field of Classification Search
CPC .. A61K 31/497; A61K 31/517; C12Q 1/6886; C12Q 2600/112
See application file for complete search history.

(56) References Cited

U.S. PATENT DOCUMENTS

2017/0175197 A1* 6/2017 Gatalica .......... G01N 33/57492

FOREIGN PATENT DOCUMENTS

WO    WO-2021018287 A1 *  2/2021  ............. A61P 35/00

OTHER PUBLICATIONS

Zhao et al., Combinations with Allosteric SHP2 Inhibitor TNO155 to Block Receptor Tyrosine Kinase Signaling, Clin. Cancer Res., 27, pp. 342-354 (Year: 2021).*
Liu et al., SHP2 inhibition triggers anti-tumor immunity and synergizes with PD-1 blockade, Acta. Pharm Sin. B, 9, pp. 304-315 (Year: 2019).*
Liu et al., Combinations with Allosteric SHP2 Inhibitor TNO155 to Block Receptor Tyrosine Kinase Signaling, Clin. Cancer Res., 27, pp. 342-354 (Year: 2021).*

(Continued)

*Primary Examiner* — Jeffrey S Lundgren
*Assistant Examiner* — Alexander K. Showalter
(74) *Attorney, Agent, or Firm* — Hodgson Russ LLP

(57) ABSTRACT

Provided is a method for treatment of lung squamous cell carcinoma (LUSC) by administering to an individual in need of treatment one or more inhibitors of the RTK-Ras signaling pathway. The LUSC cells may carry a mutation in a KMT2D gene. The inhibitors of the RTK-Ras signaling pathway are SHP2 inhibitors or epidermal growth factor receptor (EGFR) inhibitors. Combinations of the SHP2 inhibitors and EGFR inhibitors can be used.

3 Claims, 44 Drawing Sheets
(44 of 44 Drawing Sheet(s) Filed in Color)
Specification includes a Sequence Listing.

(56) References Cited

OTHER PUBLICATIONS

Shi et al., Discovery of a novel competitive inhibitor of PTP1B by high-throughput screening, Acta. Pharmcol. Sin., 29, pp. 278-284 (Year: 2008).*
Soria et al., Afatinib versus erlotinib as second-line treatment of patients with advanced squamous cell carcinoma of the lung (LUX-Lung 8): an open-label randomised controlled phase 3 trial, Lancet Oncol., 16, pp. 897-907 (Year: 2015).*
Tsiani et al., Vanadium Compounds Biological Actions and Potential as Pharmacological Agents, Trends in Endocrinology & Metabolism, 8, pp. 51-58 (Year: 1997).*
WO2021/018287 to Zheng (machine translation) (Year: 2021).*
Alam et al., KMT2D Deficiency Impairs Super-Enhancers to Confer a Glycolytic Vulnerability in Lung Cancer, Cancer Cell, 37, pp. 599-617 (Year: 2020).*
Pan et al., UBE2D3 Activates SHP-2 Ubiquitination to Promote Glycolysis and Proliferation of Glioma via Regulating STAT3 Signaling Pathway, Front. Oncol., 11, (Year: 2021).*
Soria et al., Afatinib versus erlotinib as second-line treatment of patients with advanced squamous cell carcinoma of the lung (LUX-Lung 8): an open-label randomized controlled phase 3 trial, Lancet Oncol., 16, pp. 897-907 (Year: 2015).*
Zheng et al., machine translation of WO2021018287 (Year: 2021).*

* cited by examiner

H

I

A

B

K

L

```
                          SEQUENCE LISTING

Sequence total quantity: 37
SEQ ID NO: 1            moltype = DNA  length = 22
FEATURE                 Location/Qualifiers
source                  1..22
                        mol_type = other DNA
                        organism = synthetic construct
SEQUENCE: 1
atcctcgtcc tgaccatcag tg                                               22

SEQ ID NO: 2            moltype = DNA  length = 22
FEATURE                 Location/Qualifiers
source                  1..22
                        mol_type = other DNA
                        organism = synthetic construct
SEQUENCE: 2
gctccaggtt accatcagcc ta                                               22

SEQ ID NO: 3            moltype = DNA  length = 22
FEATURE                 Location/Qualifiers
source                  1..22
                        mol_type = other DNA
                        organism = synthetic construct
SEQUENCE: 3
cagattcgtg gctaccaggt ca                                               22

SEQ ID NO: 4            moltype = DNA  length = 22
FEATURE                 Location/Qualifiers
source                  1..22
                        mol_type = other DNA
                        organism = synthetic construct
SEQUENCE: 4
acggtgatgg agtaggtggt ct                                               22

SEQ ID NO: 5            moltype = DNA  length = 22
FEATURE                 Location/Qualifiers
source                  1..22
                        mol_type = other DNA
                        organism = synthetic construct
SEQUENCE: 5
taccaggtcc actatgtgcg ca                                               22

SEQ ID NO: 6            moltype = DNA  length = 22
FEATURE                 Location/Qualifiers
source                  1..22
                        mol_type = other DNA
                        organism = synthetic construct
SEQUENCE: 6
agtctcaggc tggaggttcg tt                                               22

SEQ ID NO: 7            moltype = DNA  length = 22
FEATURE                 Location/Qualifiers
source                  1..22
                        mol_type = other DNA
                        organism = synthetic construct
SEQUENCE: 7
gaactgcatc cgaattgcca gg                                               22

SEQ ID NO: 8            moltype = DNA  length = 22
FEATURE                 Location/Qualifiers
source                  1..22
                        mol_type = other DNA
                        organism = synthetic construct
SEQUENCE: 8
aatgaggacg gcaagaccac ct                                               22

SEQ ID NO: 9            moltype = DNA  length = 23
FEATURE                 Location/Qualifiers
```

```
source                  1..23
                        mol_type = other DNA
                        organism = synthetic construct
SEQUENCE: 9
cattgctgac aggatgcaga agg                                        23

SEQ ID NO: 10           moltype = DNA   length = 22
FEATURE                 Location/Qualifiers
source                  1..22
                        mol_type = other DNA
                        organism = synthetic construct
SEQUENCE: 10
tgctggaagg tggacagtga gg                                         22

SEQ ID NO: 11           moltype = DNA   length = 22
FEATURE                 Location/Qualifiers
source                  1..22
                        mol_type = other DNA
                        organism = synthetic construct
SEQUENCE: 11
tcttcccgac aagtggttgt gg                                         22

SEQ ID NO: 12           moltype = DNA   length = 22
FEATURE                 Location/Qualifiers
source                  1..22
                        mol_type = other DNA
                        organism = synthetic construct
SEQUENCE: 12
agccaggaaa cgctgaggta gt                                         22

SEQ ID NO: 13           moltype = DNA   length = 22
FEATURE                 Location/Qualifiers
source                  1..22
                        mol_type = other DNA
                        organism = synthetic construct
SEQUENCE: 13
atgtcatcgc ctacgaccac tc                                         22

SEQ ID NO: 14           moltype = DNA   length = 22
FEATURE                 Location/Qualifiers
source                  1..22
                        mol_type = other DNA
                        organism = synthetic construct
SEQUENCE: 14
gtggcgatgt aggcattctg ct                                         22

SEQ ID NO: 15           moltype = DNA   length = 22
FEATURE                 Location/Qualifiers
source                  1..22
                        mol_type = other DNA
                        organism = synthetic construct
SEQUENCE: 15
ctcgcccaag aacttcaagg tg                                         22

SEQ ID NO: 16           moltype = DNA   length = 22
FEATURE                 Location/Qualifiers
source                  1..22
                        mol_type = other DNA
                        organism = synthetic construct
SEQUENCE: 16
aggtgcgtga tgagcttctt gg                                         22

SEQ ID NO: 17           moltype = DNA   length = 22
FEATURE                 Location/Qualifiers
source                  1..22
                        mol_type = other DNA
                        organism = synthetic construct
SEQUENCE: 17
acaaccagac ctaccgaggc tt                                         22

SEQ ID NO: 18           moltype = DNA   length = 22
FEATURE                 Location/Qualifiers
source                  1..22
                        mol_type = other DNA
                        organism = synthetic construct
SEQUENCE: 18
ctttcctggc aatgcggatg ca                                         22

SEQ ID NO: 19           moltype = DNA   length = 22
```

```
FEATURE                 Location/Qualifiers
source                  1..22
                        mol_type = other DNA
                        organism = synthetic construct
SEQUENCE: 19
caccattggc aatgagcggt tc                                              22

SEQ ID NO: 20           moltype = DNA   length = 22
FEATURE                 Location/Qualifiers
source                  1..22
                        mol_type = other DNA
                        organism = synthetic construct
SEQUENCE: 20
aggtctttgc ggatgtccac gt                                              22

SEQ ID NO: 21           moltype = RNA   length = 20
FEATURE                 Location/Qualifiers
source                  1..20
                        mol_type = other RNA
                        organism = Mus musculus
SEQUENCE: 21
gaggtctccg tccccggttc                                                 20

SEQ ID NO: 22           moltype = RNA   length = 20
FEATURE                 Location/Qualifiers
source                  1..20
                        mol_type = other RNA
                        organism = Mus musculus
SEQUENCE: 22
cagagagcac aacgccgtgc                                                 20

SEQ ID NO: 23           moltype = RNA   length = 20
FEATURE                 Location/Qualifiers
source                  1..20
                        mol_type = other RNA
                        organism = Mus musculus
SEQUENCE: 23
gctaacgatc tctttgatga                                                 20

SEQ ID NO: 24           moltype = RNA   length = 20
FEATURE                 Location/Qualifiers
source                  1..20
                        mol_type = other RNA
                        organism = Homo sapiens
SEQUENCE: 24
aaccgacgga gggcgtagtg                                                 20

SEQ ID NO: 25           moltype = RNA   length = 20
FEATURE                 Location/Qualifiers
source                  1..20
                        mol_type = other RNA
                        organism = Homo sapiens
SEQUENCE: 25
ggggataggc gcgataccte                                                 20

SEQ ID NO: 26           moltype = DNA   length = 20
FEATURE                 Location/Qualifiers
source                  1..20
                        mol_type = other DNA
                        organism = Mus musculus
SEQUENCE: 26
ccgcctgctg aagataaaga                                                 20

SEQ ID NO: 27           moltype = DNA   length = 22
FEATURE                 Location/Qualifiers
source                  1..22
                        mol_type = other DNA
                        organism = Mus musculus
SEQUENCE: 27
ggtgggatga gataaacaga gg                                              22

SEQ ID NO: 28           moltype = DNA   length = 23
FEATURE                 Location/Qualifiers
source                  1..23
                        mol_type = other DNA
                        organism = Mus musculus
SEQUENCE: 28
aaatcctggc tttgtctgaa atg                                             23
```

```
SEQ ID NO: 29            moltype = DNA  length = 21
FEATURE                  Location/Qualifiers
source                   1..21
                         mol_type = other DNA
                         organism = Mus musculus
SEQUENCE: 29
ggttaacact gtgaccggta g                                                   21

SEQ ID NO: 30            moltype = DNA  length = 18
FEATURE                  Location/Qualifiers
source                   1..18
                         mol_type = other DNA
                         organism = Homo sapiens
SEQUENCE: 30
ggagtctcct ctgtctcc                                                       18

SEQ ID NO: 31            moltype = DNA  length = 19
FEATURE                  Location/Qualifiers
source                   1..19
                         mol_type = other DNA
                         organism = Homo sapiens
SEQUENCE: 31
gtgtgattcc tcaggttgg                                                      19

SEQ ID NO: 32            moltype = DNA  length = 18
FEATURE                  Location/Qualifiers
source                   1..18
                         mol_type = other DNA
                         organism = Homo sapiens
SEQUENCE: 32
tctccaccgg aagagtca                                                       18

SEQ ID NO: 33            moltype = DNA  length = 19
FEATURE                  Location/Qualifiers
source                   1..19
                         mol_type = other DNA
                         organism = Homo sapiens
SEQUENCE: 33
ggacaggtgc aattcctca                                                      19

SEQ ID NO: 34            moltype = DNA  length = 21
FEATURE                  Location/Qualifiers
source                   1..21
                         mol_type = other DNA
                         organism = Homo sapiens
SEQUENCE: 34
ctttaaggct gggtctctag c                                                   21

SEQ ID NO: 35            moltype = DNA  length = 22
FEATURE                  Location/Qualifiers
source                   1..22
                         mol_type = other DNA
                         organism = Homo sapiens
SEQUENCE: 35
gacaaggtag atgaaggtgg ag                                                  22

SEQ ID NO: 36            moltype = DNA  length = 19
FEATURE                  Location/Qualifiers
source                   1..19
                         mol_type = other DNA
                         organism = Homo sapiens
SEQUENCE: 36
gggtctctag cccacactt                                                      19

SEQ ID NO: 37            moltype = DNA  length = 22
FEATURE                  Location/Qualifiers
source                   1..22
                         mol_type = other DNA
                         organism = Homo sapiens
SEQUENCE: 37
ggtggagcaa ccttcaatat cc                                                  22
```

THERAPEUTIC TARGETING OF *KMT2D* MUTANT LUNG SQUAMOUS CELL CARCINOMA THROUGH RTK-RAS SIGNALING INHIBITION

CROSS REFERENCE TO RELATED APPLICATION

This application claims priority to U.S. provisional application No. 63/248,772, filed Sep. 27, 2021, the entire disclosure of which is incorporated herein by reference.

STATEMENT REGARDING FEDERALLY SPONSORED RESEARCH OR DEVELOPMENT

This invention was made with government support under grant nos. R01CA219670, R01CA205150, and P01CA154303 awarded by the National Institutes of Health. The government has certain rights in the invention.

SEQUENCE LISTING

The instant application contains a Sequence Listing which has been submitted in .xml format and is hereby incorporated by reference in its entirety. Said .xml copy was created on Sep. 27, 2022, is named "058636_00557_ST26.xml", and is 33,573 bytes in size.

BACKGROUND OF THE DISCLOSURE

Lung cancer remains the most commonly diagnosed malignancy and the leading cause of cancer death worldwide. Lung squamous cell carcinoma (LUSC) represents a major subtype of lung cancer with limited treatment options. Genomic analysis of LUSC patient tumors reveals numerous highly altered genes and pathways, but actionable driver mutations are rare. Several targeted therapies tested in LUSC patients have demonstrated very limited clinical benefits and no targeted therapies have been approved in the clinic. Due to the lack of established driver mutations, the development of LUSC preclinical models that recapitulate human LUSC genetics and pathology remains challenging. Therefore, exploring driver mutations as well as effective therapeutics represent an urgent unmet need for LUSC patients.

SUMMARY OF THE DISCLOSURE

The present disclosure demonstrates that KMT2D mutation is an oncogenic driver for LUSC, KMT2D loss activates RTK-Ras signaling, and KMT2D$^{-/-}$ cells are selectively sensitive to RTK-Ras signaling inhibition. Based at least in part on the data provided herein, in an aspect, this disclosure provides a method for identifying lung cancer patients that are suitable for treatment with SHP2 and or ERBB (also known as ErbB) inhibitors. The method comprises identifying the presence of KMT2D mutation in the lung tumor tissue of the patients, and may further comprise administering to an individual who has a KMT2D mutation tumor on or more therapeutic agents. In an aspect, this disclosure provides a method of treating KMT2D mutant LUSC, the method comprising administering to an individual in need of treatment one or more inhibitors of SHP2 (Src homology-2 domain-containing protein tyrosine phosphatase-2) and/or EGFR (epidermal growth factor receptor).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Heatmap of genes that were significantly upregulated (Log 2FC>1) in the "Kras signaling up" gene set in Kmt2d KO versus Kmt2d WT cells. (D) GSEA analysis of RNA-seq for KMT2D low versus KMT2D high LUSC tumors (TCGA LUSC dataset) indicated that Kras signaling pathway was significantly enriched. (E) Western blot of ERK, pERK and β-Actin in Kmt2d KO and Kmt2d WT cells and quantifications of pERK/ERK. Data shown as means±SEM. *$p<0.05$ (unpaired two-tailed t test). (F-H) Phospho-receptor tyrosine kinase arrays for Kmt2d KO and Kmt2d WT organoids (F), cell lines (G) and tumor nodules (H). pEGFR and pERBB2 are highlighted by the arrows. (I) Quantification pEGFR and pERBB2 in Kmt2d KO and the Kmt2d WT organoids, cell lines and tumor nodules. Data shown as means±SEM. *$p<0.05$, $p<0.01$, *$p<0.001$ (unpaired two-tailed t test). (J) Scatterplots showing significant and negative correlation of KMT2D mRNA level with phospho-EGFR expression in human TCGA LUSC dataset. r, Pearson's correlation coefficient. (K) Relative phospho-EGFR expression protein expression in KMT2D mutant LUSC tumors and their paired normal lung tissues from (Satpathy et al., 2021). Data shown as means±SEM. *$p<0.05$ (unpaired two-tailed t test).

Figure 4:
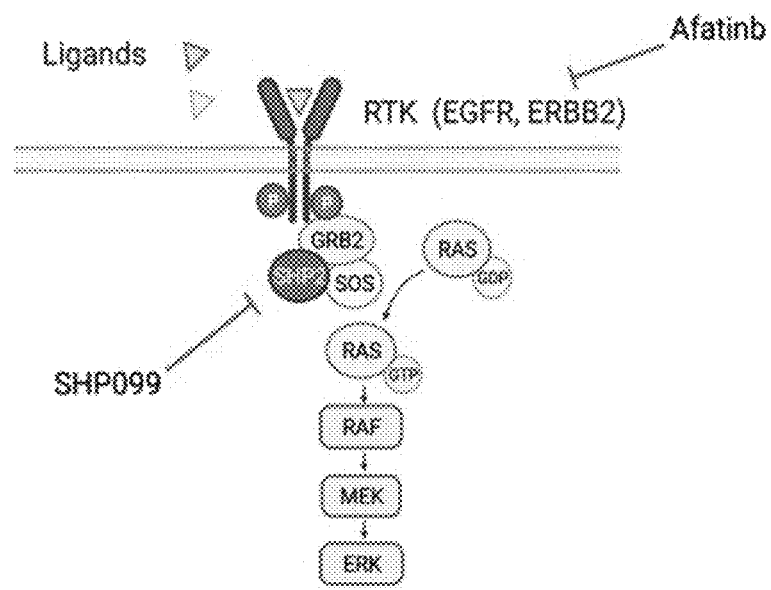
Figure 4:
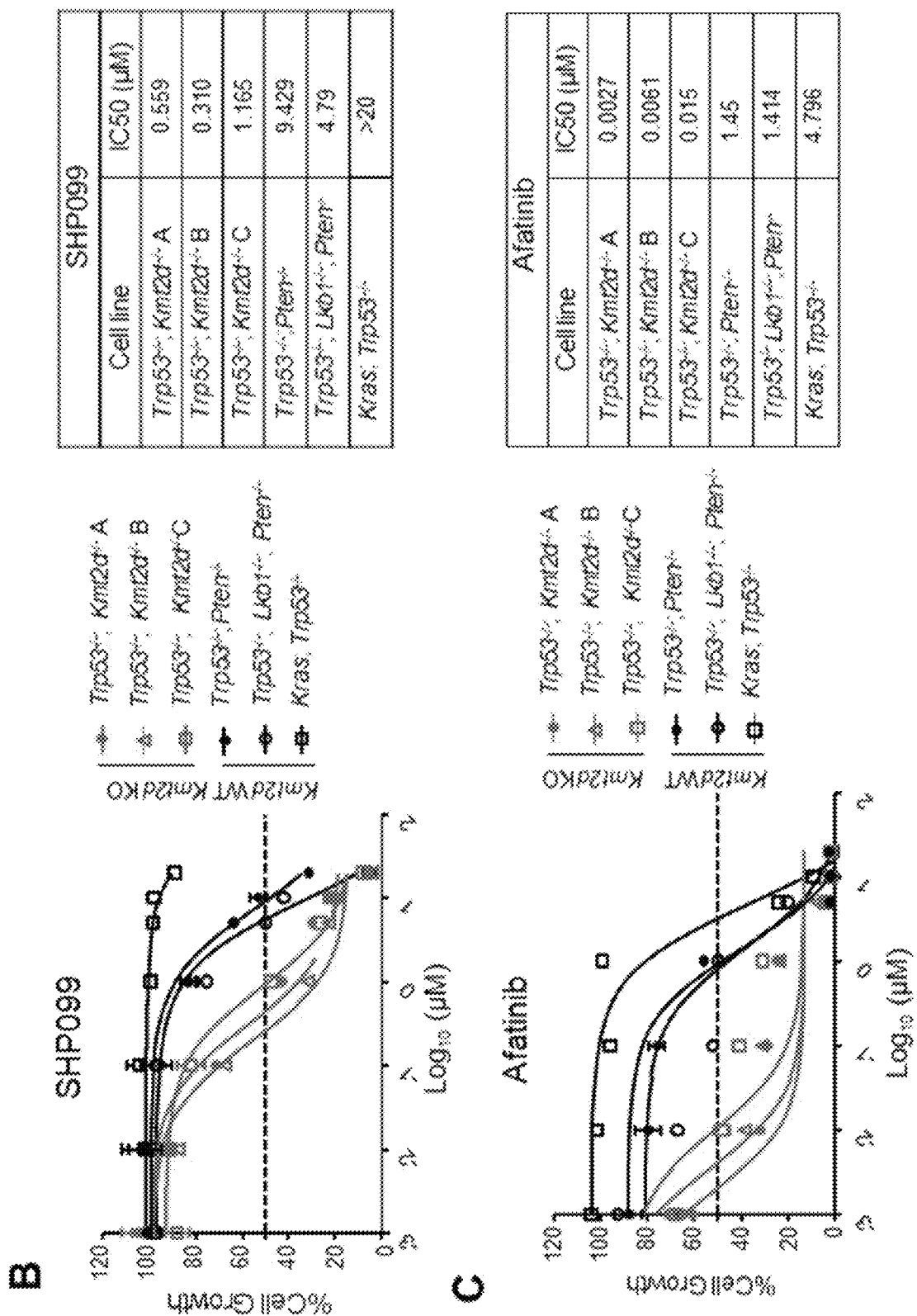
Figure 4:
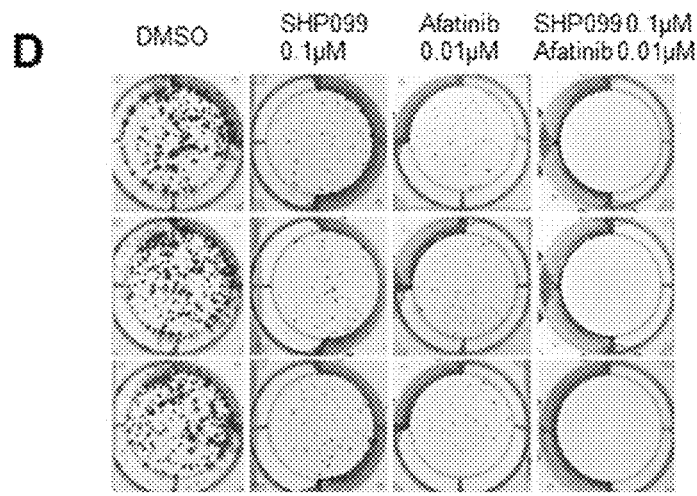
Figure 4:
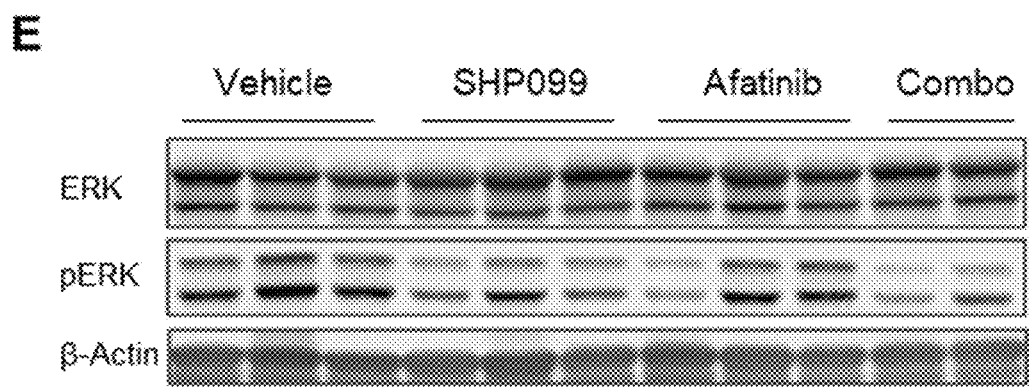
Figure 4:
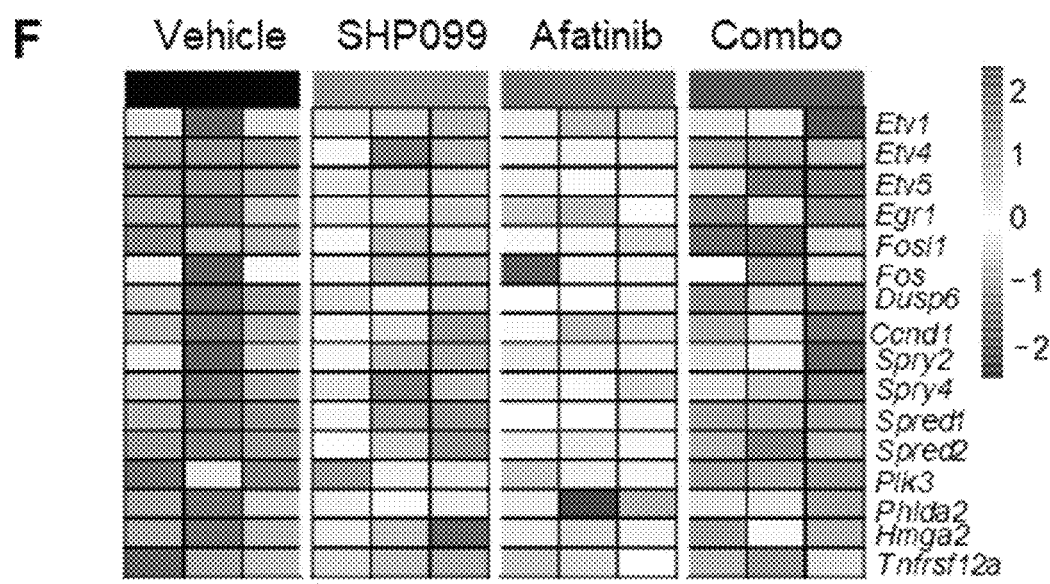
Figure 4:
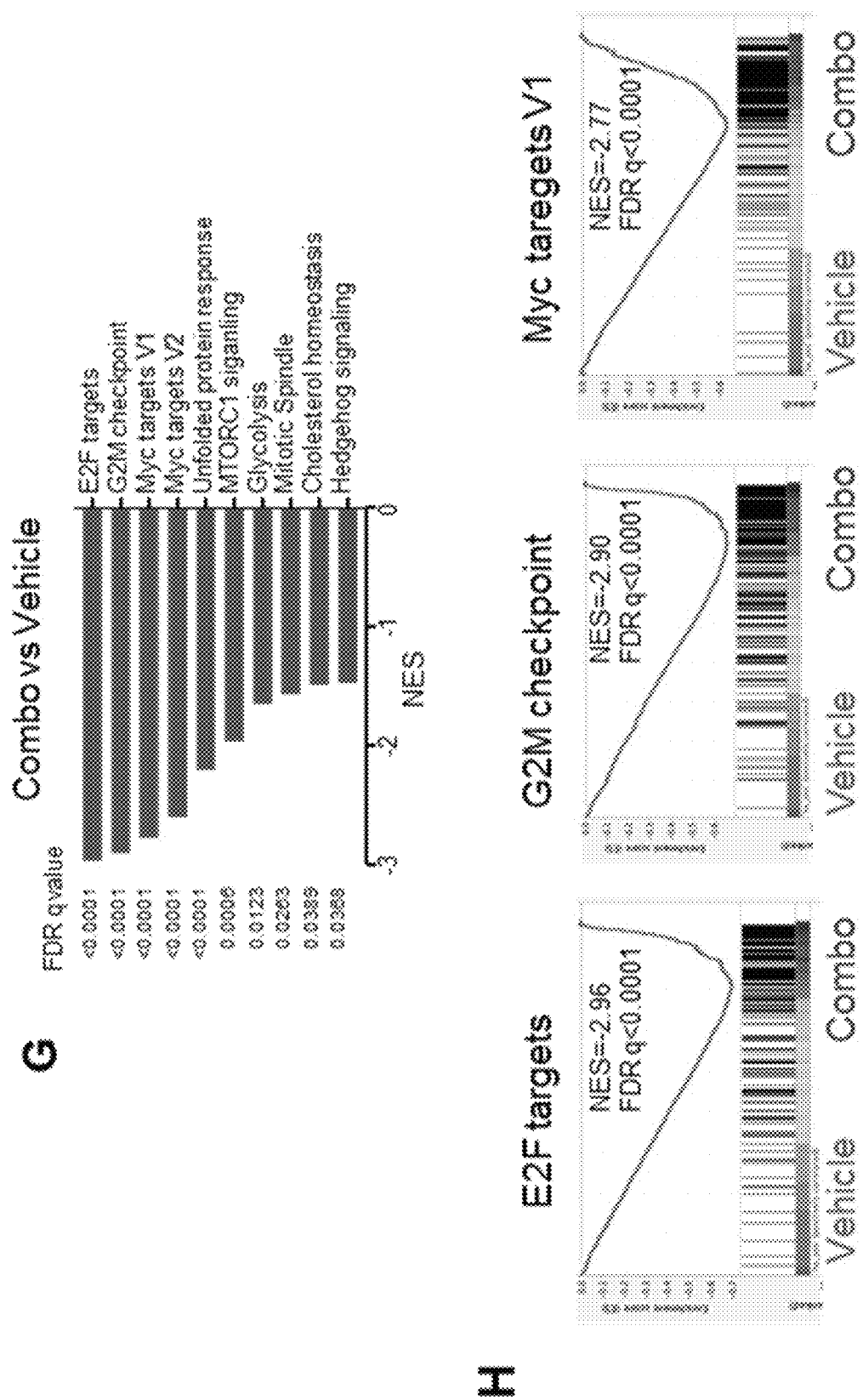
Figure 4:
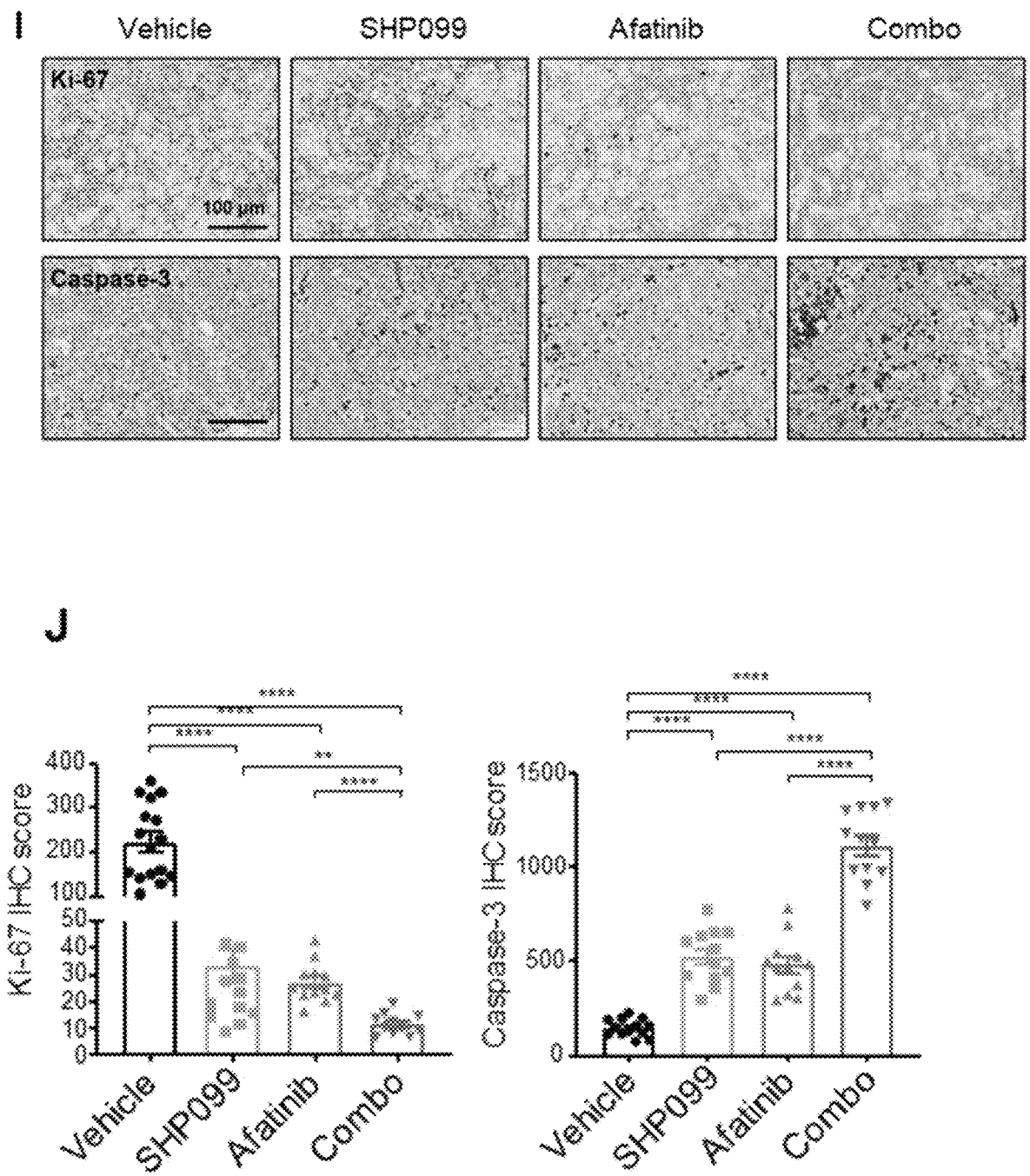

FIG. 4. KMT2D-deficient LUSC is hypersensitive to SHP2 and pan-ERBB inhibition. (A) Schematic illustration of targeting the RTK-Ras signaling through SHP2 inhibitor SHP099 and pan-ERBB inhibitor afatinib. (B and C) Cellular viability assays of Kmt2d KO LUSC cell lines, Kmt2d WT LUSC cell lines, and LUAD (KP) cell line treated with SHP099 (B) and afatinib (C) for 72 h. Data presented as mean±s.d. (n=3). The calculated IC50 values of SHP099 and afatinib are shown on the right. (D) Colony formation assay of Kmt2d KO cells treated with vehicle, SHP099, afatinib, and combination of SHP099 and afatinib. (E) Western blot of ERK, pERK and β-Actin on Kmt2d KO tumors treated with vehicle, SHP099, afatinib and combination of SHP099 and afatinib. (F) Heatmap of the Kras signaling dependent gene expression in tumors treated with vehicle, SHP099, afatinib, and combination of SHP099 and afatinib, assessed by RNA-seq. (G) Top negatively enriched pathways in GSEA result from combo treated versus vehicle treated Kmt2d KO tumors. (H) GSEA analysis of RNA-seq for combo treated tumors versus the vehicle treated tumors indicated that "E2F targets", "G2M checkpoint" and "Myc targets V1" were negatively enriched. (I) IHC analysis of Ki-67 and cleaved caspase-3 from Kmt2d KO tumors with indicated treatment. Scale bars, 100 μm. (J) Quantifications of IHC score of Ki-67 and cleaved caspase-3 of indicated treatment. Data shown as means±SEM. $p<0.01$, **$p<0.0001$ (unpaired two-tailed t test).

Figure 5:
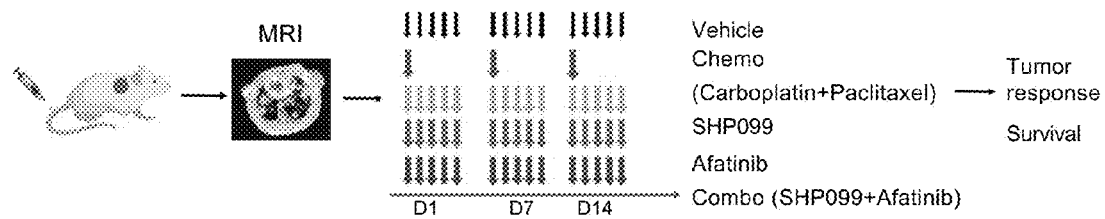
Figure 5:
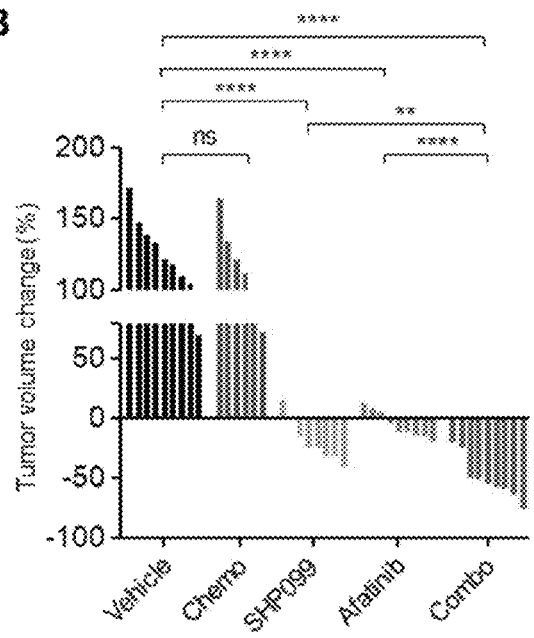
Figure 5:
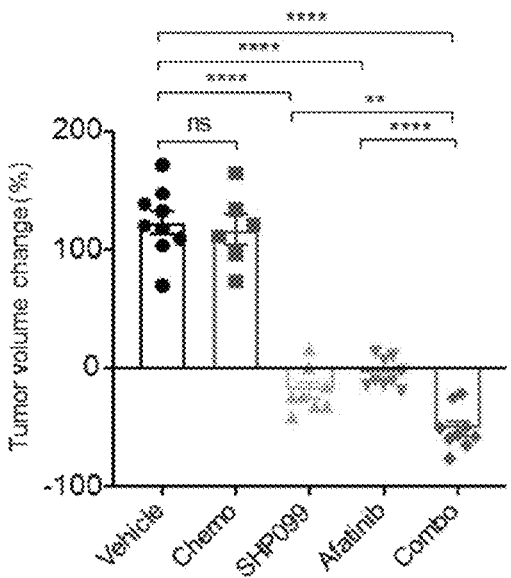
Figure 5:
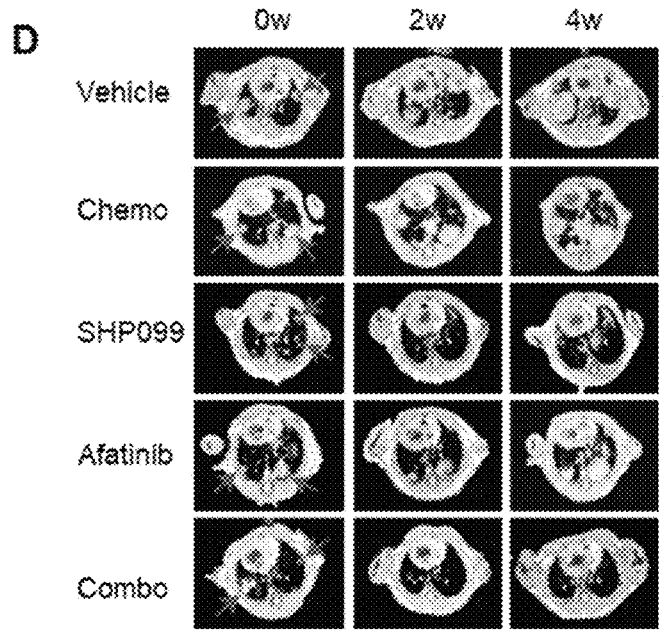
Figure 5:
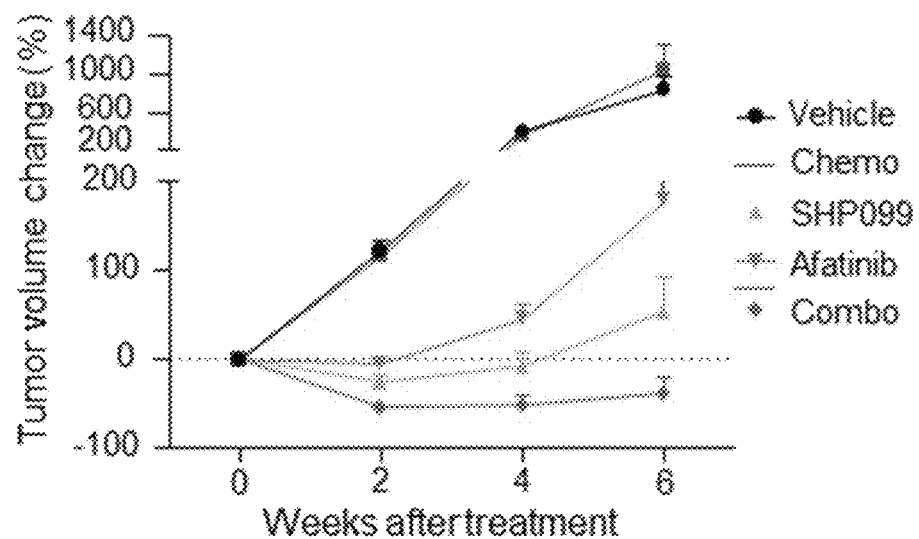
Figure 5:
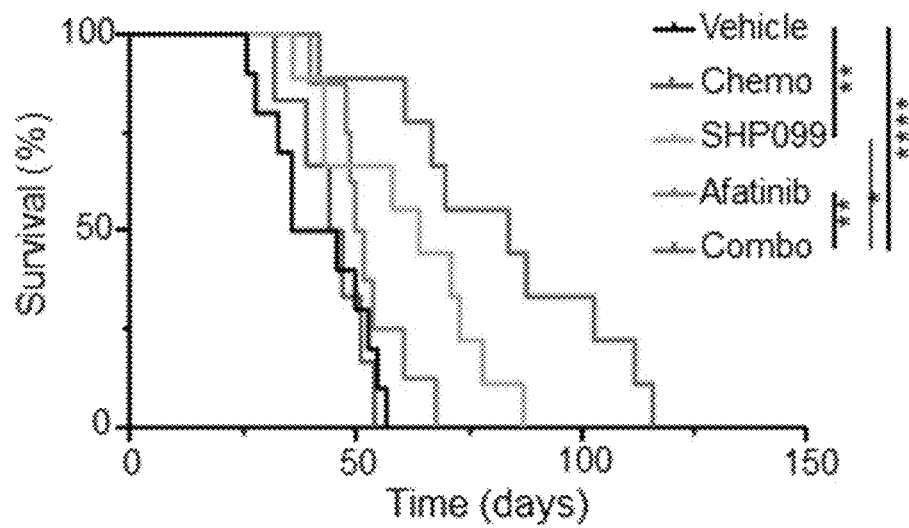
Figure 5:
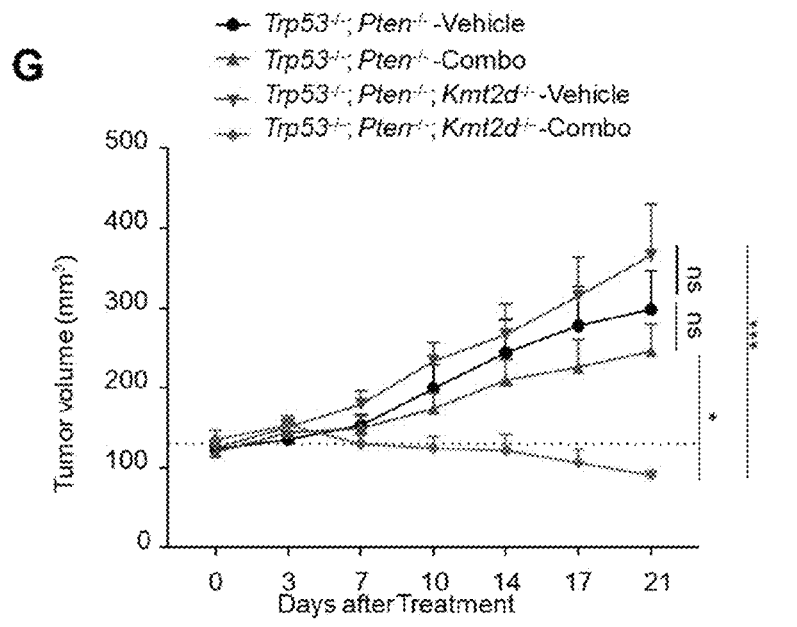
Figure 5:
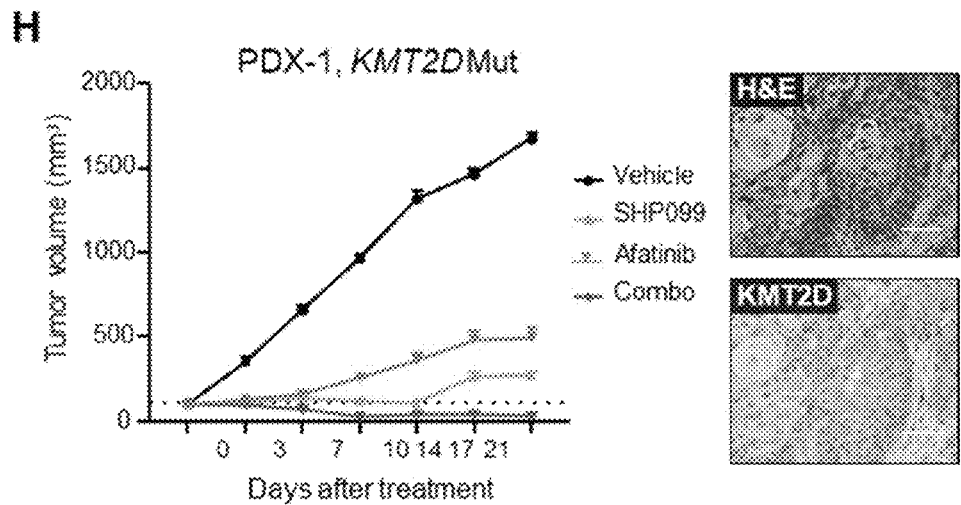
Figure 5:
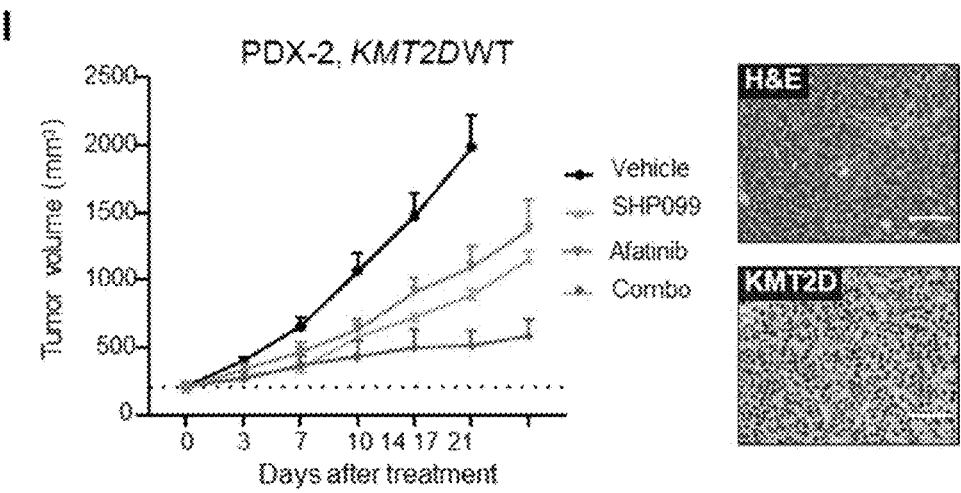
Figure 5:
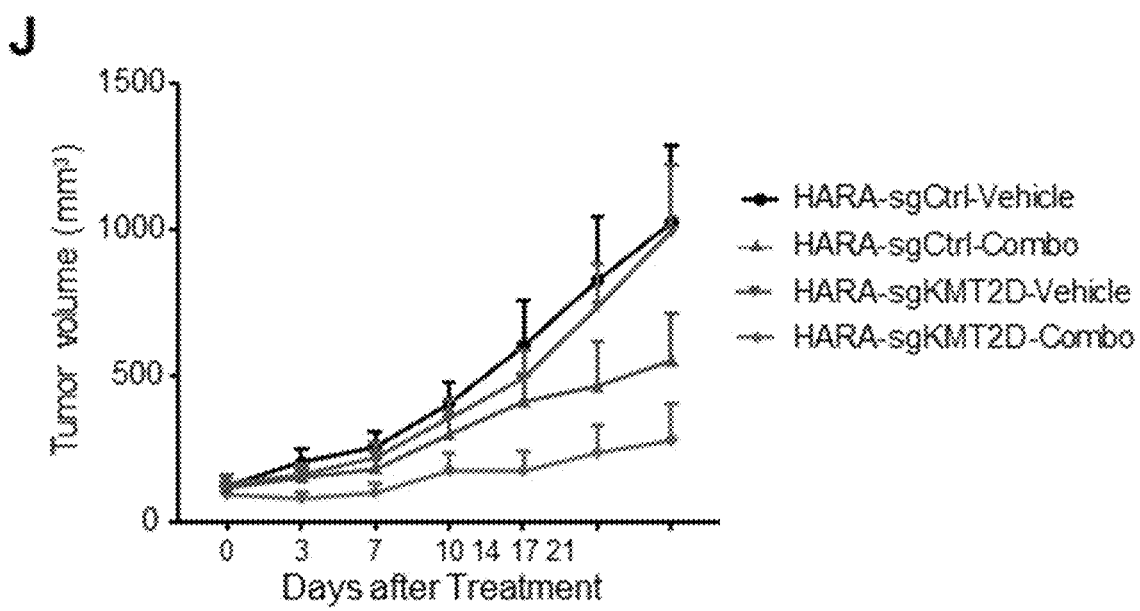
Figure 5:
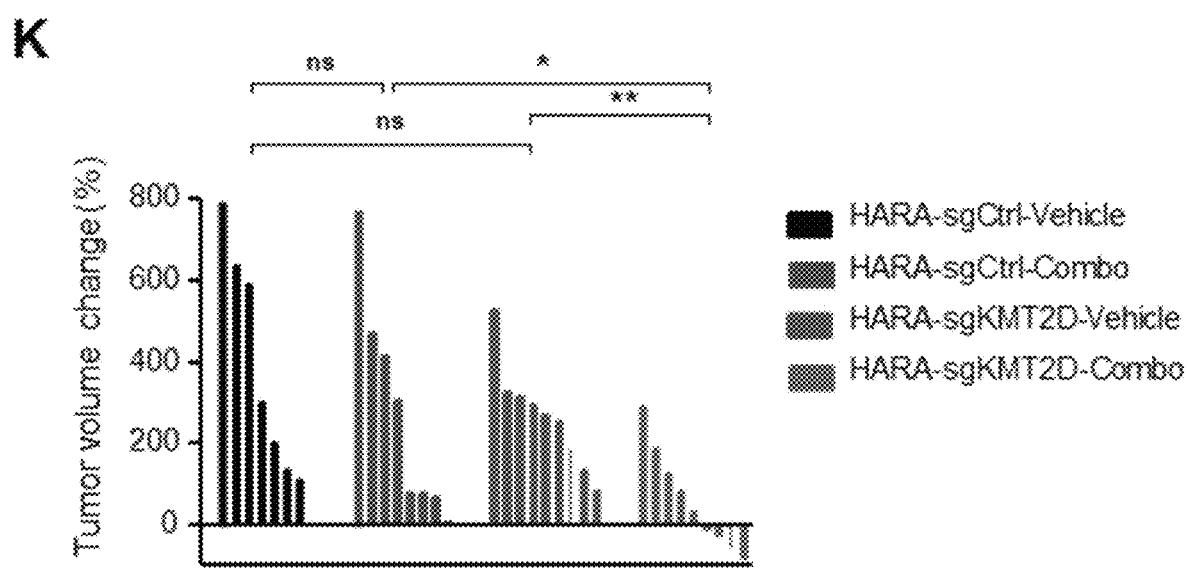

FIG. 5. SHP099 and afatinib diminish KMT2D-deficient LUSC in vivo. (A) Schematic showing in vivo dosing schedule. After inoculating LUSC cells into mice, lung tumor burden was confirmed by MRI. Mice were then randomized and treated with vehicle, chemotherapy (carboplatin+paclitaxel), SHP099 (75 mpk, 5 days per week), afatinib (10 mpk, 5 days per week) alone or combined SHP099 with afatinib. Tumor growth was measured by MIll and survival was recorded. (B and C) Waterfall plot (B) and dot plot (C) of changes in tumor volume 2 weeks after treatment initiation in Kmt2d KO LUSC model: vehicle (n=9), chemo (n=6), SHP099 (n=8), afatinib (n=9), and combo (n=9). (D) Representative MRI images of Kmt2d KO lung tumor baseline, 2 weeks, and 4 weeks after treatment initiation. The red arrows indicate the location of lung tumors. (E) Tumor volume change from treatment initiation to 6 weeks after treatment for indicated treatment in Kmt2d KO LUSC model. (F) Kaplan-Meier survival curve for the Kmt2d KO LUSC model after indicated treatment. Vehicle (n=9), chemo (n=6), SHP099 (n=9), afatinib (n=8), and combo (n=9). *$p<0.05$, $p<0.01$, $p<0.0001$ (log-rank test). (G) Tumor volumes of Trp53$^{-/-}$; Pten$^{-/-}$ (n=7-8) and Trp$^{-/-}$; Pten$^{-/-}$; Kmt2d$^{-/-}$ (n=6-8) allografts in C57BL/6J mice overtime following treatments with vehicle and combined SHP099 with afatinib. (H) Tumor volumes of KMT2D mutant LUSC PDX (PDX-1) in mice overtime following treatments with vehicle (n=4), SHP099 (n=5), afatinib (n=3) alone and combined SHP099 with afatinib (n=7). Right pictures showed the H&E staining and IHC analysis of KMT2D on the tumor. Scale bars, 100 μm. (I) Tumor volumes of Kmt2d WT LUSC PDX (PDX-2) in mice overtime following treatments with vehicle (n=6), SHP099 (n=4), afatinib (n=5) alone and combined SHP099 with afatinib (n=6). Right pictures showed the H&E staining and IHC analysis of KMT2D on the tumor. Scale bars, 100 μm. (J) Tumor volumes of human HARA-sgCtrl xenografts in mice overtime following treatments with vehicle (n=7), and combined SHP099 with afatinib (n=8), as well HARA-sgKMT2D xenografts in mice overtime following treatments with vehicle (n=9), and combined SHP099 with afatinib (n=9). (K) Waterfall plot of changes in tumor volume 2 weeks after treatment initiation in HARA-sgCtrl and HARA-sgKMT2D LUSC models. In (B), (C) and (K), data shown as means±SEM, $p<0.01$, ****$p<0.0001$, NS, not significant (unpaired two-tailed t test). In (G), data shown as means±SEM, *$p<0.05$, ***$p<0.001$, NS, not significant (two-way ANOVA).

Figure 6:
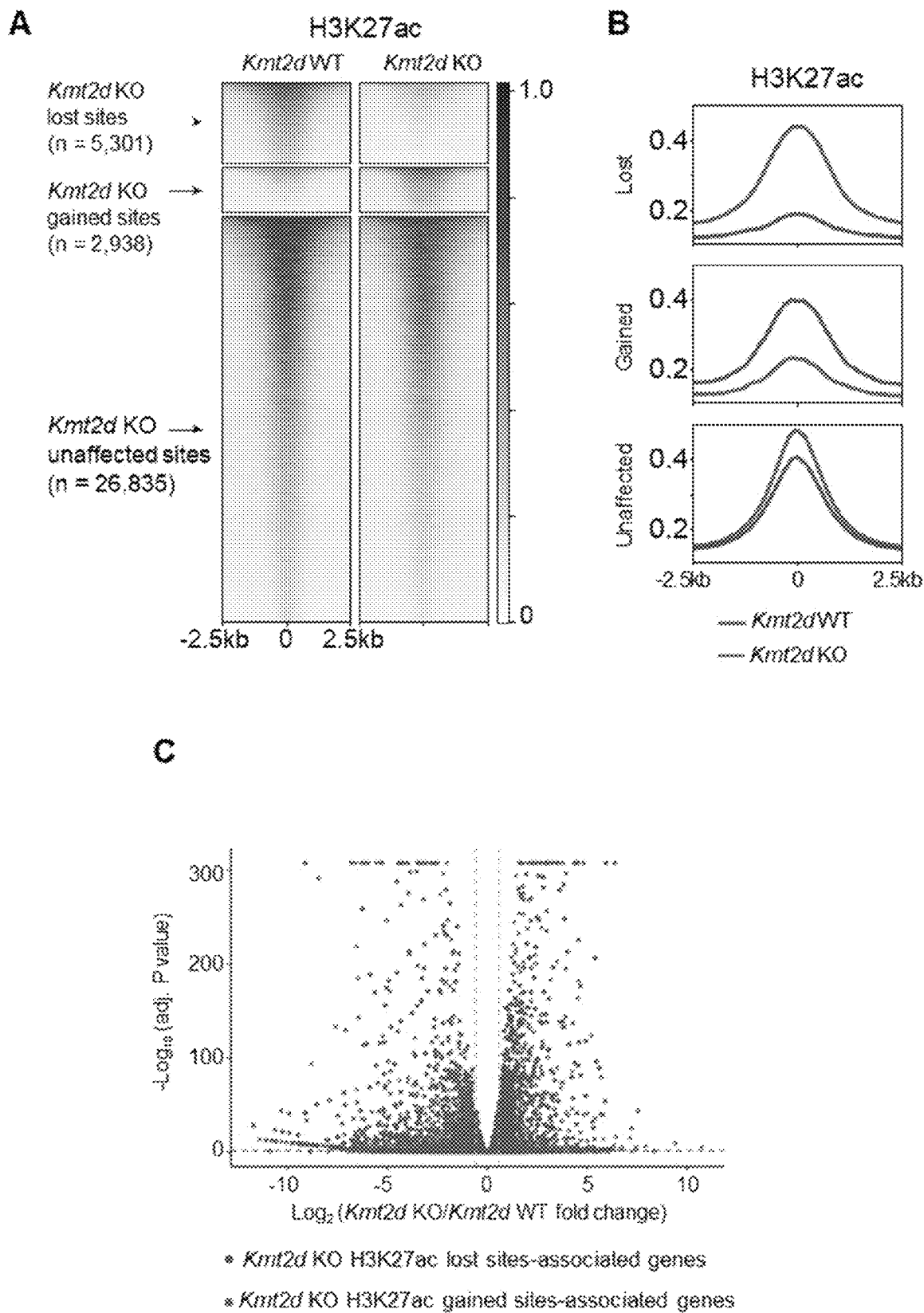
Figure 6:
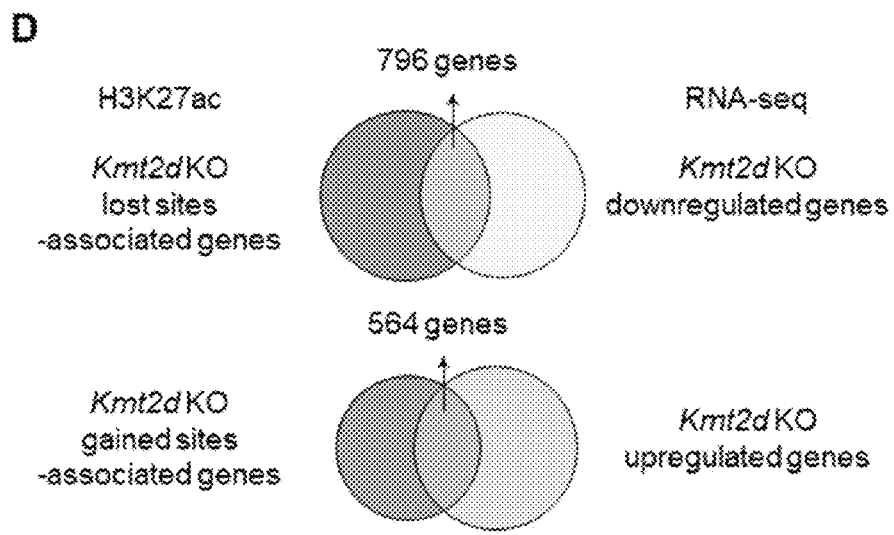
Figure 6:
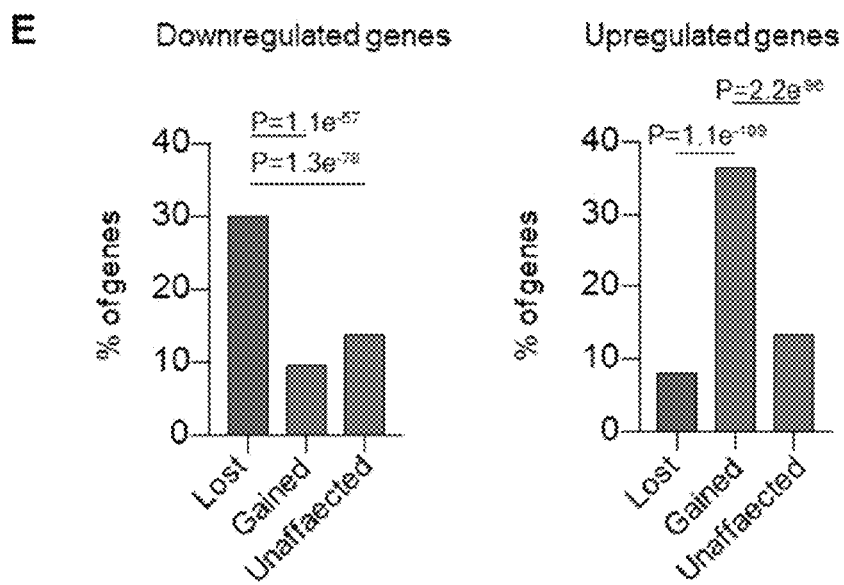
Figure 6:
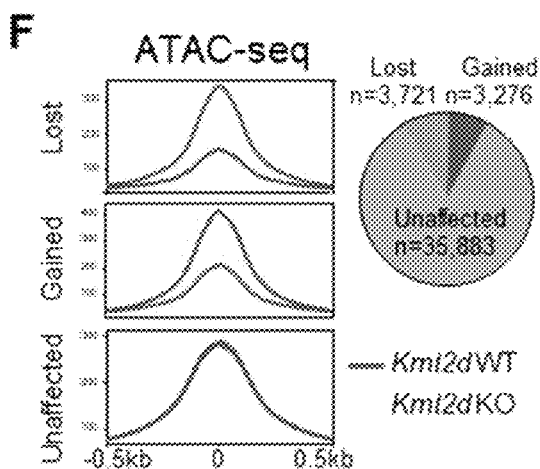
Figure 6:
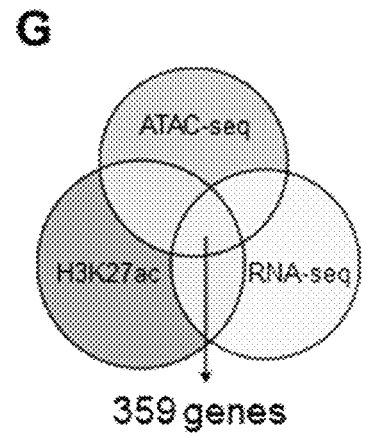
Figure 6:
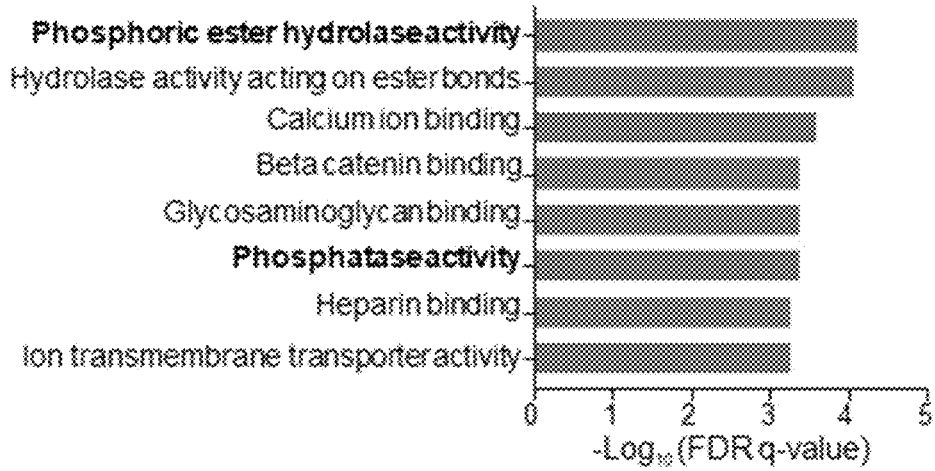
Figure 6:
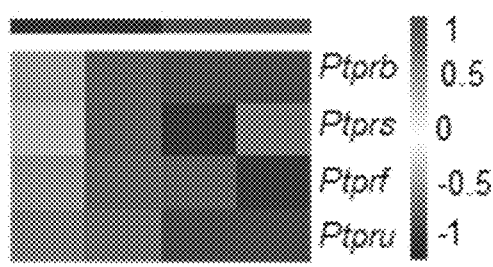

FIG. 6. KMT2D loss reprograms the epigenetic landscape in LUSC. (A) Heatmaps showing the H3K27ac ChIP-seq signal in Kmt2d WT and Kmt2d KO cell lines. Based on the ChIP-seq signal changes, H3K27ac sites were categorized into three groups: Kmt2d KO-lost, -gained and -unaffected. (B) Averaged H3K27ac ChIP-seq signal, centered at the Kmt2d KO-lost, -gained, and -unaffected H3K27ac sites. (C) RNA-seq results showing downregulated (left upper corner) and upregulated (right upper corner) genes in Kmt2d KO cell lines (FDR<0.05; Fold Change>1.5). Genes that were associated with lost and gained H3K27ac sites (genes with the closest distances to the sites) are highlighted by red and blue, respectively. (D) The comparison of lost H3K27ac sites-associated genes versus RNA-seq downregulated genes in Kmt2d KO cells (up). And the comparison of gained H3K27ac sites-associated genes versus RNA-seq upregulated genes in Kmt2d KO cells (down). (E) The percentage of genes associated with Kmt2d KO-gained, -lost and -unaffected H3K27ac sites that were downregulated (left) or upregulated (right) based on RNA-seq results. (F) Averaged ATAC-seq signal, centered at the Kmt2d KO-lost, -gained, and -unaffected ATAC-seq sites (left). Pie graft showing number of Kmt2d KO-lost, -gained, and -unaffected ATAC-seq sites (right). (G) Overlap of H3K27ac lost sites-associated genes, ATAC lost sites-associated genes, and RNA-seq downregulated genes in Kmt2d KO cells. (H) Gene ontology (GO) analysis enriched pathways in "molecular function", based on overlapped genes in (G). (I) Heatmap of RPTPs gene expression (RNA-seq) in Kmt2d KO and Kmt2d WT cells.

Figure 7:
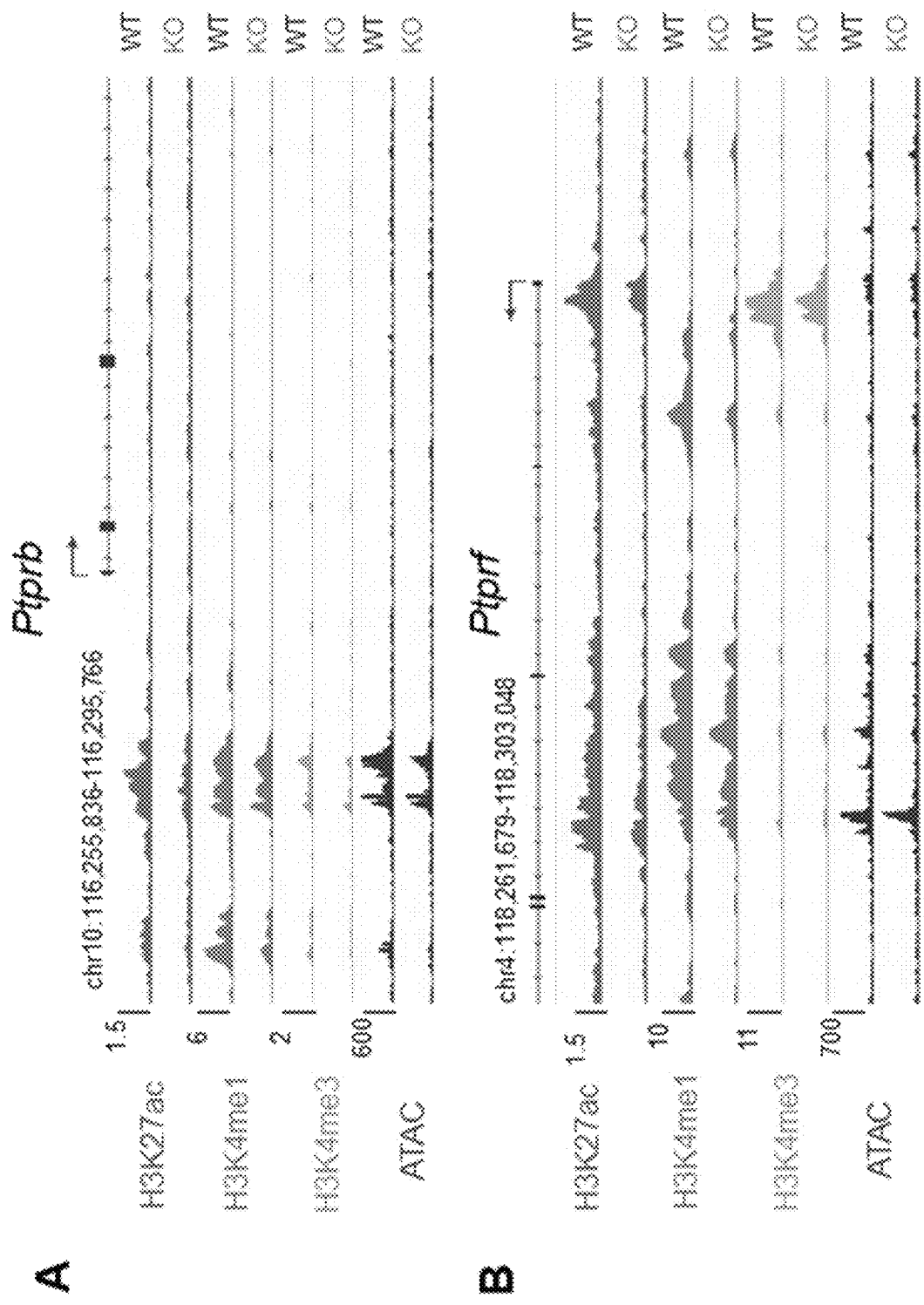
Figure 7:
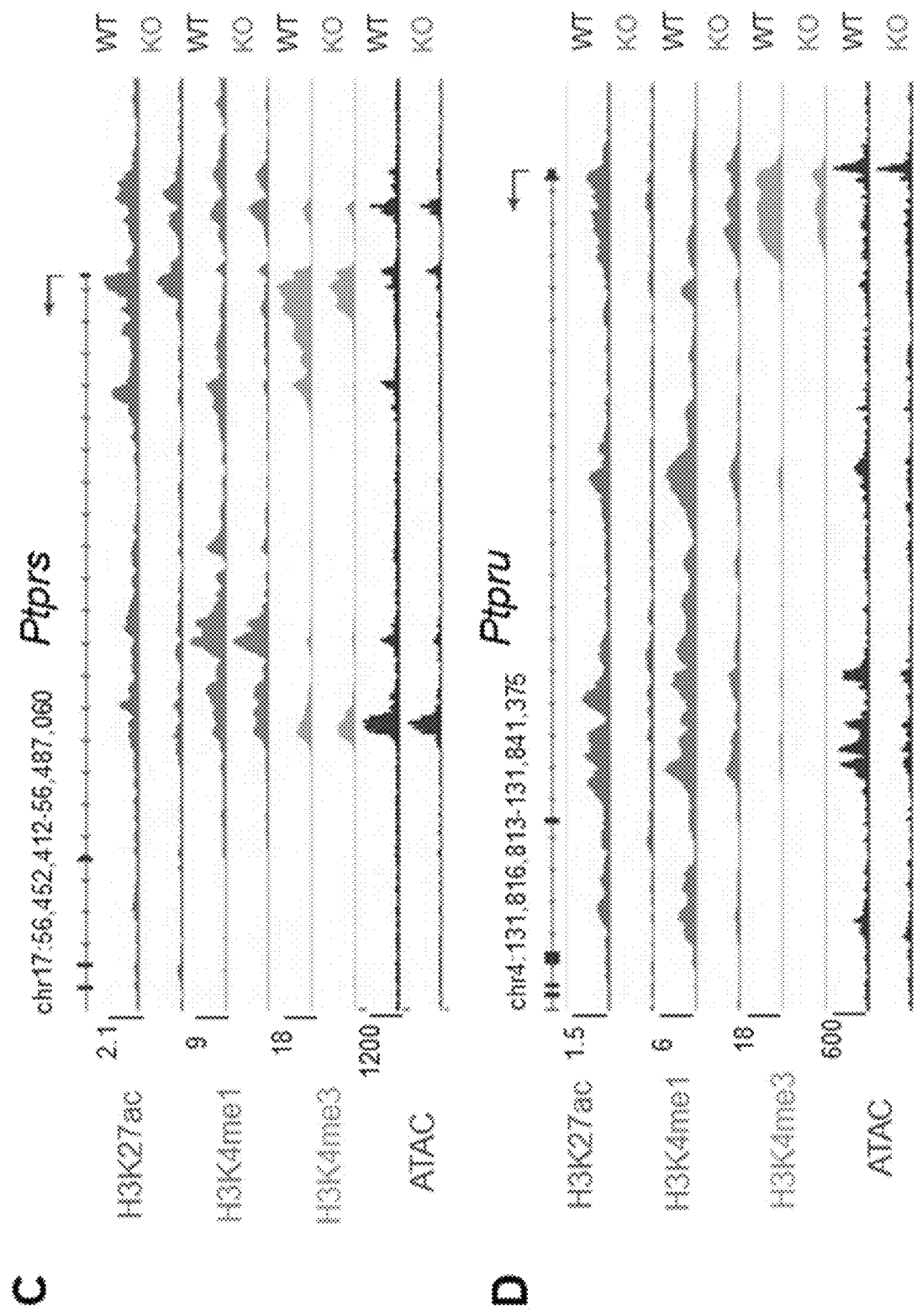
Figure 7:
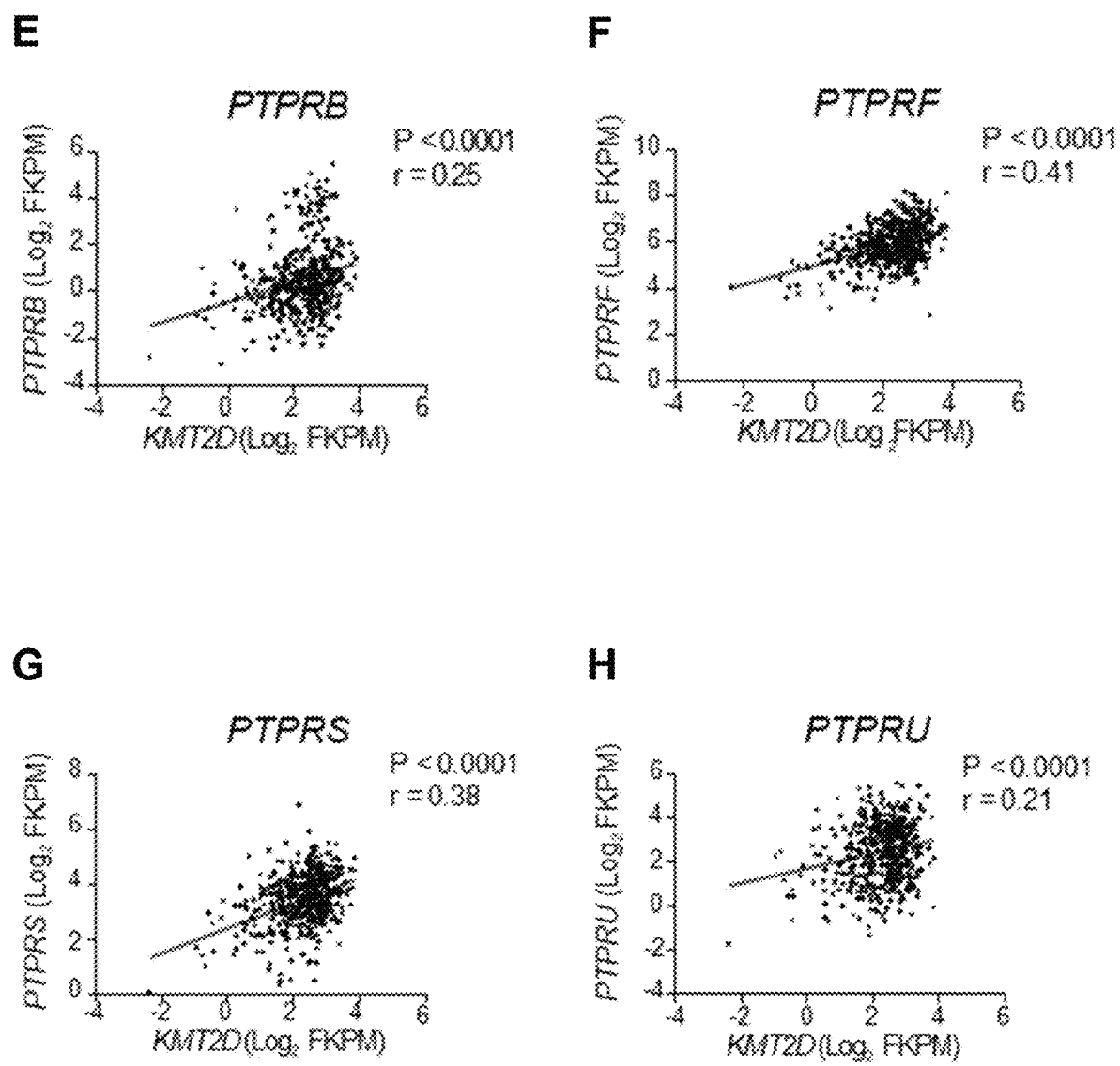
Figure 7:
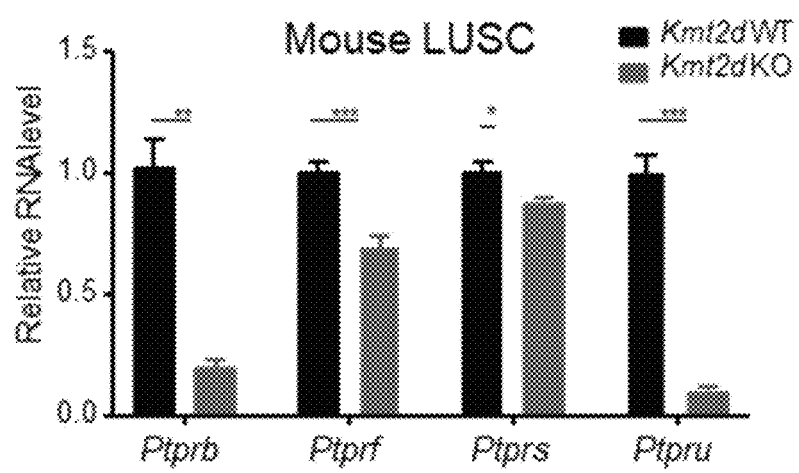
Figure 7:
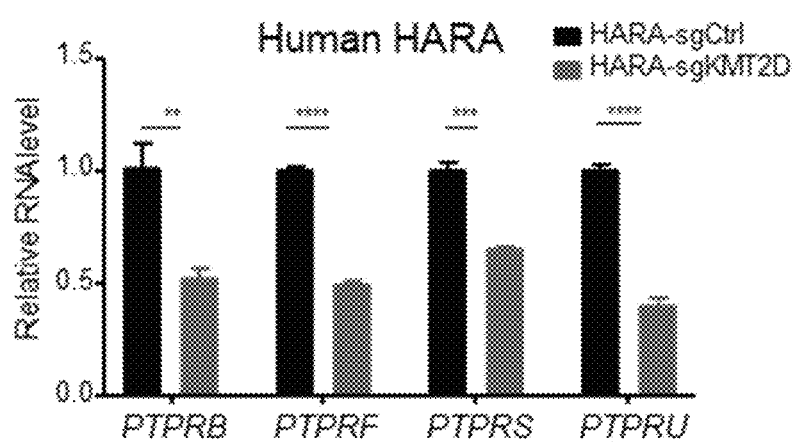
Figure 7:
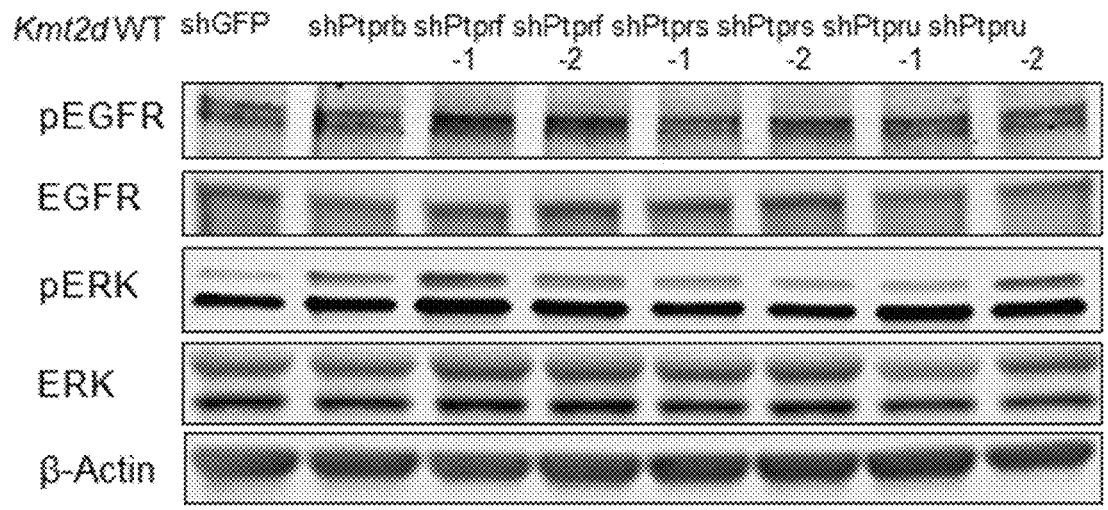
Figure 7:
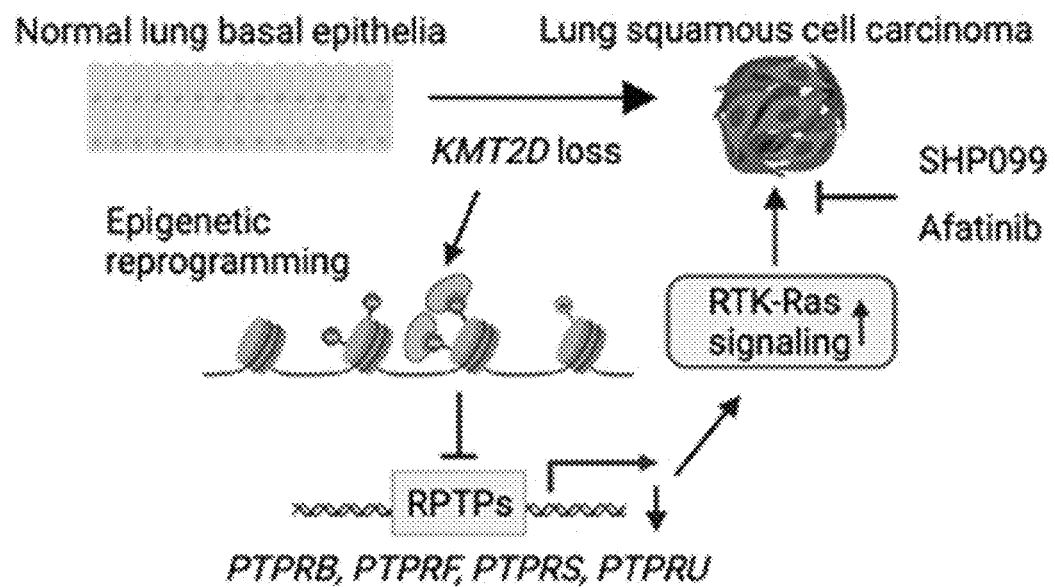

FIG. 7. KMT2D deletion suppresses receptor tyrosine phosphatase expression. (A-D) Representative H3K27ac, H3K4me1 and H3K4me3 and ATAC-seq signal at loci of Ptprb (A), Ptprf (B), Ptprs (C) and Ptpru (D) in Kmt2d KO and Kmt2d WT cells. (E-H) Scatterplots showing positive correlations of KMT2D mRNA levels with PTPRB (E), PTPRF (F), PTPRS (G) and PTPRU (H) mRNA levels in human TCGA LUSC dataset. r, Pearson's correlation coefficient. (I and J) qRT-PCR analysis of PTPRB, PTPRF, PTPRS, and PTPRU gene expression in Kmt2d KO and Kmt2d WT mouse LUSC cells (I) and human HARA cells (J). Data shown as means±SEM. *p<0.05, p<0.01, *p<0.001, ****p<0.0001 (unpaired two-tailed t test). (K) Western blot of pEGFR, EGFR, pERK, ERK and β-Actin in Kmt2d WT cells with knockdown of Ptprb, Ptprf, Ptprs and Pqvu using shRNA. (L) Schematic showing our proposed model of how KMT2D deletion promotes LUSC tumorigenesis and the therapeutic strategy to treat KMT2D-deficient LUSC.

Figure 8:
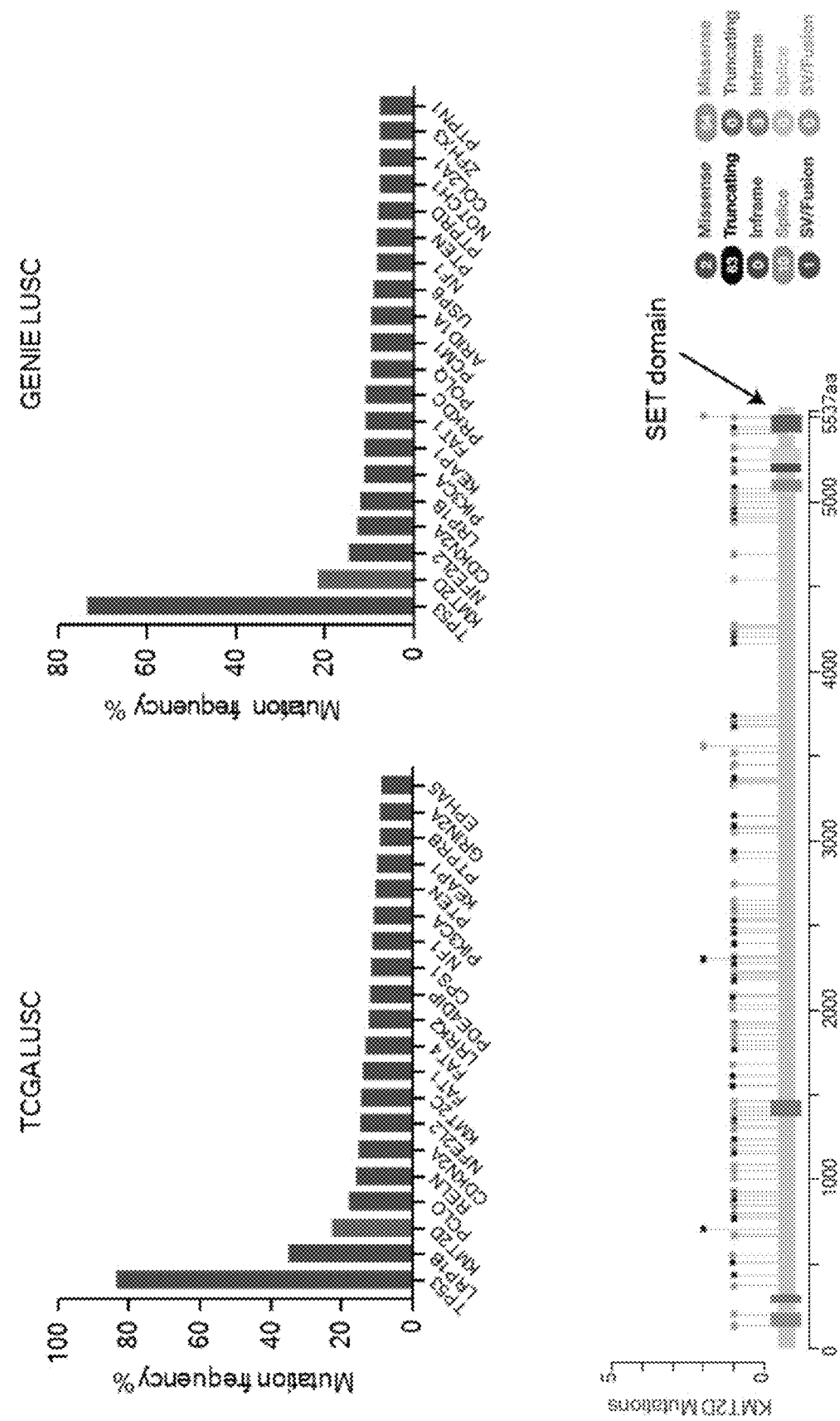
Figure 8:
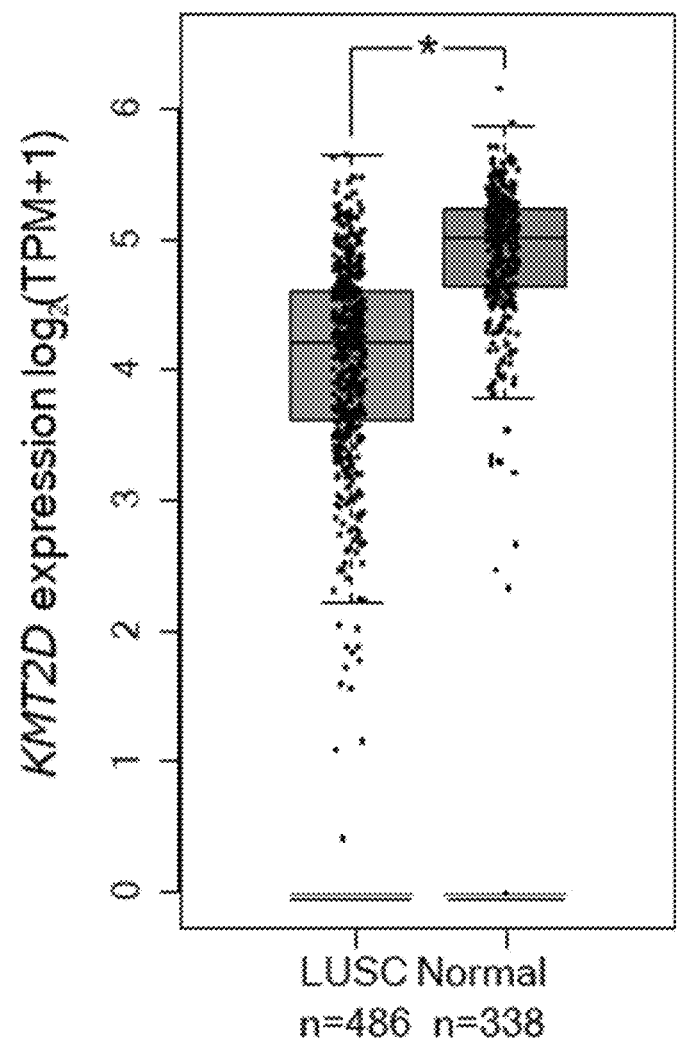

FIG. 8. KMT2D is frequently mutated in LUSC. (A) KMT2D is among the most frequently mutated tumor-related genes in LUSC according to the TCGA and GENIE databases. KMT2D is mutated in 111 of 484 LUSC samples in TCGA PanCancer Atlas dataset and is mutated in 301 of 1385 LUSC samples in GENIE dataset. (B) The lollipop graph shows mutation profiles (missense, truncation, and in frame) in the KMT2D gene in the LUSC PanCancer Atlas TCGA dataset. (C) Box plot comparing KMT2D mRNA expression levels between LUSC samples (from TCGA dataset) and matched normal samples (from TCGA and GTEx projects), using the GEPIA2 online server (http://gepia2.cancer-pku.cn/).

Figure 9:
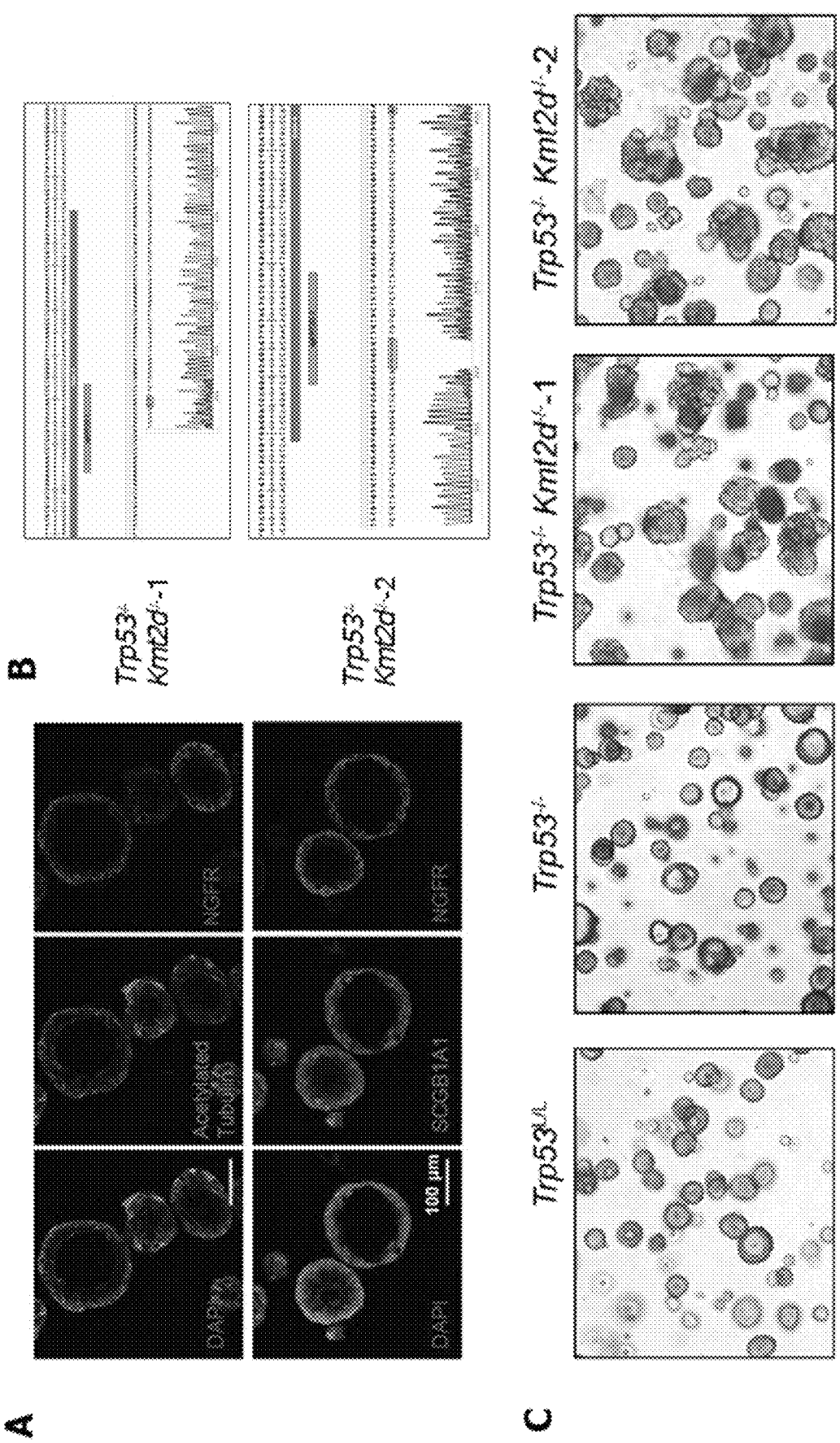
Figure 9:
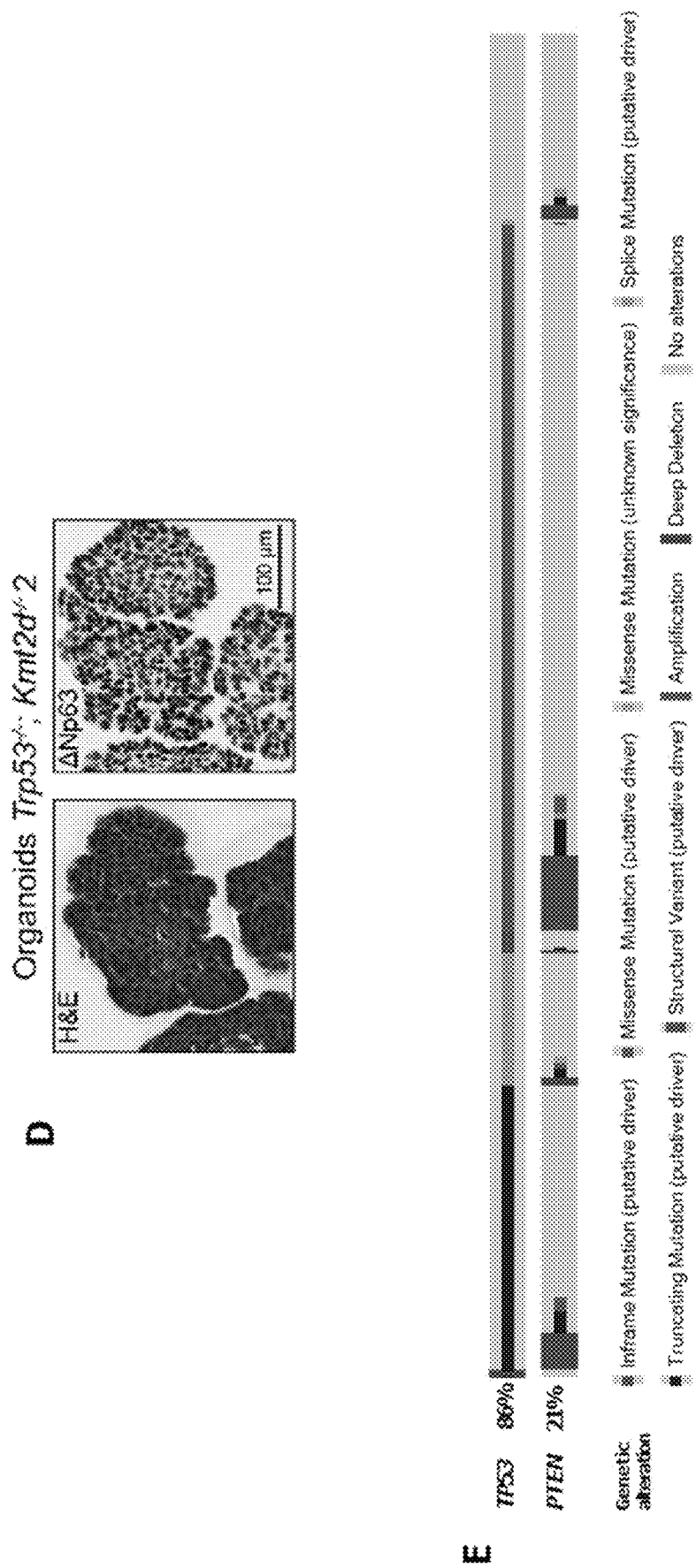
Figure 9:
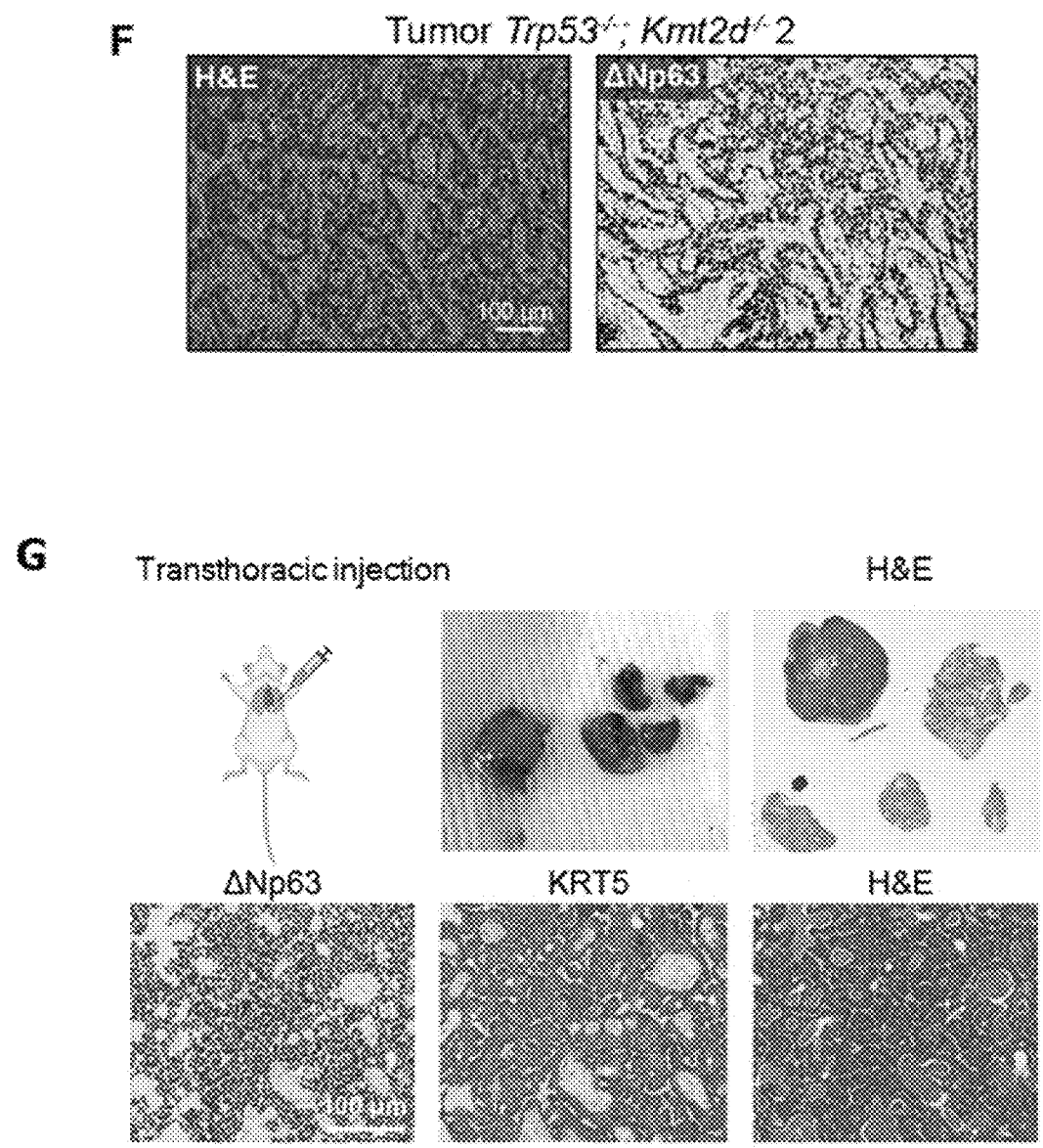

FIG. 9. Kmt2d deletion transforms the lung basal organoids into LUSC. (A) Representative immunofluorescence staining of $Trp53^{L/L}$ basal cell organoids after 7 days in culture. Scale bars, 100 μm. Organoids were stained with DAPI (blue), NGFR (red), Acetylated Tubulin (green) and SCGB1A1 (green). NGFR, Acetylated Tubulin and SCGB1A1 mark the basal cells, ciliated cells and club cells, respectively. (B) Representative chromatogram sequences of Kmt2d loci in the $Trp53^{-/-}$; $Kmt2d^{-/-}$-1 and $Trp53^{-/-}$; $Kmt2d^{-/-}$-2 organoids. (C) Representative brightfield images of $Trp53^{-/-}$ and $Trp53^{-/-}$; $Kmt2d^{-/-}$ organoids after 7 days in culture. $Trp53^{-/-}$; $Kmt2d^{-/-}$-1 and $Trp53^{-/-}$; $Kmt2d^{-/-}$-2 are from two different sgRNA targeting Kmt2d. (D) Representative hematoxylin and eosin (H&E) staining, and immunohistochemistry (IHC) staining of ΔNp63 in $Trp53^{-/-}$; $Kmt2d^{-/-}$-2 organoids. Scale bars, 100 μm. (E) OncoPrint showing frequency of PTEN mutations and their co-occurrence with TP53 in human LUSC database (TCGA, PanCancer Atlas). (F) Representative hematoxylin and eosin (H&E) staining, and immunohistochemistry (IHC) staining of ΔNp63 in $Trp53^{-/-}$; $Kmt2d^{-/-}$-2 organoids. Scale bars, 100 μm. (G) Schematic illustration of transthoracic injection of $Trp53^{-/-}$; $Kmt2d^{-/-}$ organoids. The of $Trp53^{-/-}$; $Kmt2d^{-/-}$ lung tumors were analyzed by H&E staining and IHC analysis of ΔNp63 and KRT5. Scale bars, 100 μm.

Figure 10:
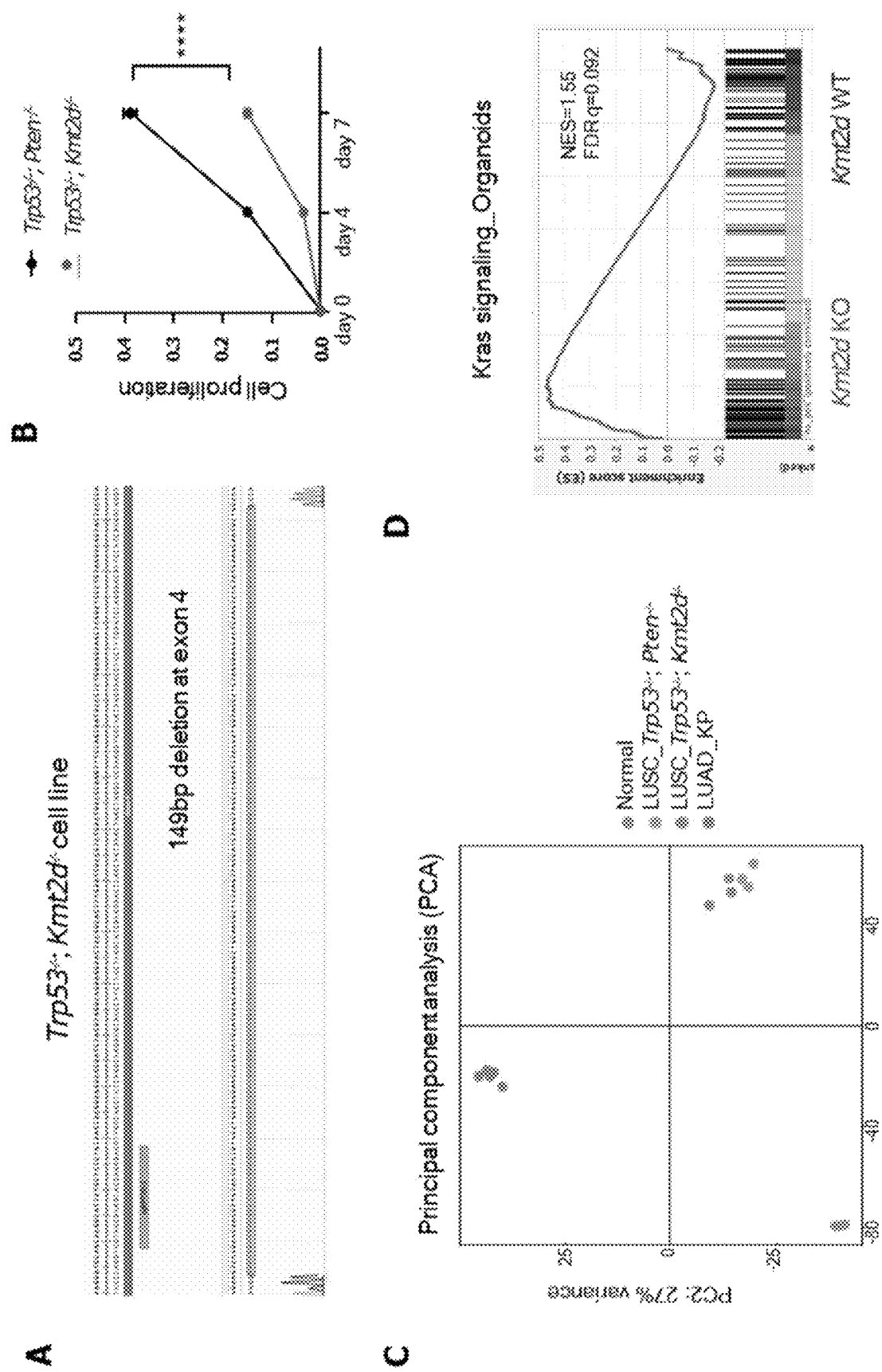
Figure 10:
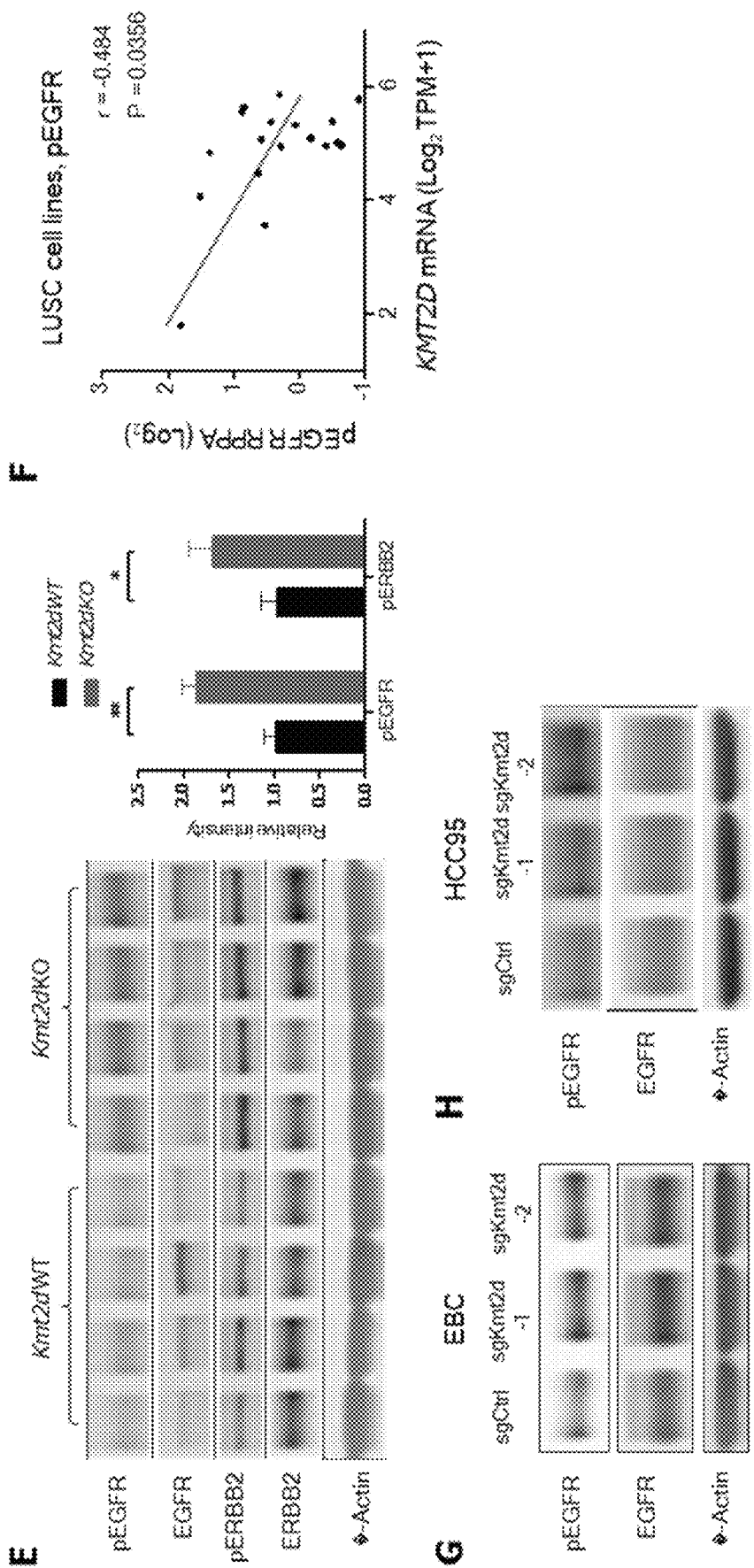

FIG. 10. Validation of Kmt2d KO cell line and RNA-seq analysis of LUSC tumors and organoids. (A) Representative chromatogram sequences of Kmt2d loci in the $Trp53^{-/-}$; Kmt2d cell line. (B) Cell proliferation of $Trp53^{-/-}$; $Kmt2d^{-/-}$ and $Trp53^{-/-}$; $Pten^{-/-}$ cells over time. (C) Principal component analysis (PCA) of gene expression in normal mouse lung tissues, LUAD ($Kras^{G12D}$; $Trp53^{-/-}$) and LUSC of $Trp53^{-/-}$; $Kmt2d^{-/-}$ and $Trp53^{-/-}$; $Pten^{-/-}$. (D) GSEA analysis of RNA-seq for Kmt2d KO ($Trp53^{-/-}$; $Kmt2d^{-/-}$) versus Kmt2d WT ($Trp53^{-/-}$) organoids indicated that Kras signaling was significantly enriched. (E) Western blot of pEGFR, EGFR, ERBB2 and pERBB2 and β-Actin, and quantification of relative pEGFR and pERBB2 in Kmt2d KO and Kmt2d WT LUSC tumors. Data shown as means±SEM. *p<0.05, **p<0.01 (unpaired two-tailed t test). (F) Scatterplots showing negative correlations of KAIT2D mRNA levels with pEGFR in human LUSC cell lines (n=19) DepMap dataset (depmap.org/portal/). r, Pearson's correlation coefficient. (G) Western blot of pEGFR, EGFR, and β-Actin in EBC1-sgCtrl and EBC1-sgKMT2D cells. (H) Western blot of pEGFR, EGFR, and β-Actin in HCC95-sgCtrl and HCC95-sgKMT2D cells.

Figure 11:
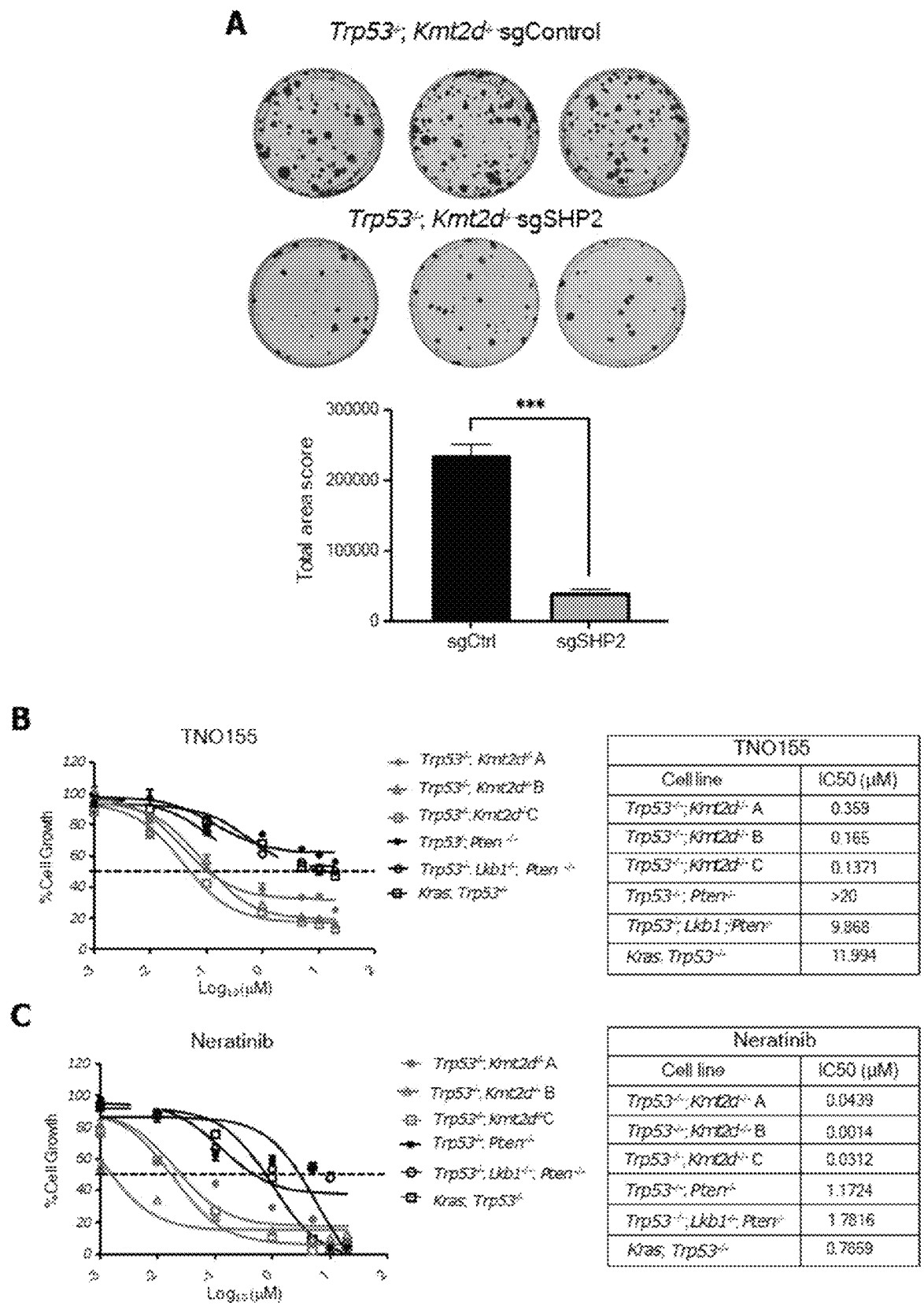
Figure 11:
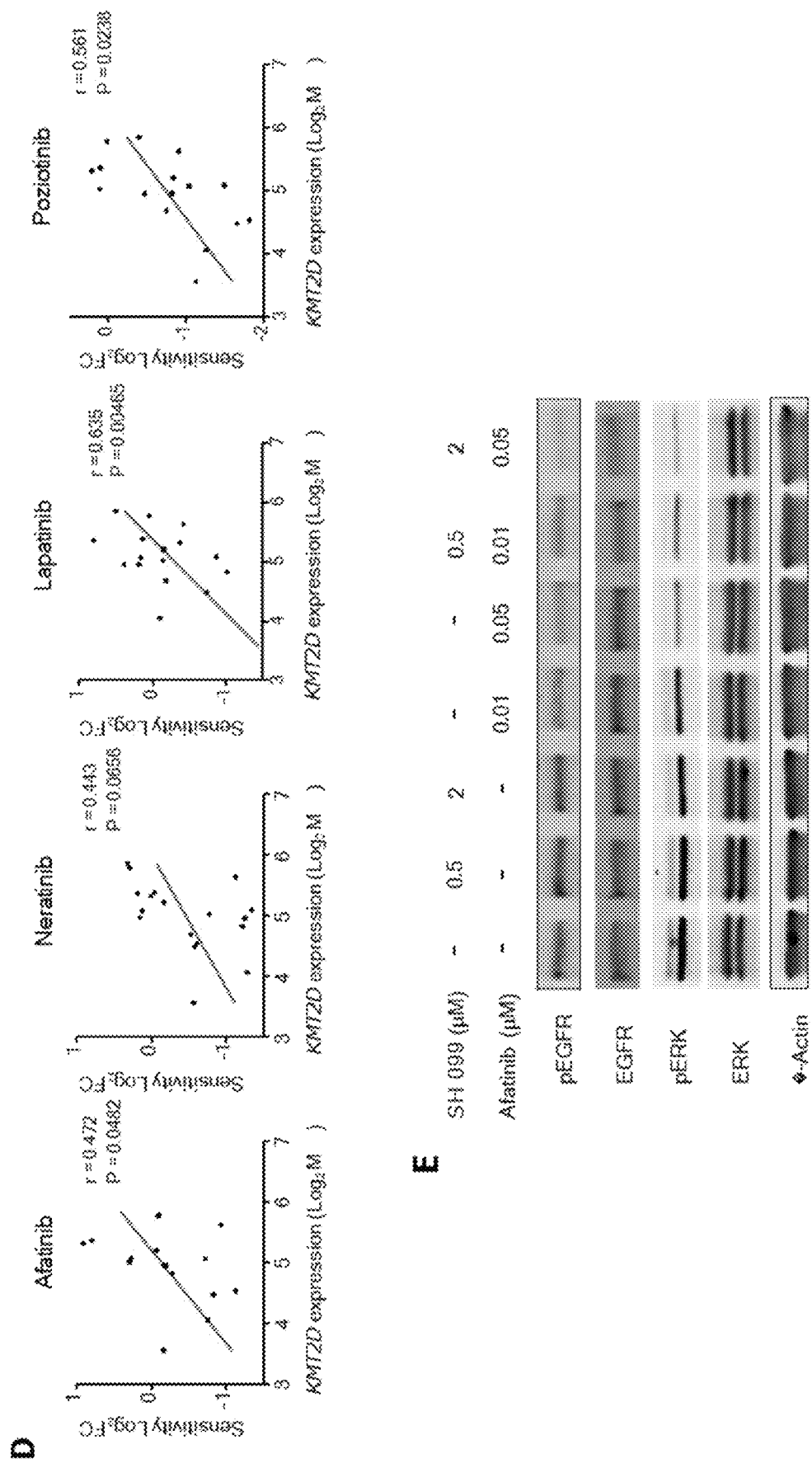

FIG. 11. KMT2D-deficient LUSC cells are hypersensitive to SHP2 and ERBB inhibition. (A) Colony formation assay of $Trp53^{-/-}$; $Kmt2d^{-/-}$-sgControl and $Trp53^{-/-}$; $Kmt2d^{-/-}$-sgSHP2 cells. The quantification is shown below. Data shown as means±SEM. ***p<0.001 (unpaired two-tailed t test). (B and C) Cellular viability assays of Kmt2d KO LUSC cell lines, Kmt2d WT LUSC cell lines, and LAD (KP) cell line treated with TNO155 (B) and neratinib (C) for 72 h. Data presented as mean±s.d. (n=3). The calculated IC50 values of TNO155 and neratinib are shown on the right. (D) Scatterplots showing correlations of KA/T2D mRNA levels with sensitivity of afatinib, neratinib, lapatinib and poziotinib (Log 2 fold change) in human LUSC cell lines DepMap dataset (https://depmap.org/portal/, Drug sensitivity 19Q4). For the drug sensitivity, lower Log 2 FC indicates higher sensitivity. r, Pearson's correlation coefficient. (E) Western blot of pEGFR, EGFR, pERK, ERK and β-Actin on Kmt2d KO LUSC cells treated with SHP099, afatinib alone or in combination for 6 h.

Figure 12:
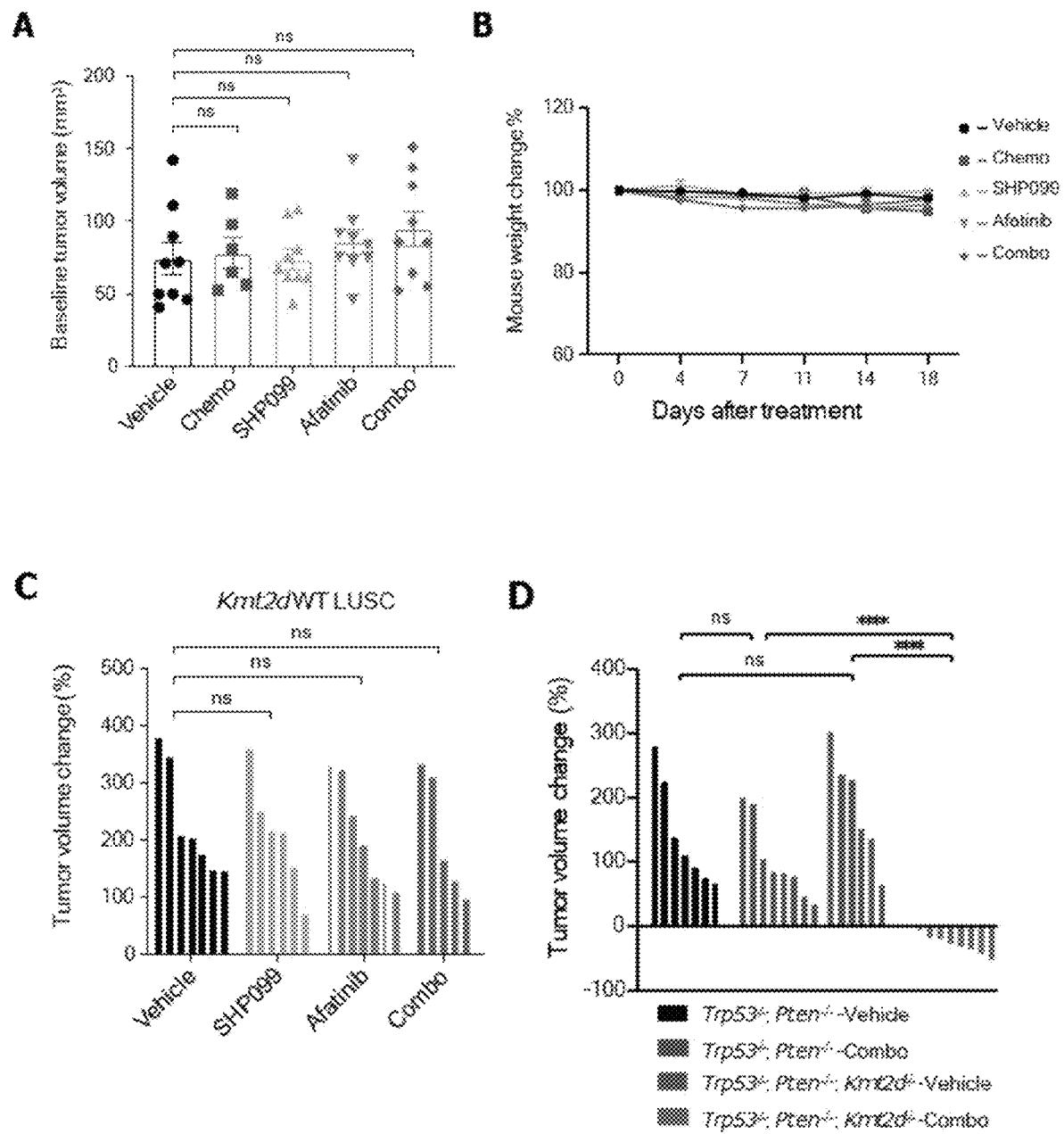
Figure 12:
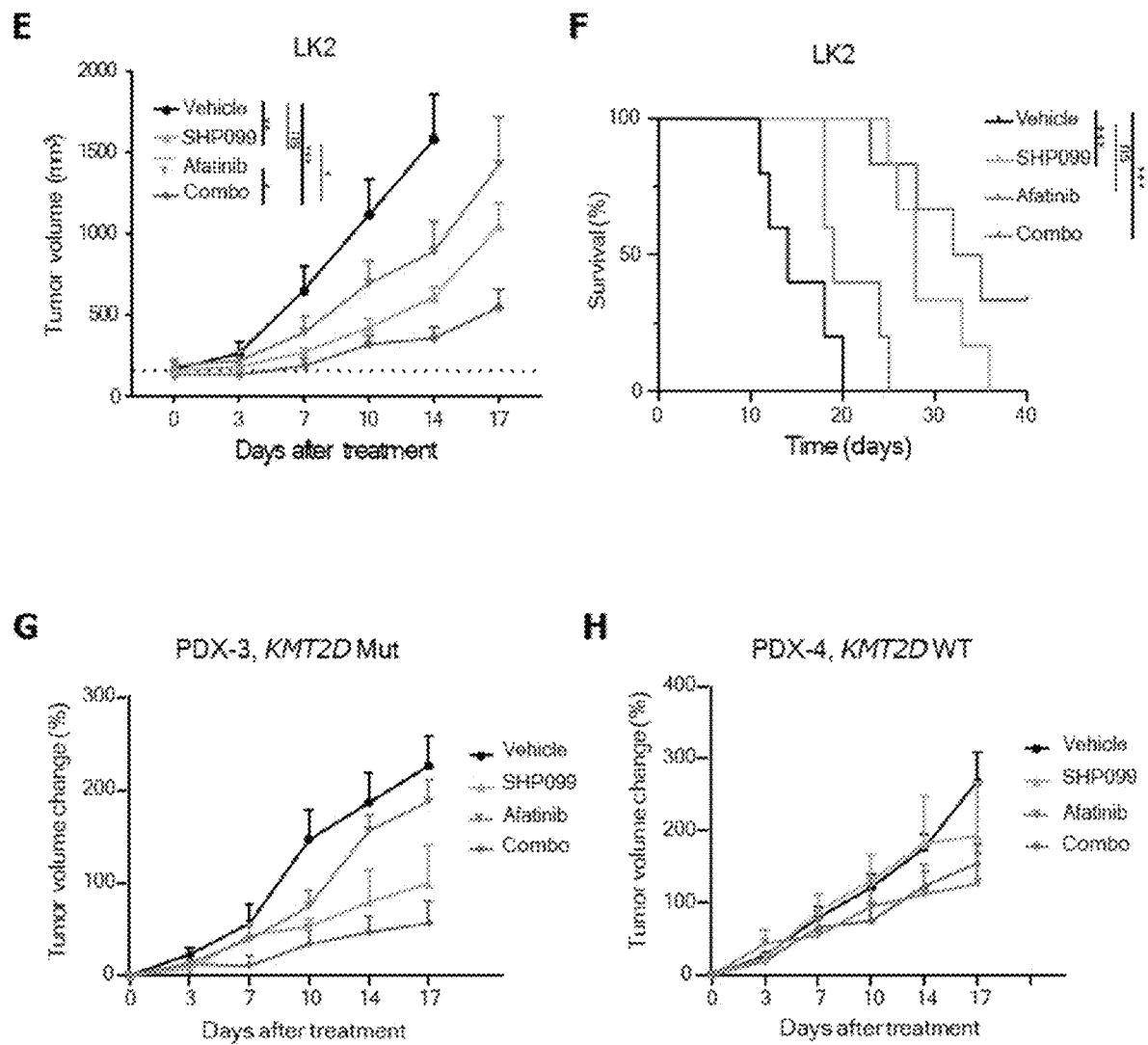

FIG. 12. SHP099 and afatinib diminish KMT2D-deficient LUSC in vivo. (A) Baseline tumor volume of Kmt2d KO LUSC with indicated treatment arms. Data shown as means±SEM. NS, not significant (unpaired two-tailed t test). (B) Mouse weight change overtime in with indicated treatment arms. (C) Waterfall plot of changes in tumor volume of 2 weeks after treatment initiation in Kmt2d WT LUSC ($Trp53^{-/-}$; $Pten^{-/-}$). Data shown as means±SEM. NS, not significant (unpaired two-tailed t test). (D) Waterfall plot of changes in tumor volume 3 weeks after treatment initiation in $Trp53^{-/-}$; $Pten^{-/-}$ and $Trp53^{-/-}$; $Pten^{-/-}$; $Kmt2d^{-/-}$ models. Data shown as means±SEM. ****p<0.0001, NS, not significant NS, not significant (unpaired two-tailed t test). (E) Tumor volumes of human LK2 xenografts in nude mice overtime following treatments with vehicle (n=9), SHP099 (n=11), afatinib (n=9) alone and combined SHP099 with afatinib (n=11). Data shown as means±SEM, *p<0.05, p<0.01, *p<0.001, NS, not significant (two-way ANOVA). (F) Kaplan-Meier survival curve for the Kmt2d mutant LK2 LUSC model after indicated treatment. ***p<0.01, NS, not significant (log-rank test). (G) Tumor volume change of KA/T2D mutant LUSC PDXs (PDX-3) in mice overtime following treatments with vehicle (n=4), SHP099 (n=4), afatinib (n=4) alone and combined SHP099 with afatinib (n=4). (H) Tumor volume change of KA/T2D WT LUSC PDXs (PDX-4) in mice overtime following treatments with vehicle (n=4), SHP099 (n=4), afatinib (n=4) alone and combined SHP099 with afatinib (n=4).

Figure 13:
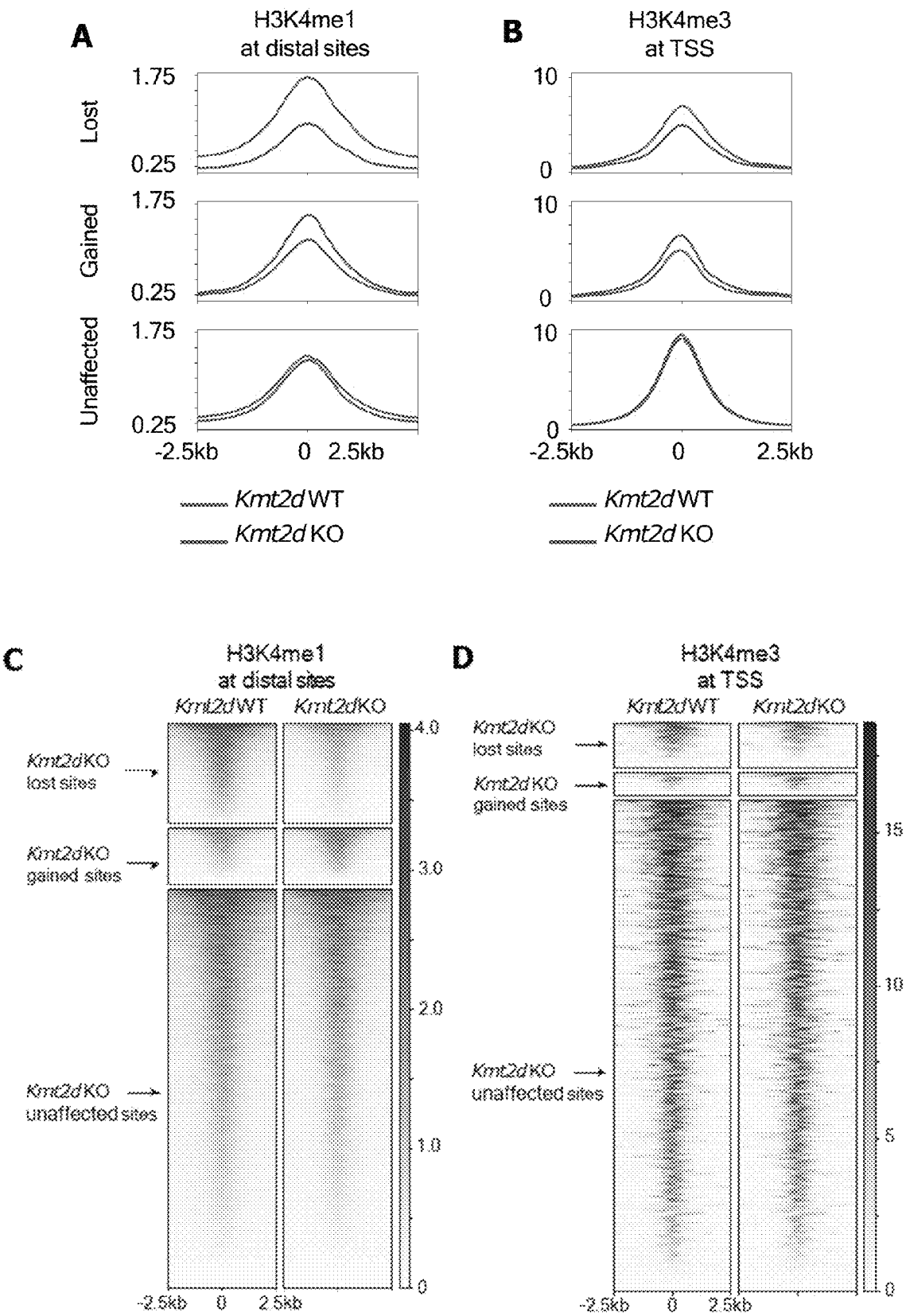
Figure 13:
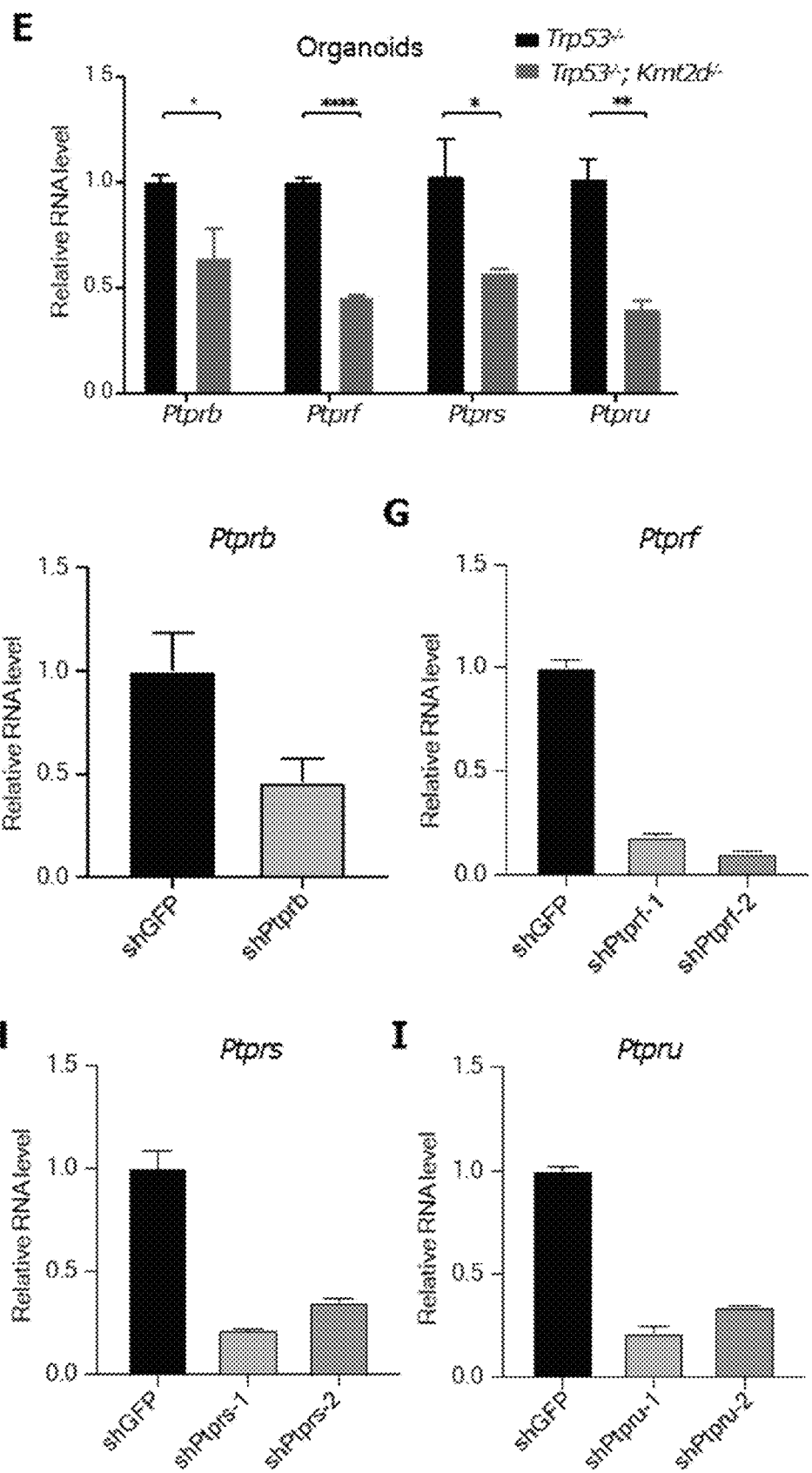

FIG. 13. Kmt2d loss reprograms the epigenetic landscape that represses the expression of protein tyrosine phosphatases in LUSC. (A and B) Averaged CUT&Tag signals of H3K4me1 (A) at distal sites, and H3K4me3 (B) at transcription start sites (TSS), centered at the Kmt2d KO-lost, -gained, and -unaffected H3K27ac sites. (C and D) Heatmaps showing the H3K4me1 (C) at distal sites and H3K4me3 (D) at TSS of CUT&Tag signals in Kmt2d WT and Kmt2d KO cell lines. Based on the CUT&Tag signal changes, H3K4me1 sites and H3K4me3 sites were categorized into three groups: Kmt2d KO-lost, -gained and -unaffected. (E) qRT-PCR analysis of Ptprb, Pqiff, Ptprs, and Ptpru gene expression in $Trp53^{-/-}$ organoids and $Trp53^{-/-}$; $Kmt2d^{-/-}$ organoids. Data shown as means±SEM. *p<0.05, p<0.01, **p<0.0001 (unpaired two-tailed t test). (F-I) qRT-PCR analysis of Ptprb (F), Ptprf (G), Ptprs (H) and Ptpru (I) gene expression in Kmt2d WT mouse LUSC cells using shRNA of shPtprb, shPtprf, shPtprs and shPtpru, respectively.

DESCRIPTION OF THE DISCLOSURE

Unless defined otherwise, all technical and scientific terms used herein have the same meaning as commonly understood by one of ordinary skill in the art to which this invention belongs.

Every numerical range given throughout this specification includes its upper and lower values, as well as every narrower numerical range that falls within it, as if such narrower numerical ranges were all expressly written herein.

As used in the specification and the appended claims, the singular forms "a" "and" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about" it will be understood that the particular value forms another embodiment. The term "about" in relation to a numerical value is optional and means for example +/−10%.

In the present disclosure, using an organoid system that entails culturing and engineering of primary normal stem cells in vitro, we identified that KMT2D, which is known to be mutated in ~20% of LUSC patients, is essential for LUSC tumorigenesis. We demonstrate that KMT2D loss drives LUSC formation through activating the RTK-Ras signaling. The disclosure thus identifies KMT2D as a biomarker for LUSC and supports use of SHP2 and/or EGFR inhibitors for treatment of LUSC.

In an aspect, the present disclosure provides a method of identification of patients afflicted with LUSC who will benefit from administration of SHP2 inhibitors or EGFR inhibitors, or a combination thereof. The method comprises determining the presence of KMT2D mutation in a tumor sample from the individual in need of treatment. The presence of the mutation indicates the individual is a candidate for treatment with SHP2 and/or EGFR inhibitor therapy.

In an aspect, the present disclosure provides methods for treatment of LUSC characterized by KMT2D mutations. The disclosure shows that KMT2D loss activates RTK-Ras signaling in LUSC. KMT2D mutations, which occur in approximately 20% in LUSC, is an oncogenic driver for LUSC. The present disclosure provides a method for treatment of individuals afflicted with LUSC who carry a KMT2D mutation comprising administration of inhibitor or inhibitors RTK-Ras signaling. The present disclosure also provides compositions and kits for the treatment of KMT2D mutated LUSC.

In embodiments, a therapeutically effect amount of a described inhibitor is administered to an individual who has LUSC and a KMT2D mutation. The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like. Appropriate effective amount can be determined by one of ordinary skill in the art informed by the instant disclosure using only routine experimentation. Within the meaning of the disclosure, "treatment" also includes prophylaxis and treatment of relapse, as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy. Administrations may be intermittent, periodic, or continuous.

The terms "KMT2D mutated" is used interchangeably with KMT2D deficient or mutant. These terms and KMT2D mutation or loss of function mutation when referring to KMT2D, as used herein, all refer to mutations likely to cause a defect in the KMT2D protein. A defect in the KMT2D protein can be caused by loss of function mutation in the gene, or a defect in the function of the protein. For example, truncated mutations, including nonsense mutations and frameshift mutations, can result in a dysfunctional KMT2D protein.

KMT2D deficient cells may be identified by obtaining a tumor tissue sample from the individual, sequencing the tumor tissue sample; and assessing the KMT2D gene for loss-of-function mutation. KMT2D deficient cells may be identified by detecting at the nucleic acid level or at the protein level. The loss of function may be due to nucleic acid that is translated or transcribed at a detectably lower level in a cancer cell, in comparison to a normal cell. The loss of function may be due to gene deletion, mutation of a gene rendering the gene non-functional with respect to transcription or translation, transcription, post transcriptional processing, translation, post-translational processing, cellular localization (e.g., organelle, cytoplasm, nucleus, cell surface), or RNA and protein stability, as compared to a control, or a protein with significantly less activity compared to a control. Loss of function may be manifested as underexpression and can be detected using conventional techniques for detecting mRNA (i.e., RT-PCR, PCR, hybridization) or proteins (i.e., ELISA, immunoblotting, immunohistochemical techniques). Underexpression can be 0%, 10%, 20%, 30%, 40%, 50%, 60%, 70%, 80%, 90% or less in comparison to a control.

The present disclosure is based on the unexpected identification that KMT2D, an epigenetic regulator, is an oncogenic driver for LUSC. The disclosure demonstrates that the KMT2D mutation drives LUSC formation in vivo. KMT2D loss activates RTK-Ras signaling pathway, which is partially mediated by SHP2 and EGFR. The disclosure also demonstrates that LUSC cancer cells comprising a mutant KMT2D gene are selectively sensitive to RTK-Ras inhibition. Based at least on these observations, the present disclosure provides a method where one or more of SHP2 and/or EGFR inhibitors can be used to treating KMT2D-mutant LUSC patients.

In an aspect, this disclosure provides a method for treatment LUSC comprising administering to an individual in need of treatment one or more inhibitors of RTK-Ras signaling pathway. As discussed herein, the LUSC cells may also have a mutation in the KMT2D gene. Thus, in an embodiment, an individual in need of treatment may be administered an effective amount of an inhibitor or inhibitors of one or more of SHP2 and EGFR. The inhibitors of one or more of SHP2 and EGFR may be administered simultaneously or sequentially, overlapping, or completely independently, or alone. If administered in conjunction, the SHP2 inhibitor may be administered first, and the EGFR inhibitor may be administered later in additional to the SHP2 inhibitor, or vice versa.

LUSC may be diagnosed by any one of several tests. For instance, lung imaging such as CT or MRI can be used. A lung biopsy may be used to confirm the cytopathology and histopathology of the squamous carcinoma features. A molecular test may be used to determine mutations in the lung cancer.

LUSC cells (e.g., cells obtained from LUSC tumors) may be tested for the presence of KMT2D mutation. The testing can be carried out on any biological sample, including sections of tissues such as biopsy samples and frozen sections prepared from tissues taken for histologic purposes. Samples may include tumor tissue samples, blood and blood fractions (e.g., serum, platelets, red blood cells, and the like), sputum, bronchoalveolar lavage, cultured cells, e.g., primary cultures, explants, and transformed cells, stool, urine, and the like. A biological sample is typically obtained from a mammal, such as a human, but may be obtained from a farm animal or a domesticated animal. A biopsy may be obtained by standard techniques including, excisional biopsy, incisional biopsy, needle biopsy, surgical biopsy, and bone marrow biopsy. Biopsy techniques are described in in Harrison's Principles of Internal Medicine, Kasper, et al., eds., 16th ed., 2005).

In an embodiment, this disclosure provides a method for treating LUSC in an individual by administration to the individual of a therapeutically effective amount of inhibitor or inhibitors of one or more of RTK-Ras signaling pathway. In an embodiment, the LUSC cells may also carry a KMT2D mutation (e.g., loss-of-function or truncated KMT2D mutation).

Many SHP2 inhibitors are known in the art. These include the SHP2 inhibitors disclosed in PCT/IB2015/050345 (published as WO2015107495), PCT/IB2015050344 (published as WO2015107495), PCT/IB2015/050343 (published as WO2015107493), US publication no. 20170342078, Xie et al., (J. Medicinal Chem., DOI: 10.1021/acs.jmedchem.7b01520, November 2017), LaRochelle et al., (25(24): 6479-6485, 2017). The listing and descriptions of SHP2 inhibitors from these published applications and publications are incorporated herein by reference. Examples of SHP2 inhibitors include, but are not limited to, TNO155, 1-(4-(6-bromonaphthalen-2-yl)thiazol-2-yl)-4-methylpiperidin amine, and chemical compounds having a benzothiazolopyrimidones scaffold, NSC-117199, NSC-87877, SPI-112, SPI-112Me, Fumosorinone, demethylincisterol $A_3$, 11a-1, and Cryptotanshinone, RMC-3943, RMC-4550, SHP099, NSC-87877. Expression of the gene PTPN11 encoding SHP2 can also be inhibited by the use of inhibitory RNAs, such as siRNA, shRNA, CRISPR/Cas9 or other gene expression disrupters. Generally, an amount of from 1 µg/kg to 100 mg/kg and all values therebetween may be used.

Examples of EGFR inhibitors useful for the present methods include, but are not limited to, erlotinib, gefitinib, afatinib, cetuximab, panitumumab, necitumumab, PF-00299804, nimotuzumab, R05083945, and dacomitinib, or combinations thereof. Generally, an amount of from 1 µg/kg to 100 mg/kg and all values therebetween may be used.

In embodiments, the present method may comprise administration of SHP2 and/or EGFR inhibitors in combination with immune based therapies. Immune based therapies that may be used in the combination therapy (e.g., in combination with SHP2 and/or EGFR inhibitors), include immune checkpoint inhibitors (e.g., anti-PD-1, anti-PD-L1, anti-CTLA-4, etc.), which may be small molecule inhibitors or monoclonal antibodies, vaccines (e.g., dendritic cell-based; viral-based; autologous whole tumor cell), adoptive cellular therapy (e.g., TILs; T cell receptor-engineered lymphocytes; CART cells or CAR NK cells) and immune system modulators.

Generally, a therapeutically effective amount of an antibody, small molecules, or other compounds or compositions described herein can be in the range of 0.01 mg/kg to 100 mg/kg and all values therebetween. For example, the dosage can be 0.1 mg/kg to 100 mg/kg, 0.1 mg/kg to 50 mg/kg etc. The SHP2 and EGFR inhibitor(s) and the immune therapy (e.g., checkpoint inhibitor) may be administered in separate compositions or in the same composition, via the same route or separate routes, over a same period of time or different periods of time. The two administrations regimens may overlap partially or completely or not at all. The compositions may comprise a pharmaceutically acceptable carrier or excipient, which typically does not produce an adverse, allergic or undesirable reaction when administered to an individual, such as a human subject. Pharmaceutically acceptable carrier or excipient may be fillers (solids, liquids, semi-solids), diluents, encapsulating materials and the like. Examples include, but are not limited to, saline, buffered saline, dextrose, water, glycerol, ethanol, etc.

The pharmaceutical compositions may be in the form of solutions, suspensions, emulsions, and solid injectable compositions that are dissolved or suspended in a solvent immediately before use. The injections may be prepared by dissolving, suspending or emulsifying one or more of the active ingredients in a diluent. Examples of diluents are distilled water for injection, physiological saline, physiologic buffer, vegetable oil, alcohol, and a combination thereof. Further, the compositions may contain stabilizers, solubilizers, suspending agents, emulsifiers, soothing agents, buffers, preservatives, etc. The pharmaceutical compositions may be formulated into a sterile solid or powdered preparation, for example, by freeze-drying, and may be used after sterilized or dissolved in sterile injectable water or other sterile diluent(s) immediately before use. The compositions can include one or more standard pharmaceutically acceptable carriers. Some examples herein of pharmaceutically acceptable carriers can be found in: *Remington: The Science and Practice of Pharmacy* (2013) 22nd Edition, Pharmaceutical Press.

The pharmaceutical compositions of the invention may be administered via any route that is appropriate, including but not limited to oral, parenteral, sublingual, transdermal, rectal, transmucosal, topical, via inhalation, via buccal administration, or combinations thereof. Parenteral administration includes, but is not limited to, intravenous, intraarterial, intraperitoneal, subcutaneous, intratumoral, intramuscular, intrathecal, and intraarticular. The agents(s) can also be administered in the form of an implant, which allows a slow release of the compound(s), as well as a slow controlled i.v. infusion. The SHP2 and EGFR inhibitors and the immune therapy may be delivered via different routes or the same route.

Individuals who may receive the combination treatment described herein include those afflicted with or diagnosed with a LUSC in which the cells have activated RTK-Ras signaling pathway, or have activated RTK-Ras signaling pathway and carry a mutation in KMT2D (such as a loss-of-function or truncated mutation).

In an embodiment, the present methods may be combined with other modalities of treatment, such as, surgery, radiation and the like. The present inhibitors may also be used in combination with other therapies, including chemotherapy, for the treatment of LUSC.

In an aspect, this disclosure provides kits for the treatment of cancer. The kit may comprise in a single or separate compositions: i) one or more of SHP2 and EGFR inhibitors, and, optionally, one or more immune checkpoint inhibitors. Buffers and instructions for administration may also be provided.

The following examples are provided to illustrate the invention and are not intended to be restrictive.

Example 1

Methods
Organoid Culture and Manipulation

Trp53$^{L/L}$ basal cell lung organoids were generated from 8-10 weeks Trp53$^{L/L}$ mice of the C57BL/6J background. In brief, the trachea and main bronchi were dissected from mouse and washed 2 times with PBS. The tissues were minced by scissors and then digested in collagenase D and DNase I in Hank's Balanced Salt Solution (HBSS) at 37° C. for 30 minutes. After incubation, the digested tissue was passed through a 70 μm cell strainer to obtain single-cell suspensions. After spinning down for 350 g 5 min, cells were resuspended in organoid media (DMEM/F-12 with 15 mM HEPES (StemCell Technologies, 36254) supplemented with GlutaMAX™ Supplement (Gibco, 35050061), 1× Antibiotic-Antimycotic (Gibco, 15240062), N2 Supplement (Gibco, 17502048), B27 supplement (Gibco, A1895601), 1 mmol/L N-Acetylcysteine (Thermo Scientific™, A15409.14), 50 ng/mL human recombinant EGF (Sigma-Aldrich, E9644), and 3% conditioned media from L-WRN cells containing Wnt3a, Noggin, and R-spondin). Using a 1:2 ratio of organoid media and growth factor reduced basement membrane matrix (Matrigel, Corning, 354230), lung epithelial organoids were maintained for successive passages.

To generate lentivirus, HEK-293T cells were co-transfected with lentiviral plasmids, packaging plasmids psPAX2 (Addgene #12260) and pMD2.G (Addgene #12259) using Lipofectamine 3000 (Invitrogen, L3000008) according to the manufacturer's instructions. Viral particles in the cell culture supernatant were filtered with 0.45-μm filters (Corning, 431225) to remove cellular debris.

Trp53$^{-/-}$ organoids were generated from Trp531$^{L/L}$ organoids by Ad-Cre-GFP virus infection, followed by flow cytometry sorting of GFP$^+$ cells. To generate Trp53$^{-/-}$; Kmt2d$^{-/-}$ and Trp53$^{-/-}$; Pten$^{-/-}$ organoids, CRISPR was performed using LentiCRISPRv2 vector obtained from Addgene. Guide RNAs (gRNA) against mouse Kmt2d and Pten were cloned into lentiCRISPRv2. Lentivirus was generated by transfection of HEK-293T cells with lentiCRISPRv2 (sgKmt2d or sgPten) and the packaging plasmids psPAX2 (Addgene #12260) and pMD2.G (Addgene #12259) using Lipofectamine 3000 (Invitrogen, L3000008). CRISPR guides and sequencing primers are listed in Table 1. Organoids were isolated by digesting the Matrigel with 0.25% trypsin-EDTA in culture plates for 5-10 minutes at 37° C. and washed twice with PBS. Once organoids were dissociated, cells were pelleted and resuspended in 250 μL lentiviral solution. Spinoculation was performed by transferring the suspension onto a 24-well plate and centrifuging the plate at 600 g for 1 hour at 32° C. Plates were then incubated at 37° C. for 6 hours before washing the suspension with fresh media and pelleting the cells to be embedded in fresh Matrigel media mixture. Antibiotic (blasticidin, 5 μg/ml) was added to the media to select the infected organoids.

Cell Lines

To generate the syngeneic mouse LUSC Trp53$^{-/-}$; Kmt2d$^{-/-}$, Trp53$^{-/-}$; Pten$^{-/-}$ and Trp53$^{-/-}$; Pten$^{-/-}$; Kmt2d$^{-/-}$ cell lines. Subcutaneous Trp53$^{-/-}$; Kmt2d$^{-/-}$, Trp53$^{-/-}$; Pten$^{-/-}$ and Trp53$^{-/-}$; Pten$^{-/-}$; Kmt2d$^{-/-}$ tumors were harvested and washed twice in 1× PBS, and then the tumors were cut into small pieces using scissors. The shredded tissues were cultured in an incubator at 37° C. (with 5% CO2) with Advanced DMEM (Thermo Fisher Scientific) supplemented with 10% Fetal Bovine Serum (FBS, Sigma-Aldrich), GlutaMAX™ Supplement (Gibco, 35050061) and 1× Antibiotic-Antimycotic (Gibco, 15240062). Fresh medium was changed every other day. The cells were cultured for at least five passages to establish the stable cell lines. To generate the Trp53$^{-/-}$; Kmt2d$^{-/-}$ sgControl and Trp53$^{-/-}$; Kmt2d$^{-/-}$ sgSHP2 cell lines, Trp53$^{-/-}$; Kmt2d$^{-/-}$ cells was transfected with pX458-sgCtrl and pX458-sgSHP2 (Fedele et al., 2021) followed by flow cytometry sorting of GFP$^+$ cells.

Human LUSC cell lines (HARA, HCC95, EBC1, and LK2) were maintained in Advanced DMEM (Thermo Fisher Scientific) supplemented with 10% Fetal Bovine Serum (FBS, Sigma-Aldrich), GlutaMAX™ Supplement (Gibco, 35050061) and 1× Antibiotic-Antimycotic (Gibco, 15240062). HEK-293T cells were cultured in Dulbecco's Modified Eagle Medium (Gibco), 10% fetal bovine serum (FBS) and 1× Antibiotic-Antimycotic (Gibco, 15240062). All cell lines used in this study were tested as Mycoplasma-negative using the Universal Mycoplasma Detection Kit (ATCC 30-1012K).

To knock out KMT2D in human LUSC cells, HARA, EBC1 and HCC95 cells were first infected with Cas9 expressing lentivirus (lentiCas9-Blast, Addgene #52962). The HARA-Cas9 cells were then infected with lentivirus targeting human KMT2D (lentiviral vector purchased from Vector builder). KMT2D mutations were confirmed by sequencing. CRISPR guides and sequencing primers were listed in Table 1.

TABLE 1

RT-qPCR Primer Sequences

| Target genes | Primer labels | Sequence (5'→3') |
|---|---|---|
| mouse Ptprb | mPtprb-F | ATCCTCGTCCTGACCATCAGTG (SEQ ID NO: 1) |
|  | mPtprb-R | GCTCCAGGTTACCATCAGCCTA (SEQ ID NO: 2) |
| mouse Ptprf | mPtprf-F | CAGATTCGTGGCTACCAGGTCA (SEQ ID NO: 3) |
|  | mPtprf-R | ACGGTGATGGAGTAGGTGGTCT (SEQ ID NO: 4) |
| mouse Ptprs | mPtprs-F | TACCAGGTCCACTATGTGCGCA (SEQ ID NO: 5) |
|  | mPtprs-R | AGTCTCAGGCTGGAGGTTCGTT (SEQ ID NO: 6) |
| mouse Ptpru | mPtpru-F | GAACTGCATCCGAATTGCCAGG (SEQ ID NO: 7) |
|  | mPtpru-R | AATGAGGACGGCAAGACCACCT (SEQ ID NO: 8) |
| mouse Actb | mActb-F | CATTGCTGACAGGATGCAGAAGG (SEQ ID NO: 9) |
|  | mActb-R | TGCTGGAAGGTGGACAGTGAGG (SEQ ID NO: 10) |

TABLE 1-continued

RT-qPCR Primer Sequences

| Target genes | Primer labels | Sequence (5'→3') |
|---|---|---|
| human PTPRB | hPTPRB-F | TCTTCCCGACAAGTGGTTGTGG (SEQ ID NO: 11) |
| | hPTPRB-R | AGCCAGGAAACGCTGAGGTAGT (SEQ ID NO: 12) |
| human PTPRF | hPTPRF-F | ATGTCATCGCCTACGACCACTC (SEQ ID NO: 13) |
| | hPTPRF-R | GTGGCGATGTAGGCATTCTGCT (SEQ ID NO: 14) |
| human PTPRS | hPTPRS-F | CTCGCCCAAGAACTTCAAGGTG (SEQ ID NO: 15) |
| | hPTPRS-R | AGGTGCGTGATGAGCTTCTTGG (SEQ ID NO: 16) |
| human PTPRU | hPTPRU-F | ACAACCAGACCTACCGAGGCTT (SEQ ID NO: 17) |
| | hPTPRB-R | CTTTCCTGGCAATGCGGATGCA (SEQ ID NO: 18) |
| human ACTB | hACTB-F | CACCATTGGCAATGAGCGGTTC (SEQ ID NO: 19) |
| | hACTB-R | AGGTCTTTGCGGATGTCCACGT (SEQ ID NO: 20) |

To knockdown Ptprb, Ptprf, Ptprs and Ptpru in mouse Kmt2d WT cells, shRNA vectors were obtained from Sigma MISSION TRC shRNA library with clone ID as follows: shPtprb (mouse) TRCN0000029926, shPtprf-1 (mouse) TRCN0000029944, shPtprf-2 (mouse) TRCN0000029948, shPtprs-1 (mouse) TRCN0000238010, shPtprf-2 (mouse) TRCN0000257330, shPtpru-1 (mouse) TRCN0000029964 and shPtpru-2 (mouse) TRCN0000029968. Stable cell lines with Ptprb, Ptprf, Ptprs and Ptpru knockdown were generated using the s were generated using the lentiviral packaging system described above.

Western Blot

Cells were lysed in RIPA buffer (Thermo Scientific™, 89900) containing protease/phosphatase inhibitor cocktail (Thermo Scientific™, 78440). Protein concentration was measured using the Pierce™ BCA assay (Thermo Scientific™, 23225). Equivalent amounts of each sample were loaded on 4% to 12% Bis-Tris gels (Bio-Rad), transferred to nitrocellulose membranes, and immunoblotted with antibodies directed against KMT2D (C15310100, Diagenode), EGFR (CST, 2232S), pEGFR (CST, 3777S), ERBB2 (CST, 2165S), pERBB2 (CST, 2243S) and β-actin (A5441, Sigma). IRDye 800-labeled goat anti-rabbit IgG (LI-COR, 926-32211) and IRDye 680-labeled goat anti-mouse IgG (LI-COR, 926-68070) secondary antibodies, and membranes were detected with an Odyssey detection system (LI-COR Biosciences).

Phospho-RTK Array

The Mouse Phospho-RTK Array Kit (R&D Systems, ARY014) was used to determine the relative levels of tyrosine phosphorylation of 39 distinct receptor tyrosine kinase (RTK) in organoids, cell lines and tumor nodules, according to the manufacturer's protocol. Chemiluminescent signals were captured with a Chemidoc MP Imaging System (Bio-Rad Laboratories) and images were analyzed using Image Studio Lite (LI-COR Biosciences).

Cell Viability Assay

Cells were seeded in 96-well plates (1000-2000 cells/well) in media and treated with SHP099 or afatinib at indicated concentrations and time points. Cell viability was measured using the MTS-based CCK-8 assay (Dojindo, #CK04). Absorption at 450 nm was measured 3 hours after addition of CCK-8 reagent to cells using FlexStation 3 multi-mode microplate reader according to the manufacturer's instructions.

Colony Formation Assay

Cells were trypsinized to produce a single-cell suspension. 2,000 cells were counted and plated in each well of a 6-well plate. Medium was changed every 2 days. After 7 days, cells were fixed with 70% ethanol for 10 minutes, and the cells were stained with 0.5% crystal violet (dissolved in 20% methanol) for 5 minutes and washed. Photos were taken and quantified using ImageJ.

Animal Studies

All mouse work was reviewed and approved by the Institutional Animal Care and Use Committee at NYU School of Medicine and the Center for Excellence in Molecular Cell Science, Chinese Academy of Sciences. To study whether mutated organoids can form LUSC in vivo, 6 to 8-week-old C57BL/6J mice were obtained from Jackson Laboratory and subcutaneously inoculated with organoids into both flanks. Tumor length and width were measured using calipers. Tumor volumes were calculated using the formula (Length×Width$^2$)/2. To establish the orthotopic LUSC model, Trp53$^{-/-}$; Kmt2d$^{-/-}$ or Trp53$^{-/-}$ Pten$^{-/-}$ cells were injected into B6(Cg)-Tyrc-2J/J (B6-albino) mice via tail vein injection at 2×10$^6$ cells per mice. Mill was used to monitor tumor formation and progression of LUSC. After confirming the tumor burden by MRI, mice were randomized and then treated with vehicle, chemotherapy (Carboplatin 40 mpk I.P. QW+paclitaxel 10 mpk I.P. QW), SHP099 (75 mpk, 5 days per week), afatinib (10 mpk, 5 days per week) or the combination of SHP099 and afatinib. Subsequent Mill was performed every 2 weeks after treatment initiation and survival of animals were monitored. To compare the in vivo treatment efficacy of Trp53$^{-/-}$; Pten$^{-/-}$ and Trp53$^{-/-}$; Pten$^{-/-}$; Kmt2d$^{-/-}$ LUSC, Trp53$^{-/-}$; Pten$^{-/-}$ cells (4×10$^6$) and Trp53$^{-/-}$; Pten$^{-/-}$; Kmt2d$^{-/-}$ cells (4×10$^6$) were injected with 1:1 mixture of cell suspension and Matrigel (Corning 354234) subcutaneously into both flanks of C57BL/6J mice. When the tumor volume reached approximately 100-200 mm$^3$, the animals were randomized into treatment groups and dosing was initiated on day 0 with vehicle or combined SHP099 (75 mpk, 5 days per week) and afatinib (10 mpk, 5 days per week). Tumor size and body weight were measured twice weekly, and the tumor volumes were calculated using the (Length×Width$^2$)/2).

For human patient-derived xenograft (PDX) xenograft study. PDX-1 (KMT2D mutant), PDX-2 (KMT2D WT), PDX-3 (KMT2D mutant), PDX-4 (KMT2D WT) derived from primary LUSC tumor fragments were implanted subcutaneously in a single flank of 6-8-week-old female NOD-SCID-Il2rg$^{null}$ (NSG) mice (Jackson Laboratory). For human cell line xenograft study, LK2 cells (1×10$^6$), HARA-sgControl (2×10$^6$) and HARA-sgKMT2D (2×10$^6$) were injected with 1:1 mixture of cell suspension and Matrigel (Corning 354234) subcutaneously into both flanks of nude mice (Jackson Laboratory). For PDXs and human cell line xenograft study, when the tumor volume reached approximately 100-200 mm$^3$, the animals were randomized into treatment groups and dosing was initiated on day 0 with vehicle, SHP099 (75 mpk, 5 days per week), afatinib (10 mpk, 5 days per week) or the combination of SHP099 and afatinib. Tumor size and body weight were measured twice weekly, and the tumor volumes were calculated using the (Length×Width$^2$)/2).

MRI Quantification

Animals were anesthetized with isoflurane to perform MRI of the lung field using BioSpec USR70/30 horizontal bore system (Bruker) to scan 16 consecutive sections. Tumor volumes within the whole lung were quantified using 3-D slicer software to reconstruct MRI volumetric measurements. Acquisition of the MRI signal was adapted according to cardiac and respiratory cycles to minimize motion effects during imaging.

Histology and Immunohistochemistry

Lungs were perfused with 10% formalin, stored in fixative for 48 h, and embedded in paraffin. 4 μm thick sections of formalin fixed tissue were used for immunoperoxidase analysis after baking at 60° C. for 1 hour, deparaffinization and rehydration (100% xylene X4 for 3 minutes each, 100% ethanol X4 for 3 minutes each and running water for 5 minutes). The sections were blocked for peroxidase activity with 3% hydrogen peroxide in methanol for 10 minutes and washed under the running water for 5 minutes. The sections with pressure cooked (Biocare Medical) antigen retrieval were at 120° C. in Citrate Buffer (Dako Target Retrieval Solution, S1699). The slides were cooled for 15 minutes and transferred to Tris buffer saline (TBS). The sections were incubated with P40 (ΔNp63), TTF1, CK5 Ki-67, cleaved caspase 3, or KMT2D antibody for 40 min at room temperature. The secondary antibody was used Leica Novolink Polymer (Cat #RE7161) 30 min incubation. All the incubations were carried out in a humid chamber at room temperature. The slides were rinsed with TBS in between incubation. The sections were developed using 3,3'-diaminobenzidine (DAB) as substrate and counter-stained with Mayer's Hematoxylin. IHC images were analyzed and quantified by FIJI (NIH).

Immunofluorescence Staining and Imaging

Organoids were fixed in 4% paraformaldehyde (Diluted the 32% paraformaldehyde in PBS, Electron Microscopy Sciences 15714) for 10 min at room temperature. Cells were washed three times for 5 min with 200 mM glycine containing PBS, followed by permeabilization with 0.2% Triton X-100 in PBS for 15 min. After blocking with 5% bovine serum albumin (BSA) in PBS for 1 hour, cells were incubated with primary antibody NGFR (abcam, ab8875) and Ki-67 (14-5698-82, Thermo Fisher Scientific) diluted in a 5% BSA in PBS solution overnight at 4° C. After washing four times with PBS, cells were incubated with secondary antibodies Alexa Fluor Plus 555 (Invitrogen A-21428, 1:500) and Alexa Fluor Plus 488 (Invitrogen A-11006) and for 1 hour and washed three times with PBS. Cell nuclei were counterstained with DAPI (BioLengend 422801, diluted to 600 nM in PBS) for 5 min. Cells were washed two more times in PBS before mounting with Fluorescence Mounting Medium (Dako, S3023). Images were acquired using Zeiss 880 Laser Scanning Confocal Microscope and were processed and analyzed by FIJI (NIH).

RNA Extraction and RT-qPCR

Cell pellets were collected and then subjected to total RNA extraction using RNeasy Plus Mini Kit (QIAGEN, 74136) according to the manufacturer's instructions. The extracted RNA was reversely transcribed into cDNA using the High-Capacity RNA-to-cDNA™ Kit (Thermo Fisher Scientific, 4387406) according to the manufacturer's instructions. The obtained cDNA samples were diluted and used for RT-qPCR using PowerUp™ SYBR™ Green Master Mix (Thermo Fisher Scientific, A25742). Gene specific primers with sequences listed in Table 2 were used for PCR amplification and detection on the QuantStudio 3 Real-Time PCR System (Applied Biosystems). RT-qPCR data were normalized to Actb (mouse cells) or ACTB (human cells) and presented as fold changes of gene expression in the test sample compared to the control.

TABLE 2

CRISPR/Cas9 guides and sequencing primers sgRNA sequences

| Target gene | Name | Guide sequence | Species |
|---|---|---|---|
| Kmt2d | sgKmt2d-1 | GAGGTCTCCGTCCCCGGTTC (SEQ ID NO: 21) | Mouse |
| | sgKmt2d-2 | CAGAGAGCACAACGCCGTGC (SEQ ID NO: 22) | Mouse |
| Pten | sgPten | GCTAACGATCTCTTTGATGA (SEQ ID NO: 23) | Mouse |
| KMT2D | sghKMT2D-1 | AACCGACGGAGGGCGTAGTG (SEQ ID NO: 24) | Human |
| | sghKMT2D-2 | GGGGATAGGCGCGATACCTC (SEQ ID NO: 25) | Human |

PCR sequencing primers

| Target gene | Name | Primer sequence | Species |
|---|---|---|---|
| Kmt2d locus | KMT2D-F1 | CCGCCTGCTGAAGATAAAGA (SEQ ID NO: 26) | Mouse |
| | KMT2D-R1 | GGTGGGATGAGATAAACAGAGG (SEQ ID NO: 27) | Mouse |
| | KMT2D-F2 | AAATCCTGGCTTTGTCTGAAATG (SEQ ID NO: 28) | Mouse |
| | KMT2D-R2 | GGTTAACACTGTGACCGGTAG (SEQ ID NO: 29) | Mouse |

TABLE 2-continued

CRISPR/Cas9 guides and sequencing primers

| KMT2D locus | KMT2D-F3 | GGAGTCTCCTCTGTCTCC (SEQ ID NO: 30) | Human |
|---|---|---|---|
| | KMT2D-R3 | GTGTGATTCCTCAGGTTGG (SEQ ID NO: 31) | Human |
| | KMT2D-F4 | TCTCCACCGGAAGAGTCA (SEQ ID NO: 32) | Human |
| | KMT2D-R4 | GGACAGGTGCAATTCCTCA (SEQ ID NO: 33) | Human |
| | KMT2D-F6 | CTTTAAGGCTGGGTCTCTAGC (SEQ ID NO: 34) | Human |
| | KMT2D-R6 | GACAAGGTAGATGAAGGTGGAG (SEQ ID NO: 35) | Human |
| | KMT2D-F7 | GGGTCTCTAGCCCACACTT (SEQ ID NO: 36) | Human |
| | KMT2D-R7 | GGTGGAGCAACCTTCAATATCC (SEQ ID NO: 37) | Human |

RNA Extraction and Bulk-RNA Sequencing Analysis

Tumor nodules or cell pellets were subjected to total RNA extraction using RNeasy Plus Mini Kit (QIAGEN, cat #74136) according to the manufacturer's instructions. Read qualities were evaluated using FASTQC (Babraham Institute) and mapping to mm10 reference genome using STAR program 34, with default parameters. Read counts, TPM and FPKM were calculated using RSEM program 35. Identification of differentially expressed genes was performed using DESeq2 in R/Bioconductor (R version 4.0.4). Genes with false discovery rate (FDR) lower than 0.05 were considered significantly differentially expressed.

All plots were generated using customized R scripts. Pathway enrichment analysis was performed on all genes ranked from high to low DESeq2 estimated fold-change using the GSEAPreRanked function with enrichment statistic classic and 1000 permutations using GSEA program (Subramanian et al., 2005). Gene sets (Hallmark and C6) were downloaded from MsigDB 37. Differential expression genes involved in top enriched pathways were selected to generate heatmaps using pheatmap R function with default hierarchical clustering method for gene orders. Dot plots of enriched pathways, heat maps of genes, and volcano plots were generated using the pheatmap, ggplot2, and EnhancedVolcano in R (version 4.0.4).

Comparing LUSC, LUAD and Normal Lung Gene Expression

Raw gene expression tables of normal (Mollaoglu et al., 2018) and LUAD (KP) (Deng et al., 2021) were downloaded from gene expression omnibus (GEO) and combined with LUSC for differential expression analysis using DESeq2 as described in above. Differential expression genes for each condition were identified by comparing all samples from one condition to the rest samples. Top differential expression genes with highest log 2 fold changes were selected to generate heatmap using pheatmap R package, which was also used for generating targeted gene heatmaps.

Human LUSC Analysis

RNA-seq raw counts for TCGA LUSC dataset were downloaded from Genomic Data Commons (GDC) Data Portal (https://portal.gdc.cancer.gov). 249 LUSC samples with high KMT2D expression were compared with 246 LUSC samples with low KMT2D expression using DESeq2. Pathway enrichment analysis was performed on all genes ranked from high to low DESeq2 estimated fold-change using the GSEAPreRanked function with enrichment statistic classic and 1000 permutations using GSEA program.

Oncoprint and gene expression correlation data were obtained and analyzed using cBioportal for cancer genomics database (http://www.cbioportal.org) (Cerami et al., 2012; Gao et al., 2013).

Expression of KMT2D mRNA in LUSC tumor and normal tissues was analyzed using the online tool, GEPIA2 (http://gepia2.cancer-pku.cn/) (Tang et al., 2019). The phospho-EGFR in LUSC tumor and normal tissues data was obtained and analyzed from (Satpathy et al., 2021).

Expression of KMT2D mRNA, phospho-EGFR, and drug sensitivity to afatinib, neratinib, lapatinib and poziotinib in human LUSC cell lines were obtained and analyzed using DepMap (https://depmap.org/portal/).

ATAC-Seq and Analysis

Freshly harvested cells were directly sent to NYU Langone Health Genome Technology Center for library construction and sequencing. The library was constructed with Nextera DNA library Prep Kit (cat. #FC-121-1030, Illumina) according to the manufacturer's instructions and was sequenced by Illumina NovaSeq 6000.

Illumina sequencing adapter was removed using Trimgalore/0.5.0 from raw sequence files in fastq format. The reads were aligned to the mm10 reference genome using Bowtie2/2.4.1 (Langmead and Salzberg, 2012) with default parameters. The aligned reads were used after removing PCR duplicates using SAMtools and filtered off an ATAC blacklist (Buenrostro et al., 2013) for mitochondrial DNA and homologous sequences. Both fragment ends were shifted +4 nt for positive strand and −5 nt for negative strand to account for the distance from Tn5 binding and helicase activity to identify cut sites. Extended Tn5 cut sites were used for peak calling with MACS2 with parameters—nomodel—extsize 100—shift 50—nolambda—keep-dup all. The gained/lost peaks comparing Kmt2d KO versus Kmt2d WT cells were identified using R package DiffBind with cutoffs of a false discovery rate (FDR) ≤0.05. Normalized ATAC-seq as RPKM signals for each sample were visualized on Integrative Genome Viewer genome browser (Robinson et al., 2011). Average signal plots were generated using plotProfile from deeptools/3.2.1 (Ramirez et al., 2016).

ChIP-seq, CUT&tag and Analysis

For H3K27ac chromatin immunoprecipitation (ChIP), cells were crosslinked with 1% formaldehyde in PBS for 10 minutes at room temperature, washed in 5 mg/mL BSA in PBS and then in just cold PBS, resuspended in lysis buffer [50 mmol/L Tris-HCl pH 8.1, 10 mmol/L EDTA, 1% SDS, 1× protease inhibitor cocktail (Thermo Fisher Scientific)] and sonicated by the Diagenode Bioruptor Sonication System. Fragmented chromatin was diluted in immunoprecipitation buffer (20 mmol/L Tris-HCl pH 8.1, 150 mmol/L NaCl, 2 mmol/L EDTA, 1% Triton X-100) and incubated overnight at 4° C. with protein G magnetic beads (Dynabeads, Thermo Fisher Scientific) that had been preincubated with anti-H3K27ac (Abcam, ab4729). Immunoprecipitates were washed six times with the wash buffer (50 mmol/L HEPES pH 7.6, 0.5 mol/L LiCl, 1 mmol/L EDTA, 0.7% sodium deoxycholate, 1% IGEPAL CA-630) and twice with Tris-EDTA buffer. Immunoprecipitated DNA was treated with RNase A and Proteinase K on the beads, recovered in 1% SDS and 0.1 mol/L NaHCO3 over a period of 6 hours at 65° C., and purified with DNA clean and concentrator-25 (Zymo Research). The DNA was sent to NYU School of Medicine Genome Technology Center for library construction and sequencing. The library was constructed with KAPA Hyper-Prep Kits (cat. #07962347001, Roche) according to the manufacturer's instructions and was sequenced by Illumina NovaSeq 6000.

CUT&Tag profiling was performed using CUT&Tag-IT™ Assay Kit (Active Motif, cat #53160) according to the manufacturer's instructions and the library was sent to NYU School of Medicine Genome Technology Center for sequencing by Illumina NovaSeq 6000.

The sequencing reads were aligned to the mm10 reference genome using Bowtie2 (Langmead and Salzberg, 2012). Samtools (Li et al., 2009) was used to sort and index the aligned reads, and MACS2 (Zhang et al., 2008) was used to calculate signal per million reads (SPMR) and to call significant ChIP-seq peaks (q value<0.05) in Kmt2d KO and Kmt2d WT cells. MAnorm (Shao et al., 2012) was used to identify differential peaks between Kmt2d KO and Kmt2d WT cells. Heatmap of peaks and average signal plots were generated by Deeptools (Ramirez et al., 2016). To study the relationship between Kmt2d loss-affected H3K27ac peaks and gene expression changes, Binding and expression target analysis (BETA) package (Wang et al., 2013) was used by combining H3K27ac ChIP-seq and RNA-seq results.

Illustration Tool

The graphical abstract image is created with BioRender.

Statistical Analysis

Statistical analyses were performed using GraphPad Prism 9 software and statistical significance was determined by p<0.05. Data are presented as mean with SEM unless otherwise specified. Statistical comparisons were performed using unpaired Student t test for two-tailed P values unless otherwise specified (*P<0.05, P<0.01, *P<0.001, ****P<0.0001).

The following Examples describe results obtained using the materials and methods described in Example 1.

Example 2

Kmt2d Deletion Promotes Lung Organoids Transformation

Figure 1:
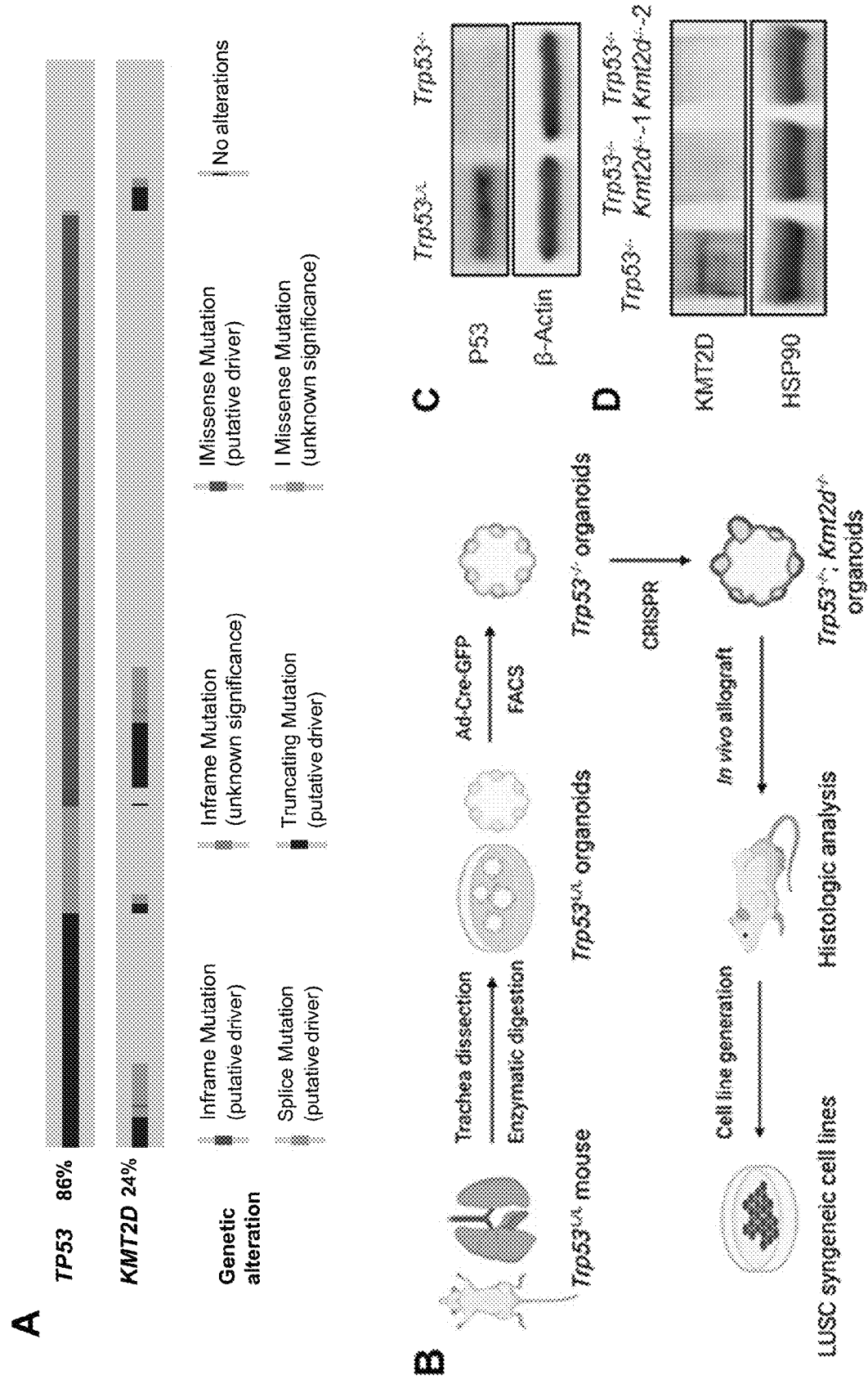
FIG. 1. KMT2D deletion promotes lung organoids transformation. (A) OncoPrint showing frequency of KMT2D mutations and their co-occurrence with TP53 mutations in human LUSC database (TCGA, PanCancer Atlas, n=487). (B) Schematic illustration of the workflow for establishing tumorigenic organoids and syngeneic cell lines from parental Trp53L/L lung basal cell organoids. (C) Western blot confirmation of P53 loss in the Trp53–/– organoids, β-Actin was used as a loading control. Trp53–/– organoids were generated from Trp53L/L organoids by Ad-Cre-GFP virus infection, followed by flow cytometry sorting of GFP+ cells. (D) Western blot confirmation of KMT2D loss in the Trp53–/–; Kmt2d–/– organoids, HSP90 was used as a loading control. (E) Representative hematoxylin and eosin (H&E) staining, and immunohistochemistry (IHC) staining of ΔNp63 in organoids with indicated genotypes. Scale bars, 100 μm. (F) Representative brightfield microscopy images and immunofluorescence staining of organoids after 7 days of culture. Scale bars, 100 μm. Organoids were stained with DAPI (blue), NGFR (red) and Ki-67 (green). (G) Quantifications of the diameter and relative Ki-67 intensity of organoids with indicated genotypes. Data shown as means±SEM. p<0.01, *p<0.001, **p<0.0001, NS, not significant (unpaired two-tailed t test). (H) Tumor volume quantifications after 6-weeks of implanting organoids into C57BL/6J mice. Data shown as means±SEM. **p<0.0001 (unpaired two-tailed t test). (I) (Left) Representative images of subcutaneous tumors from implanted organoids with indicated genotypes. The red circles indicate the tumors. (Right) Representative H&E staining and IHC staining of KRT5 and ΔNp63 in tumors derived from Trp53–/–; Kmt2d–/– and Trp53–/–; Pten–/– organoids.
Figure 1:
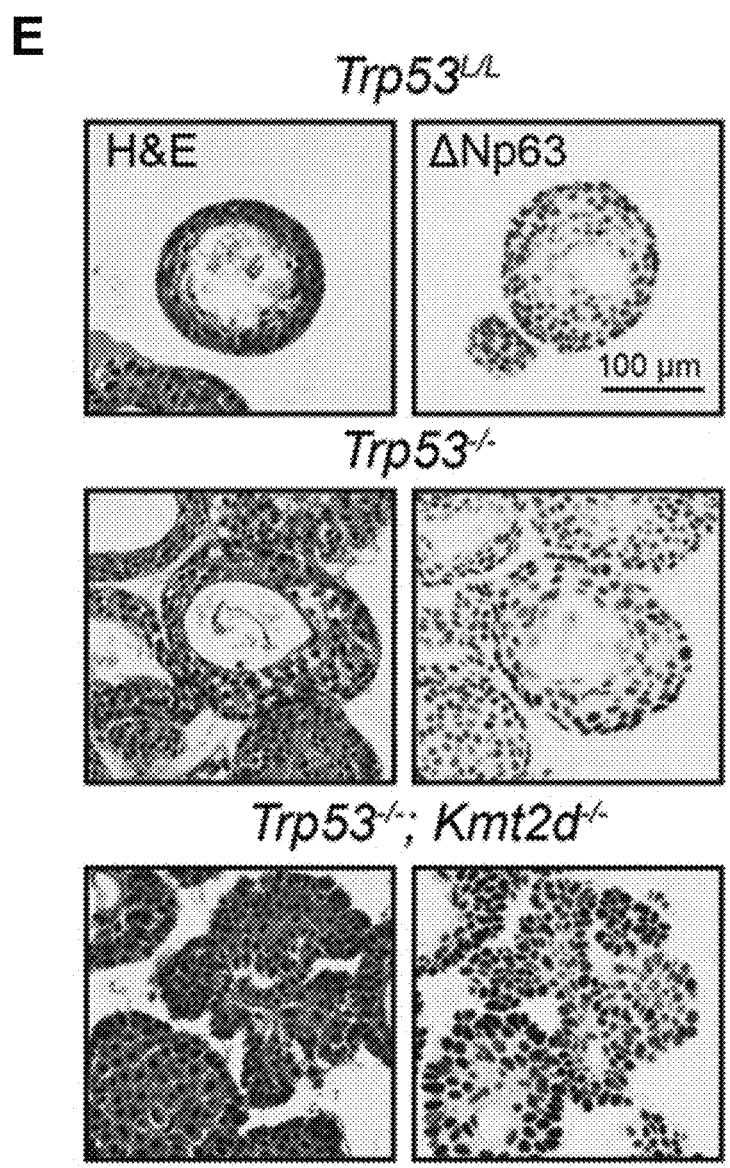
Figure 1:
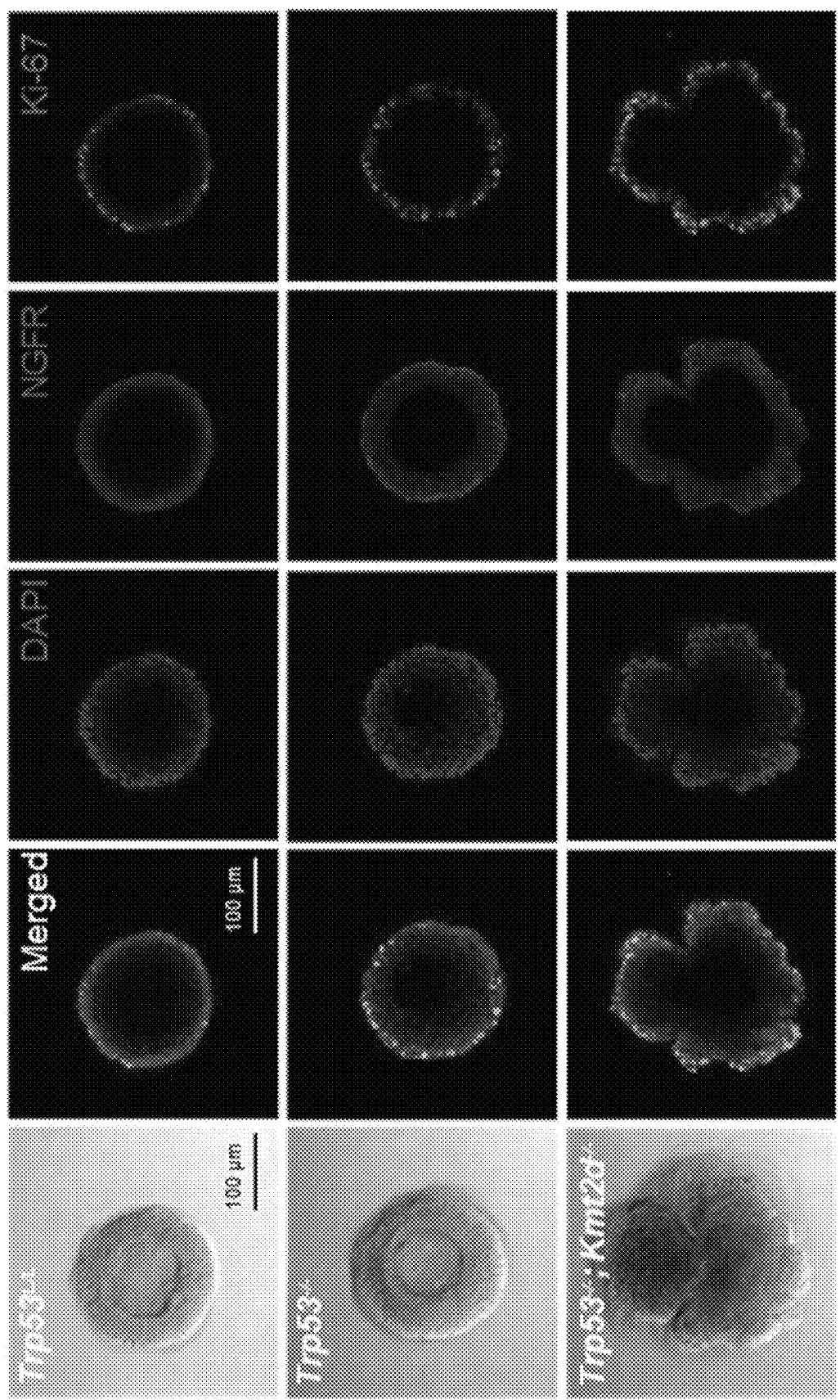
Figure 1:
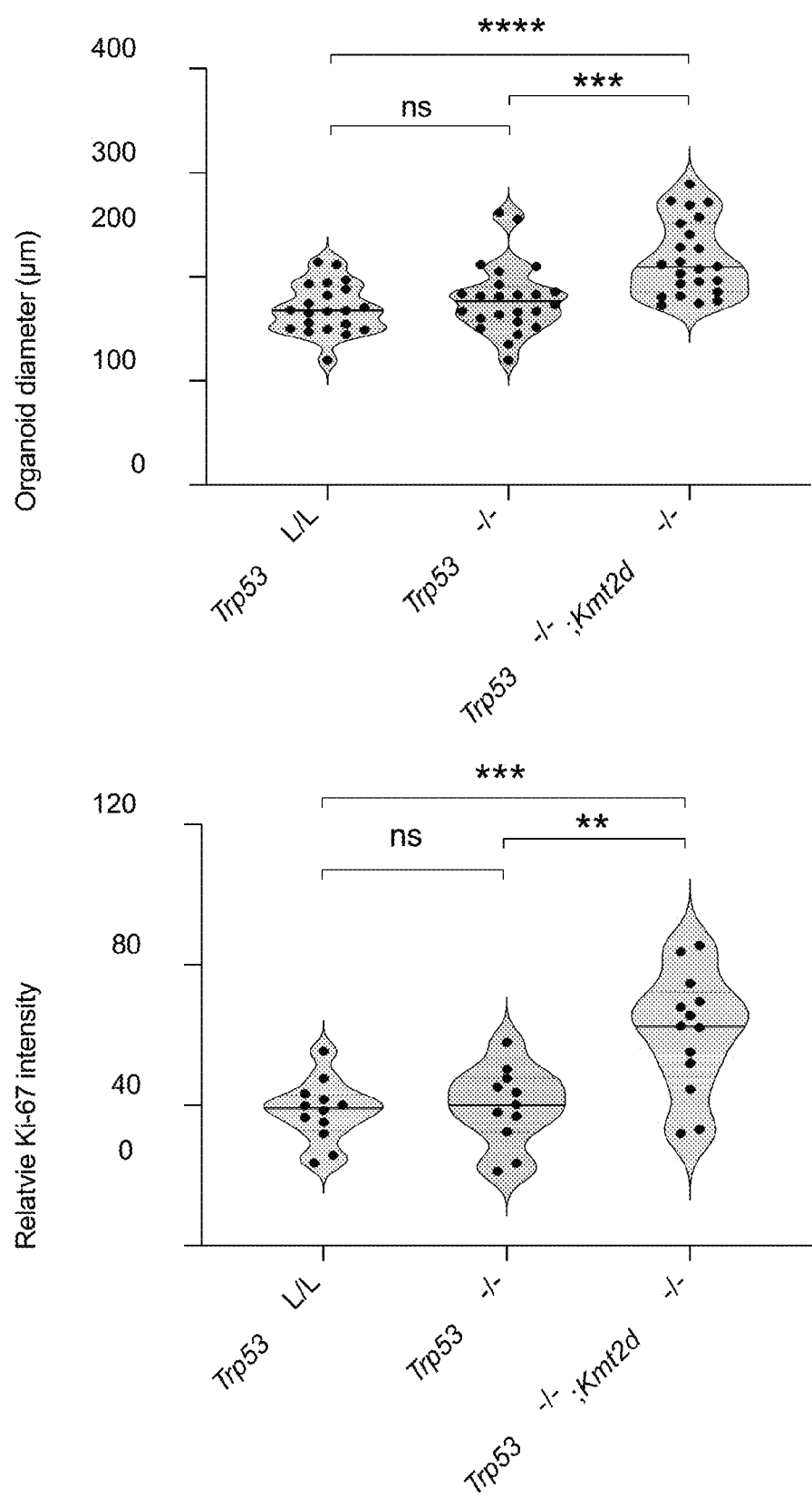
Figure 1:
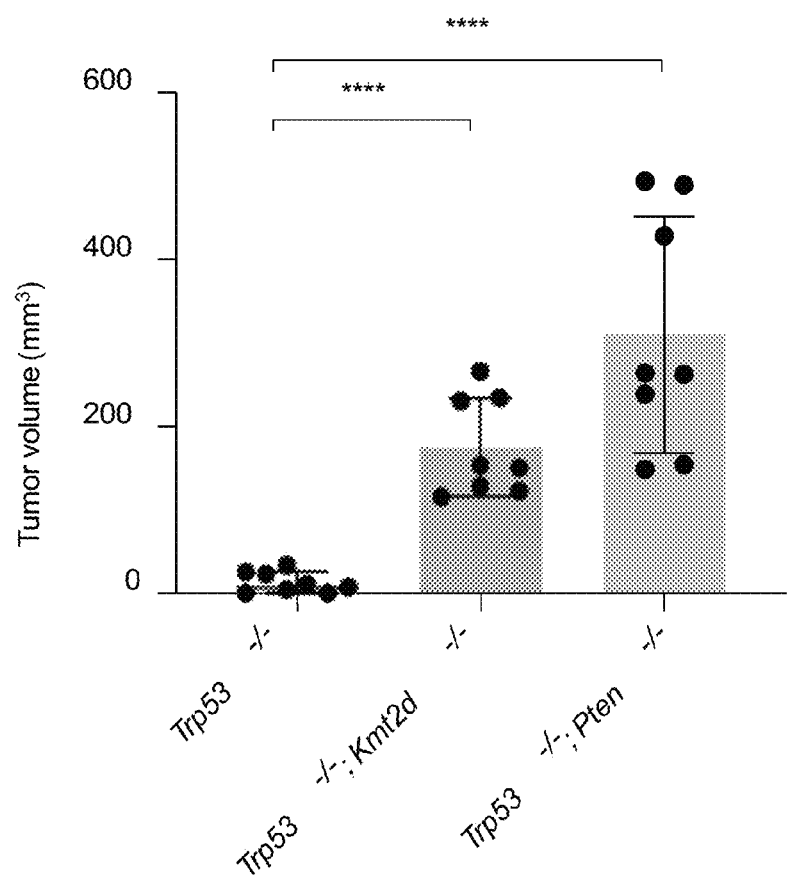
Figure 1:
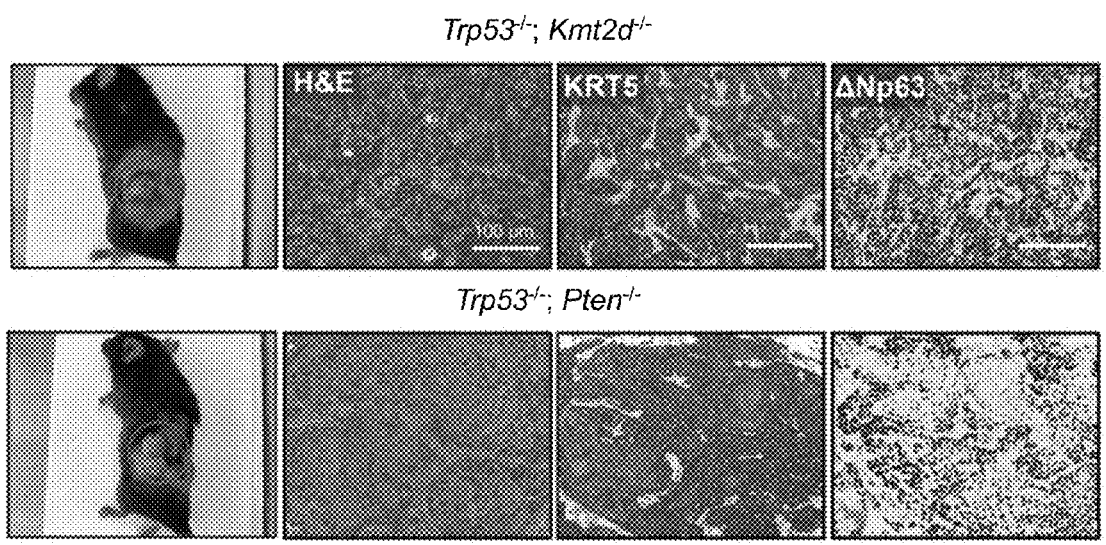

KMT2D is the one of the most frequently mutated genes in LUSC, ranking third (24%) and second (22%) among all cancer-related genes (OncoKB Cancer Gene List) in the TCGA PanCancer Atlas (Cancer Genome Atlas Research et al., 2013) and Genomics, Evidence, Neoplasia, Information, Exchange (GENIE) databases, respectively (Consortium, 2017) (FIG. 8A). The KMT2D protein contains 2 clusters of PHD domains in the N-terminus and the enzymatic SET domain in the C-terminus (Ruthenburg et al., 2007). Almost half of KMT2D mutations are truncating mutations that potentially lead to loss of its catalytic activity (FIG. 8B). In addition, Genotype-Tissue Expression (GTEx, (Consortium, 2013)) and TCGA data revealed that KMT2D expression is significantly lower in LUSC than the matched normal tissue (FIG. 8C). These data indicate that KMT2D might play an important role in governing LUSC oncogenesis. To investigate the function of KMT2D during this process, we utilized a mouse organoid system derived from lung basal progenitor cells (Hai et al., 2020), a hypothesized cell of origin for LUSC (Ferone et al., 2020; Sanchez-Danes and Blanpain, 2018). Because the vast majority of KMT2D mutations co-occur with TP53 mutations (99 in 113 samples, ~87.6%) (FIG. 1A), we first established mouse lung basal cell organoids from tracheal bronchial epithelial cells of C57BL/6J Trp53$^{L/L}$ mice (see Methods), in which the foxed Trp53 allele gene can be conditionally inactivated by the Cre recombinase to generate Trp53 knock-out (Trp53$^{-/-}$). These Trp53$^{L/L}$ normal lung organoids formed epithelial spheres after 7 days of culture (FIG. 9A). After expansion, these organoids were subsequently infected with adenovirus-Cre (Ad-Cre-GFP), followed by flow cytometry sorting of the GFP$^+$ cells, yielding Trp53$^{-/-}$ organoids (FIGS. 1B and 1C).

We next infected Trp53$^{-/-}$ organoids with CRISPR/Cas9 sgRNAs targeting Kmt2d, which were positively selected in the medium with antibiotics. Mutations at Kmt2d locus were subsequently confirmed by genomic sequencing (FIG. 9B) and KMT2D protein loss was further verified by western blot (FIG. 1D). The morphology and histology of the genetically engineered organoids were analyzed by hematoxylin and eosin (H&E) staining and immunohistochemistry (IHC), respectively. Both Trp53$^{L/L}$ and Trp53$^{-/-}$ organoids contain stratified epithelium with basal cells at the periphery (FIG. 1E). Strikingly, deleting Kmt2d in Trp53$^{-/-}$ organoids profoundly affected organoid shape and transformed the stratified layers of epithelia spheres into disorganized cellular masses with loss of cell polarity (FIGS. 1E, 9C and 9D). Furthermore, an increased nuclear to cytoplasmic ratio and a high level of the basal cell marker ΔNp63 (P40) were observed in the Trp53$^{-/-}$; Kmt2d$^{-/-}$ organoids. To examine whether Kmt2d loss confers a growth advantage, we performed immunofluorescence staining of the proliferation marker Ki-67 on the organoids. Compared to the Trp53$^{-/-}$ and Trp53$^{-/-}$ parental organoids, Trp53$^{-/-}$; Kmt2d$^{-/-}$ organoids exhibited significantly higher Ki-67 expression in the basal epithelia marked by NGFR expression (FIGS. 1F and 1G). As a result, Trp53$^{-/-}$; Kmt2d$^{-/-}$ organoids grew to a larger size compared to the parental controls. These data indicate that Kmt2d deletion promotes the oncogenic overgrowth in lung basal cell organoids in vitro, which is consistent with early malignant transformation.

Example 3

Kmt2d Deletion Drives LUSC In Vivo

To investigate the oncogenic potential of the genetically engineered organoids in vivo, we implanted the Trp53$^{-/-}$; Kmt2d$^{-/-}$ organoids and control Trp53$^{-/-}$ organoids into flanks of C57BL/6J mice. In parallel, we established the Trp53$^{-/-}$; Pten$^{-/-}$ organoids and injected in vivo as a control for LUSC, because PTEN is frequently mutated in LUSC (FIG. 9E) and PTEN inactivation promotes oncogenic tumor growth in multiple LUSC models (Ferone et al., 2016; Hai et al., 2020; Xu et al., 2014). Six-weeks after injection, tumors formed in mice injected with Trp53$^{-/-}$; Kmt2d$^{-/-}$ and Trp53$^{-/-}$; Pten$^{-/-}$ organoids, but not with the Trp53$^{-/-}$ organoids (up to 30 weeks of observation), suggesting Trp53 loss alone in basal cell organoids is not sufficient to generate LUSC in vivo (FIG. 1H). Histologic analysis of both tumors revealed keratinization, keratin pearl formation and strong expression of KRT5 and ΔNp63, consistent with LUSC hallmarks (FIGS. 1I and 9F). To further evaluate whether Trp53$^{-/-}$; Kmt2d$^{-/-}$ organoids can directly form LUSC in mouse lungs, we performed transthoracic orthotopic implantation of the organoids under ultrasound guidance (FIG. 9G). Remarkably, Trp53$^{-/-}$; Kmt2d$^{-/-}$ organoids formed lung tumors orthotopically that mirrored histological features of LUSC, with a latency (40-50 weeks) similar to that of the genetically engineered mouse models (GEMMS) of LUSC (Pan et al., 2021). In summary, these findings support that Kmt2d deletion, in the absence of Trp53, is able to drive LUSC formation in vivo.

Example 4

Establishing the Optimal Kmt2d-Deficient Orthotopic LUSC Model

Figure 2:
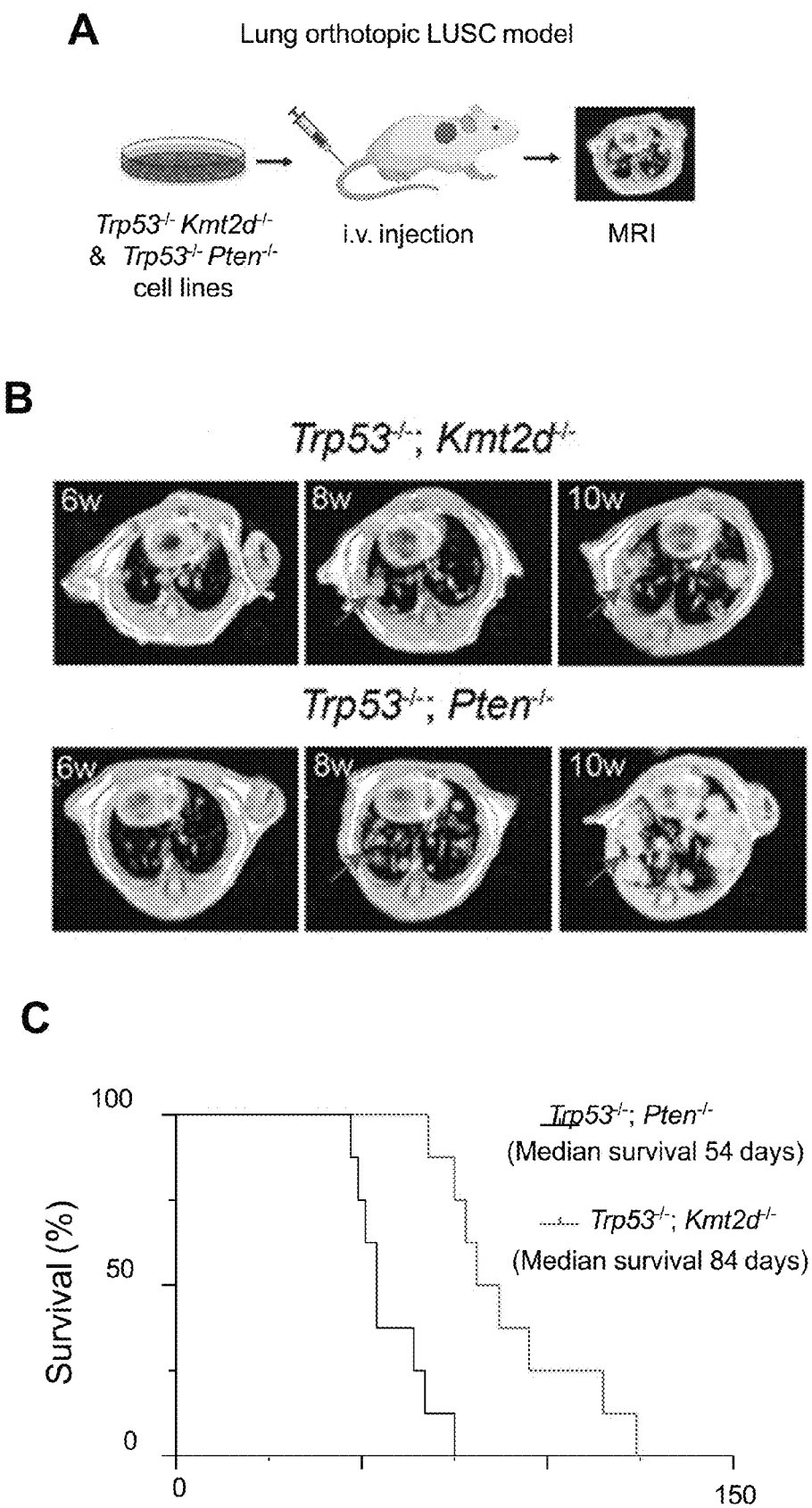
FIG. 2. KMT2D deletion drives LUSC in vivo. (A) Schematic illustration of establishing the orthotopic LUSC model from tumor-derived syngeneic cells. Tumor growth was monitored by magnetic resonance imaging (MRI). (B) Lung MRI images of 6 weeks, 8 weeks, and 10 weeks after injection of cells with indicated genotypes. The red arrows indicate the location of lung tumors. (C) Kaplan-Meier curves of mice following implanting cells with the indicated genotypes. (n=8 for Trp53–/–; Kmt2d–/– and n=8 for Trp53–/–; Pten–/–). (D) H&E staining of Trp53–/–; Kmt2d–/– and Trp53–/–; Pten–/– lung tumors with squamous histology. (Right) Higher magnification of the boxed regions. (E) IHC analysis of ΔNp63, KRT5, TTF1 and KMT2D from lung tumors with the indicated genotypes. Scale bars, 100 μm. (F) Heatmap and hierarchical clustering of differentially expressed transcripts from normal mouse lung tissues, LUAD (KrasG12D; Trp53–/–) and LUSC of Trp53–/–; Kmt2d–/– and Trp53–/–; Pten–/–. (G) Gene expression heatmap of LUSC and LUAD marker genes in normal mouse lung tissues, LUAD (KrasG12D; Trp53–/–) and LUSC of Trp53–/–; Kmt2d–/– and Trp53–/–; Pten–/–. Genes were classified into "Keratins", "Transcription factors (or TFs)", "Secreted factors", "Cell surface" and "Enzymes" categories.
Figure 2:
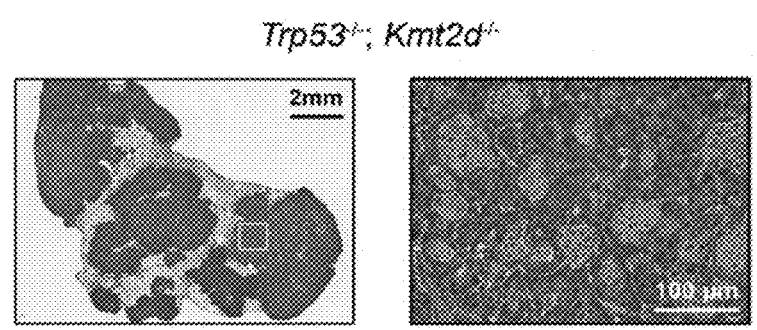
Figure 2:
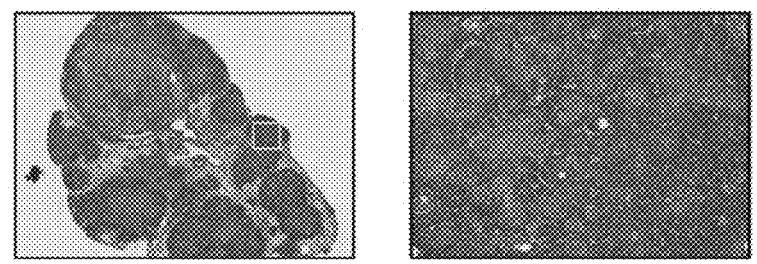
Figure 2:
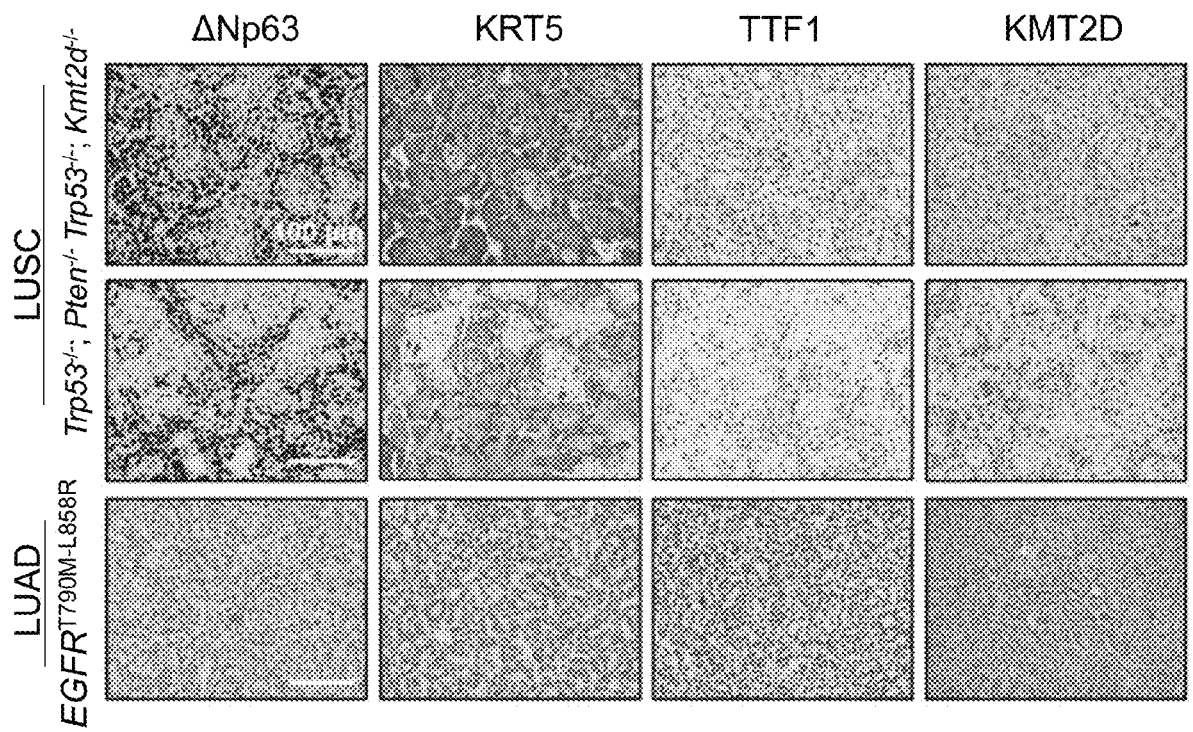
Figure 2:
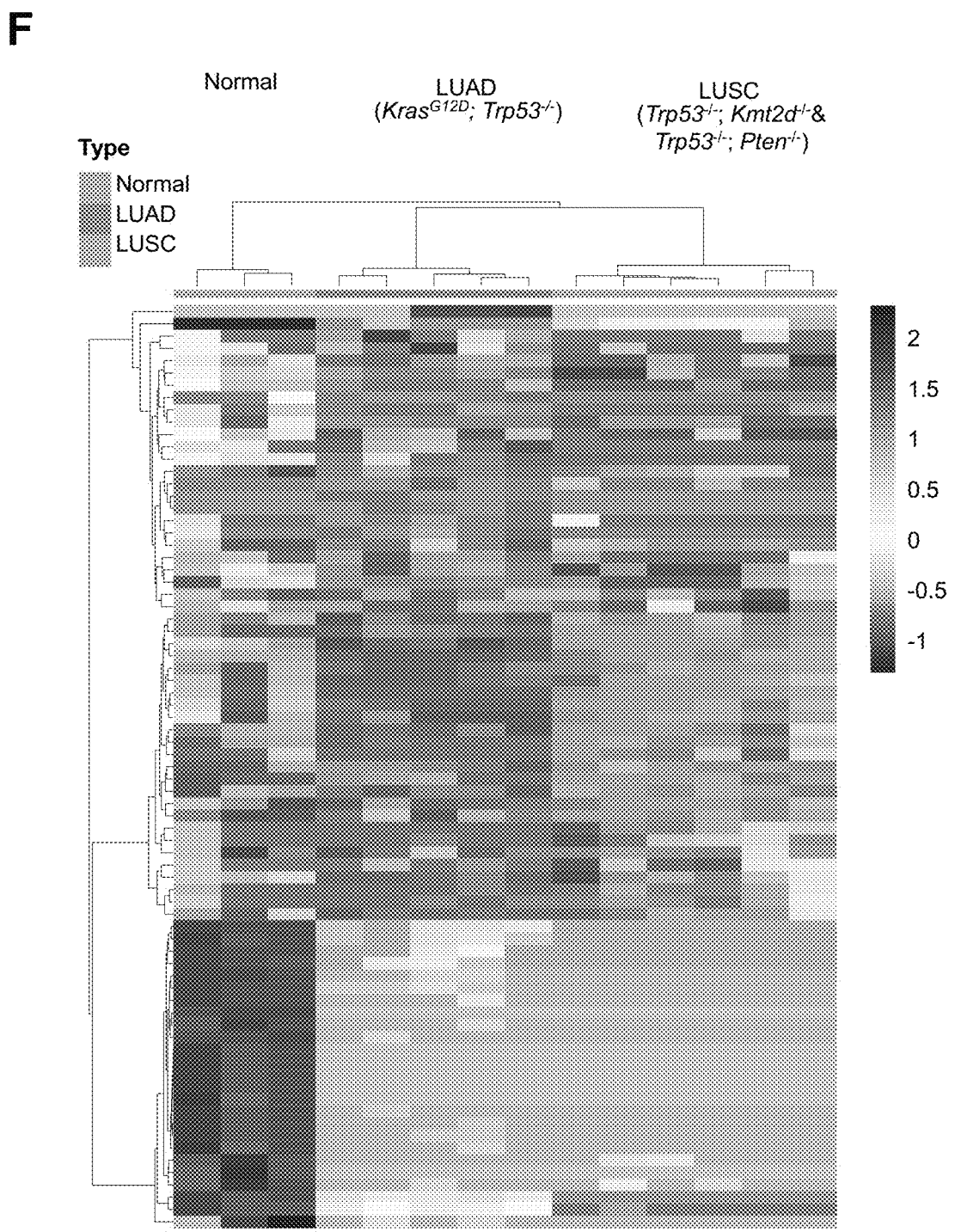
Figure 2:
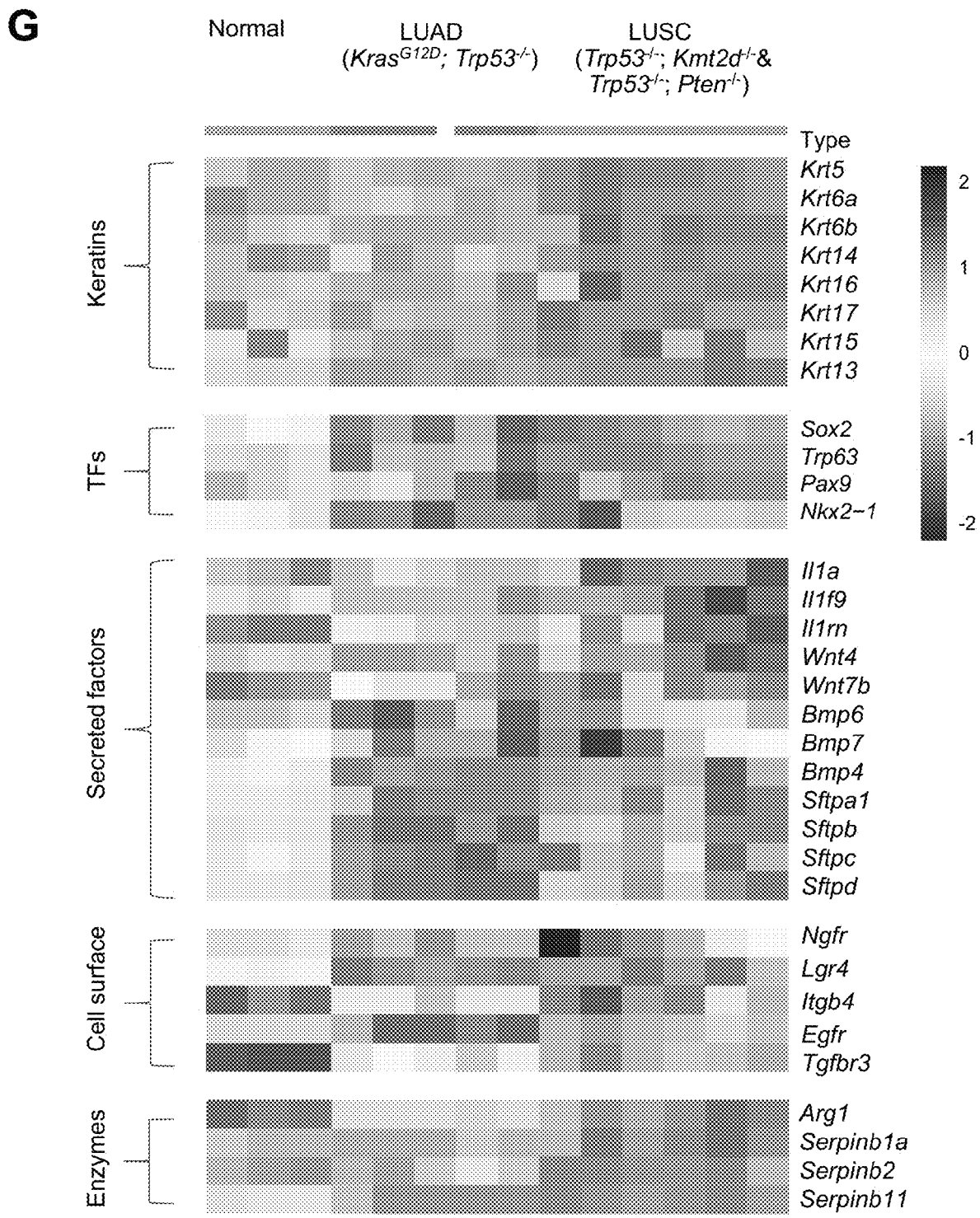

The long and variable latency of the transthoracic model renders it not optimal for evaluation of KMT2D function and for identification of therapeutic vulnerabilities in vivo. Thus, to establish a robust orthotopic LUSC model (with a consistent and short latency) for further characterization, we first harvested the Trp53$^{-/-}$; Kmt2d$^{-/-}$ tumor nodules and generated the syngeneic Trp53$^{-/-}$; Kmt2d$^{-/-}$ cell lines (FIGS. 1B and 10A). We next inoculated Trp53$^{-/-}$; Kmt2d$^{-/-}$ cells into C57BL/6J mice through intravenous injection and monitored tumor growth in the lung by magnetic resonance imaging (MRI) (FIG. 2A). Likewise, as an alternative LUSC model for comparison, we also established the Trp53$^{-/-}$; Pten$^{-/-}$ orthotopic model in C57BL/6J mice. Six to eight weeks after implantation, mice injected with Trp53$^{-/-}$; Kmt2d$^{-/-}$ or Trp53$^{-/-}$; Pten$^{-/-}$ cells both developed lung tumors (FIG. 2B). The Trp53$^{-/-}$; Kmt2d$^{-/-}$ cells and orthotopic tumors grew slower than the Trp53$^{-/-}$; Pten$^{-/-}$ counterparts (FIGS. 10B and 2B). Accordingly, the Trp53$^{-/-}$; Kmt2d$^{-/-}$ tumor bearing mice had longer survival than the Trp53$^{-/-}$; Pten$^{-/-}$ counterparts, with a median survival of 84 days (n=8) and 54 days (n=8), respectively (FIG. 2C). To confirm the lung tumor histology, we performed H&E and IHC staining of the LUSC markers including ΔNp63 and KRT5, and the LUAD marker TTF1. EGFR$^{T790M-L858R}$ mouse lung tumors, the well-established LUAD, were used as a negative control (Li et al., 2007). H&E staining of Trp53$^{-/-}$; Kmt2d$^{-/-}$ tumors showed clear squamous features such as stratification and keratinization, which were also observed in the Trp53$^{-/-}$; Pten$^{-/-}$ lung tumors (FIG. 2D). Trp53$^{-/-}$; Kmt2d$^{-/-}$ tumors strongly expressed the LUSC markers ΔNp63 and KRT5, but not the LUAD marker TTF1, similar to the Trp53$^{-/-}$; Pten$^{-/-}$ lung tumors (FIG. 2E). In contrast, the EGFR-mutant LUAD tumors were positive for TTF1, but negative for ΔNp63 and KRT5. To further confirm the Kmt2d loss in Trp53$^{-/-}$; Kmt2d$^{-/-}$ tumors, we also performed IHC staining of KMT2D in the tumor sections. As expected, KMT2D is not detected in the Trp53$^{-/-}$; Kmt2d$^{-/-}$ tumors, whereas Trp53$^{-/-}$; Pten$^{-/-}$ and EGFR-mutant tumors expressed KMT2D in the nucleus (FIG. 2E). Thus, these orthotopic Trp53$^{-/-}$; Kmt2d$^{-/-}$ lung tumors exhibit classic LUSC histopathology that recapitulates human disease with precision.

To examine whether the Trp53$^{-/-}$; Kmt2d$^{-/-}$ and Trp53$^{-/-}$; Pten$^{-/-}$ tumors recapitulate the molecular signature of LUSC, bulk RNA sequencing (RNA-seq) was performed to comprehensively evaluate the transcriptomic features. In parallel, we also analyzed the gene expression profiles of LUAD tumors (Kras$^{G12D}$; Trp53$^{-/-}$ or, KP) and normal lungs for comparison (Deng et al., 2021; Mollaoglu et al., 2018). Principal component analysis (PCA) revealed that the Trp53$^{-/-}$; Kmt2d$^{-/-}$ and Trp53$^{-/-}$; Pten$^{-/-}$ tumors were clustered together and separated from the KP (LUAD) tumors and normal lung samples (FIG. 10C). Unsupervised hierarchical clustering of differentially expressed genes also revealed a high level of similarity between Trp53$^{-/-}$; Kmt2d$^{-/-}$ and Trp53$^{-/-}$; Pten$^{-/-}$ tumors, which are distinct from KP tumors and normal lung tissues (FIG. 2F). Expression of LUSC hallmark genes was evidently upregulated and the levels of LUAD associated genes were decreased in Trp53$^{-/-}$ Kmt2d$^{-/-}$ and Trp53$^{-/-}$; Pten$^{-/-}$ tumors, compared with the KP tumors and normal lung tissues (FIG. 2G). For example, levels of cytokeratin genes such as Krt5, Krt14, Krt15 and transcriptional factors genes Sox2 and Trp63 were elevated, whereas expressions of LUAD marker genes including Nkx2-1, Sftpa1, Sftpb, Sftpc and Sftpd were decreased. Additionally, expressions of genes encoding secreted factors such as Wnt (Wnt4, Wnt7b), Bmp (Bmp6, Bmp7) and interleukin superfamilies (Il1a, Il1f9, Il1rn), transcriptional factors (Pax9), enzymes (Arg1, Serpinb1a, Serpinb2, Serpinb11), and cell surface proteins (Ngfr, Lgr4, Egfr, Itgb4) were increased in the Trp53$^{-/-}$; Kmt2d$^{-/-}$ and Trp53$^{-/-}$; Pten$^{-/-}$ tumors, similar to the gene expression profiles of LUSC GEMMs and human LUSC tumors (Ferone et al., 2016; Mollaoglu et al., 2018; Xu et al., 2014). Taken together, these findings indicate that Trp53$^{-/-}$; Kmt2d$^{-/-}$ tumors strongly recapitulate the histologic and molecular signatures of human LUSC.

Example 5

Kmt2d Deletion Activates the RTK-Ras Signaling in LUSC

Figure 3:
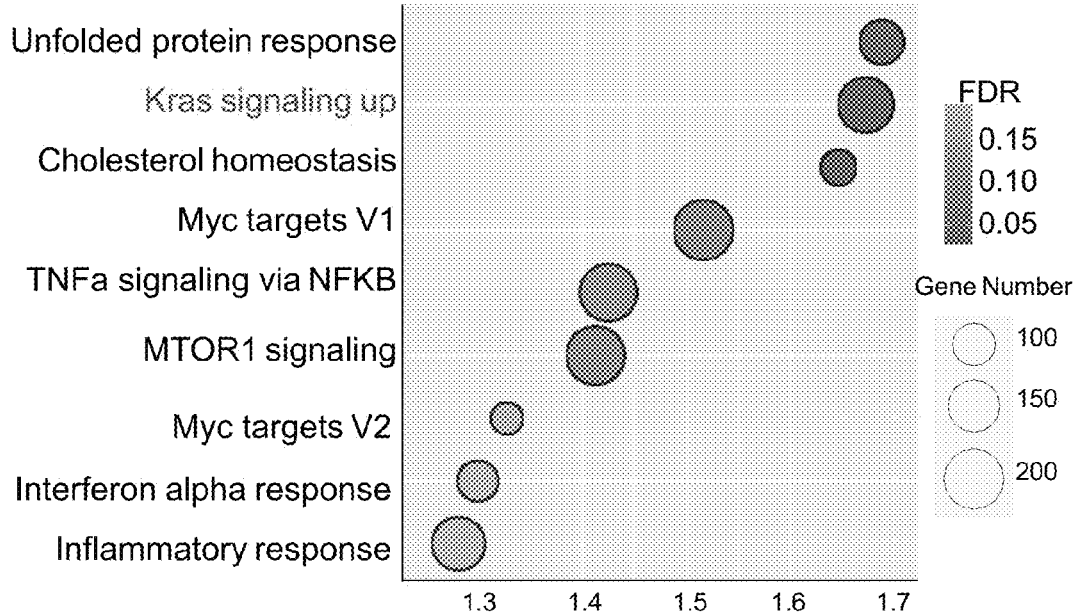
FIG. 3. KMT2D deletion activates the RTK-Ras signaling in LUSC. (A) Dot plot of positively enriched pathways (NOM P<0.05 and FDR q<0.25) in Gene Set Enrichment Analysis (GSEA) results from Kmt2d KO (Trp53$^{-/-}$; Kmt2d$^{-/-}$) versus the Kmt2d WT (Trp53$^{-/-}$; Pten$^{-/-}$) tumor-derived cell lines. "Kras signaling up" ranks second among the positively enriched pathways. (B) GSEA analysis of RNA-seq for Kmt2d KO versus Kmt2d WT cell lines indicated that Kras signaling was significantly enriched. (C)
Figure 3:
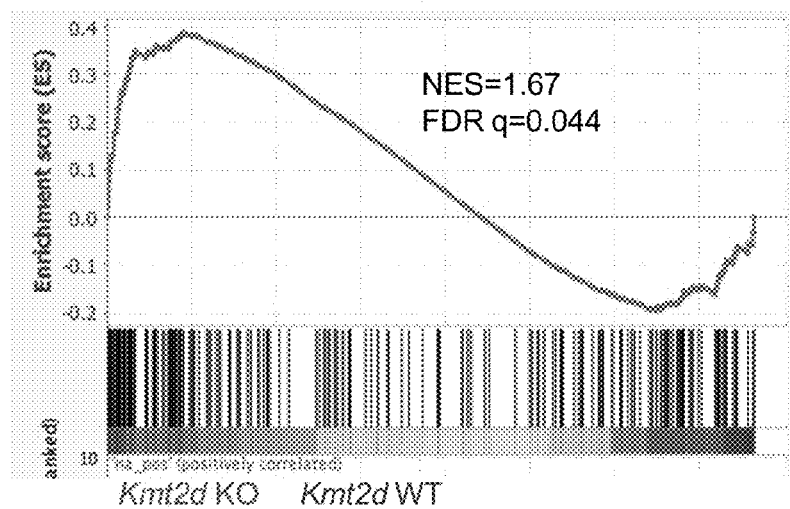
Figure 3:
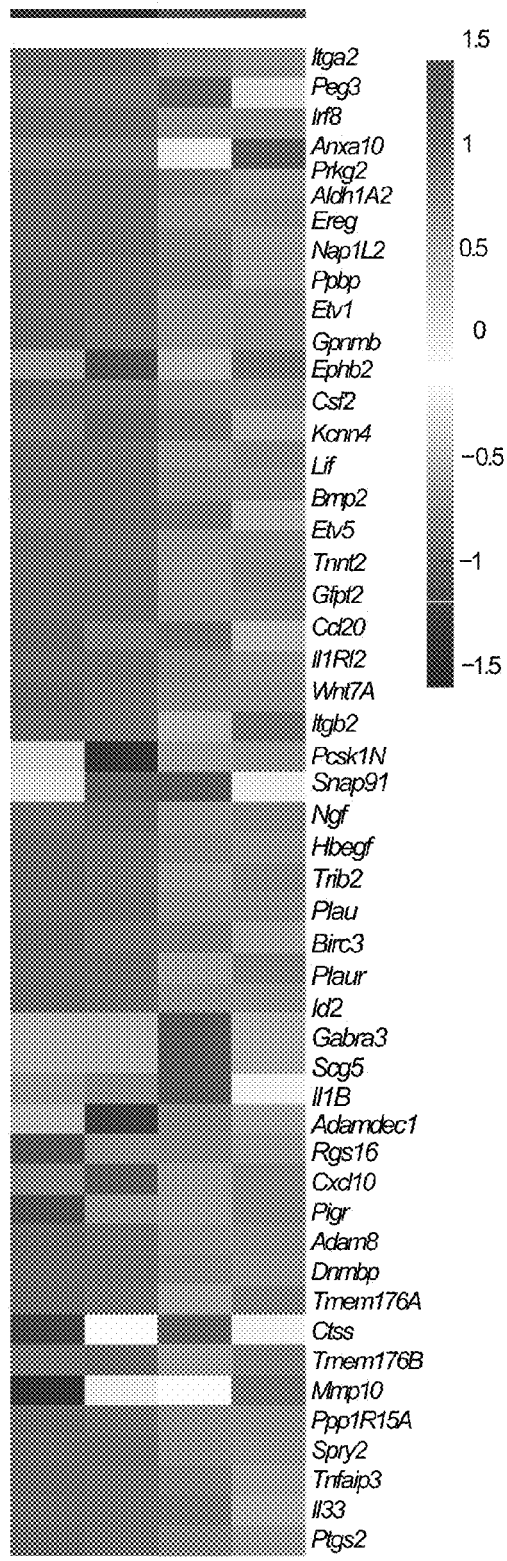
Figure 3:
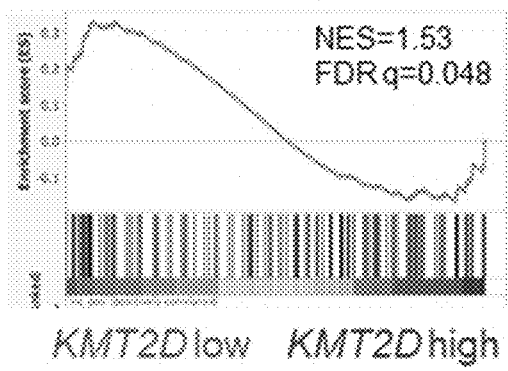
Figure 3:
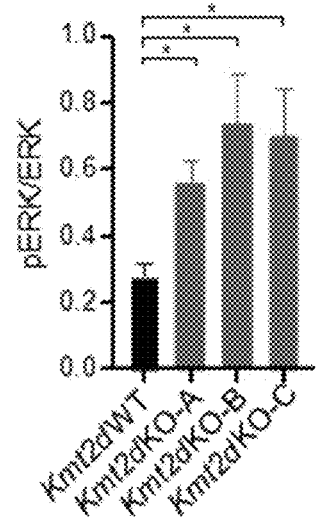
Figure 3:
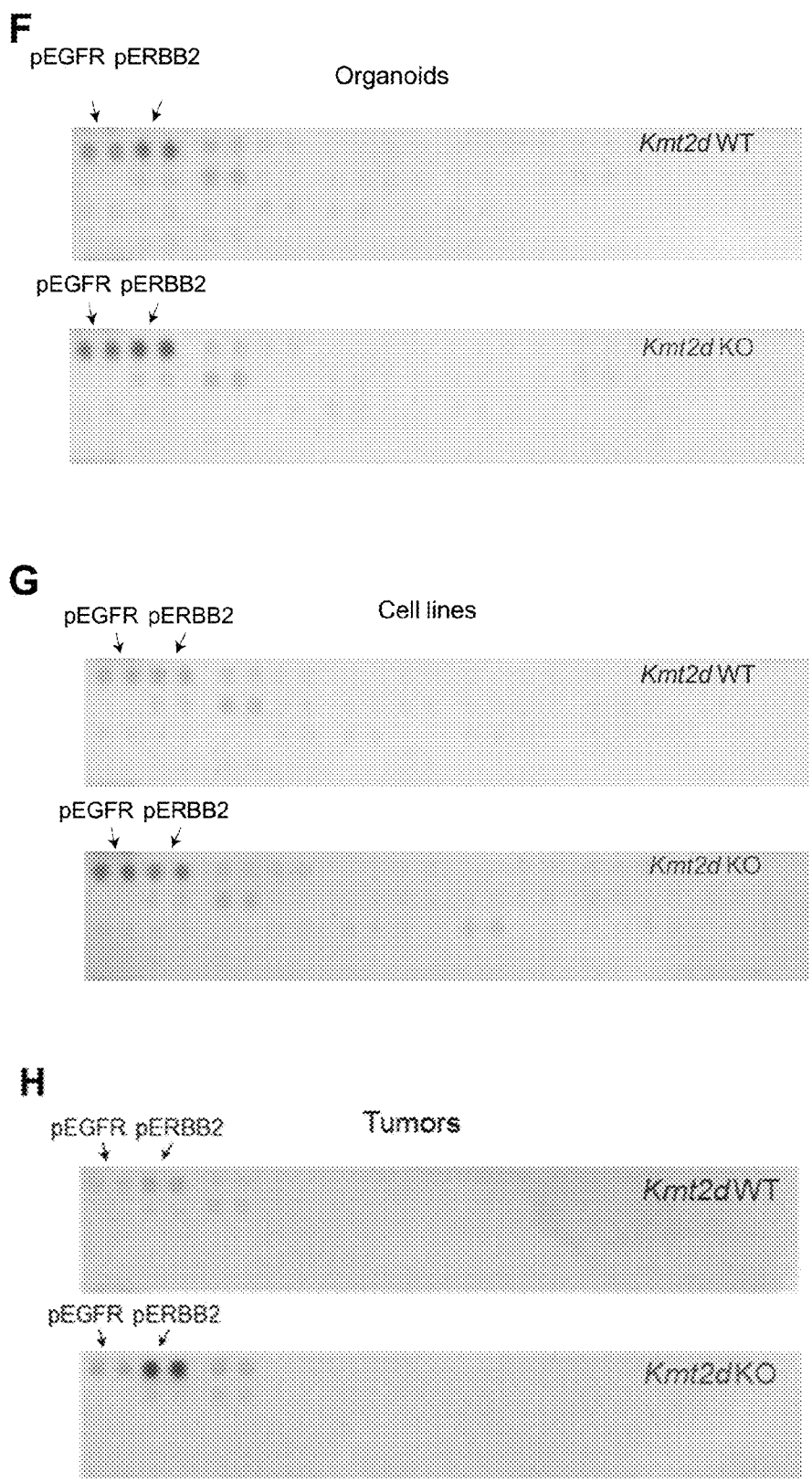
Figure 3:
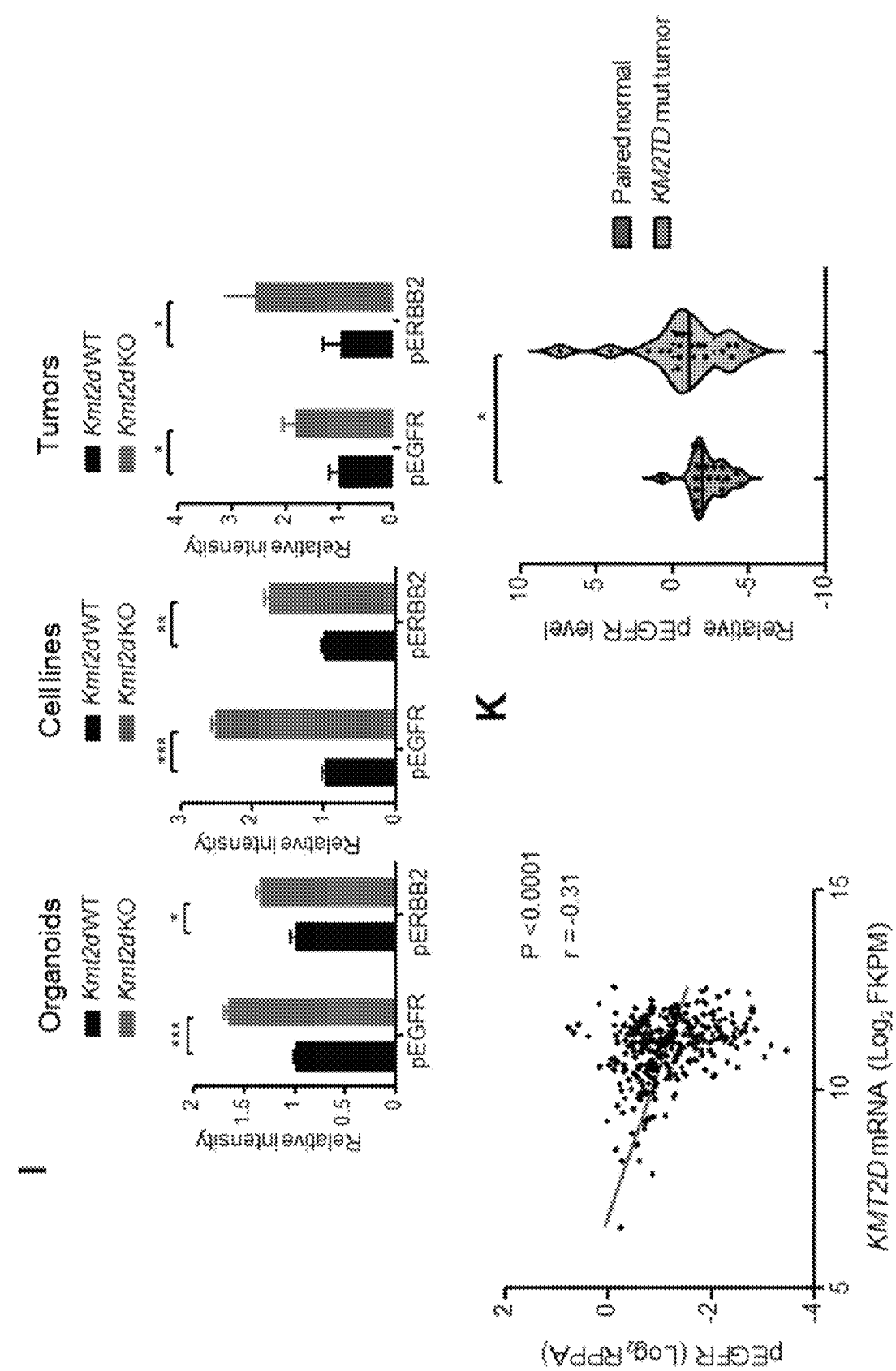

We next sought to characterize the molecular features that are unique to Trp53$^{-/-}$; Kmt2d$^{-/-}$ (Kmt2d KO, used hereafter), in comparison to those of the Kmt2d wild-type (Kmt2d WT, Trp53$^{-/-}$ or Trp53$^{-/-}$; Pten$^{-/-}$) counterparts. Gene set enrichment analysis (GSEA) of the transcriptomic data revealed that Kras signaling was one of the most positively enriched signatures in the Kmt2d KO cell lines, compared to the Kmt2d WT cell lines (FIGS. 3A and 3B). A large number of Kras signaling related genes, such as Etv1, Etv5, Spry2 and Ereg, were upregulated upon Kmt2d loss (FIG. 3C). In addition to the activation of Kras signaling, several other key cancer hallmark signatures were significantly elevated, including "unfolded protein response", "cholesterol homeostasis", "Myc targets V1", "TNFa signaling via NFKB" and "mTOR1 signaling" in the Kmt2d KO cells (FIG. 3A). Consistently, GSEA of the differentially expressed genes revealed that Kras signaling is also one of the most positively regulated signatures in the Kmt2d KO organoids, compared to the Kmt2d WT organoids (FIG. 10D). Analysis of TCGA LUSC database further confirmed that Kras signaling was enriched in human KMT2D-low LUSC versus KMT2D-high LUSC samples (FIG. 3D). Moreover, in line with Kras signaling activation, phospho-ERK level was much higher in three different Kmt2d KO cell lines, compared to the Kmt2d WT cells (FIG. 3E). We next sought to identify the potential upstream regulators responsible for the aberrant Kras signaling upon Kmt2d loss. Given that receptor tyrosine kinases (RTKs) are well-characterized activators of the Kras signaling in cancer (McKay and Morrison, 2007), we performed a comprehensive phospho-RTK array, which interrogates the phosphorylation of 39 RTKs (FIGS. 3F-3I). Notably, a significant increase in EGFR and ERBB2 phosphorylation was observed in Kmt2d KO organoids and cell lines when compared to the Kmt2d WT counterparts, whereas a minimal difference was detected in the levels of other phosphorylated RTKs, including ERBB3 and ERBB4 (FIGS. 3F, 3G and 3I). We next performed the phospho-RTK array on Kmt2d KO and Kmt2d WT lung tumors to examine whether Kmt2d loss might also alter EGFR and ERBB2 phosphorylation in vivo. Consistently, Kmt2d KO tumors had significantly higher levels of EGFR and ERBB2 phosphorylation, compared to the Kmt2d WT tumors (FIGS. 3H and 3I). Western blot further confirmed the increased phosphorylation of EGFR and ERBB2 in the Kmt2d KO tumors (FIG. 10E). Therefore, our data suggest that RTK-Ras signaling is activated upon Kmt2d loss in LUSC.

We further investigated whether increased levels of EGFR phosphorylation are associated with KMT2D loss in human LUSC. Utilizing the DepMap dataset (https://depmap.org/portal/) (Ghandi et al., 2019), we investigated the correlation between KMT2D expression and levels of phospho-EGFR in a panel of 19 human LUSC cell lines. Consistently, KMT2D expression was negatively correlated with phospho-EGFR levels, measured by reverse phase protein arrays (RPPA) (FIG. 10F). Exploiting the TCGA Pan-Cancer Atlas dataset (Cancer Genome Atlas Research et al., 2013; Hoadley et al., 2018), we next analyzed the correlation between KMT2D RNA levels with phosphorylated EGFR in human LUSC specimens. KMT2D mRNA abundance was negatively correlated with the level of phospho-EGFR (FIG. 3J), further supporting our observations in the cell lines and mouse tumors. To validate this finding in separate cohorts, we expanded our analyses and mined a large-scale collection of a proteomics dataset of LUSC tumors and paired normal adjacent tissues (Satpathy et al., 2021). Our analysis revealed that KMT2D mutant LUSC tumors exhibited elevated phospho-EGFR compared to the paired normal lung tissues (FIG. 3K). Finally, we knocked out KMT2D in human LUSC cell lines (EBC1 and HCC95) using 2 different sgRNA to evaluate the impact on phospho-EGFR (FIGS. 10G and 10H). Notably, KMT2D loss led to an increase in the levels of phospho-EGFR in human LUSC cells.

In summary, our data suggest that Kmt2d deletion promotes oncogenic RTK-Ras signaling through activating EGFR and ERBB2 in both murine and human LUSC.

Example 6

KMT2D Deficiency Confers Hypersensitivity to SHP2 and Pan-ERBB Inhibition In Vitro We next sought to identify potential therapeutic vulnerabilities of KMT2D-deficient LUSC. Based upon the aforementioned findings, we reasoned that Kmt2d KO LUSC would be hypersensitive to inhibitors that target oncogenic RTK-Ras signaling, which is markedly elevated upon Kmt2d loss. SHP2 (encoded by PTPN11) is a protein tyrosine phosphatase that mediates Kras activation downstream of RTKs (Chan et al., 2008). Targeting SHP2 with the allosteric inhibitor SHP099 has been shown to be effective in both Kras mutant and Kras wild-type tumors with elevated RTK-Ras signaling (Chen et al., 2016; Fedele et al., 2018; Wong et al., 2018). Afatinib is a pan-ERBB family receptor tyrosine kinase inhibitor, which has been approved for the second-line treatment in LUSC (Santos and Hart, 2020; Soria et al., 2015). Thus, we hypothesized that SHP099 and afatinib would inhibit KMT2D-deficient LUSC growth in vitro and in vivo (FIG. 4A). We investigated the effects of SHP099 and afatinib on cell viability in three different Kmt2d KO LUSC cell lines, Kmt2d WT LUSC cell lines, and the KP LUAD cell line. Notably, all three Kmt2d KO LUSC cell lines were hypersensitive to the treatment of SHP099, with the IC50 of 0.559 µM, 0.310 µM and 1.165 µM respectively (FIG. 4B). In comparison, the IC50 of SHP099 in Kmt2d WT squamous cell lines were 9.429 µM and 4.79 µM, whereas the IC50 in KP cells was higher than 20 µM. The hypersensitivity in the Kmt2d KO cells and specificity to SHP2 inhibition were further confirmed by knocking out SHP2 using CRISPR/cas9 gRNA and another SHP2 selective inhibitor (FIGS. 11A and 11B). Furthermore, afatinib was highly effective in inhibiting cell viability in the Kmt2d KO LUSC cell lines, with a much lower IC50 of less than 0.02 µM (FIG. 4C), in comparison to >1 µM in Kmt2d WT LUSC cell lines and KP cells. In line with this, Kmt2d KO LUSC cell lines were also more sensitive to another pan-ERBB inhibitor neratinib, when compared with Kmt2d WT squamous cell lines and KP cells (FIG. 11C). Additionally, utilizing the DepMap dataset, our analysis revealed that lower KMT2D levels were significantly associated with a higher sensitivity to afatinib and other pan-ERBB inhibitors including neratinib, lapatinib and poziotinib (Corsello et al., 2020) (FIG. 11D). To evaluate the long-term effect of SHP099 and afatinib on cell survival, we performed a seven-day colony formation assay with SHP099, afatinib alone or in combination in Kmt2d KO cells. SHP099 and afatinib alone dramatically inhibited the colony formation in in Kmt2d KO cells, whereas combining SHP099 and afatinib led to a further reduction of the colonies (FIG. 4D). These findings suggest that Kmt2d KO cells are hypersensitive to SHP2 and pan-ERBB inhibitors, such as SHP099 and afatinib, and this inhibitory effect is further enhanced when combining SHP099 and afatinib.

Example 7

SHP099 and Afatinib Attenuate RTK-Ras Signaling in Kmt2d KO LUSC

We next examined whether SHP099 and afatinib alone, and in combination, would inhibit the RTK-Ras signaling in Kmt2d KO LUSC in vitro and in vivo. Treating Kmt2d KO LUSC cells in vitro with SHP099 or afatinib alone robustly reduced pERK levels (FIG. 11E). Combining SHP099 with afatinib led to the most significant reduction in pERK levels. To further examine the downstream effects in vivo, we established the Kmt2d KO LUSC model through intravenous injection (FIG. 2A). After confirming tumor volumes by MRI, mice were randomized into four groups, vehicle, SHP099 (75 mpk, QD), afatinib (10 mpk, QD) and combined SHP099 with afatinib (combo). Tumor nodules were collected after three-days of the treatment to examine the pharmacodynamics on downstream signaling. As expected, western blot analysis revealed that in comparison to the vehicle, SHP099 and afatinib monotherapy substantially reduced the levels of pERK, while the combination therapy led to a greater decrease (FIG. 4E). In line with these results, transcriptomic analysis of tumor nodules by RNA-seq showed that the levels of Kras-dependent genes were pronouncedly downregulated upon SHP099, afatinib monotherapy, and in the combinational treatment (FIG. 4F). Furthermore, GSEA of the differentially expressed genes revealed that the combination treatment negatively affected genes associated with "E2F targets", "G2M checkpoint" and "Myc targets" (FIGS. 4G and 4H). To further characterize the antiproliferative impact of SHP099 and afatinib, we performed IHC staining of the proliferation marker Ki-67 and apoptotic marker cleaved caspase-3 on the treated Kmt2d KO tumors. SHP099 and afatinib alone significantly decreased Ki-67 expression and increased cleaved caspase-3 levels in vivo (FIGS. 4 and 4J), whereas the combination treatment led to the most significant reduction in Ki-67 and increase in cleaved caspase-3. Collectively, SHP099 and afatinib alone significantly inhibits the RTK-Ras signaling in Kmt2d KO tumor in vitro and in vivo, which is further enhanced when in combination.

Example 8

SHP099 and Afatinib Diminish KMT2D-Deficient LUSC In Vivo

We next determined whether targeting SHP2 and ERBB would inhibit tumor growth and prolong survival in Kmt2d KO LUSC in vivo. Upon confirmation of tumor burden, mice were randomized to vehicle, SHP099, afatinib and the combination treatment (combo), and monitored via MRI (FIGS. 5A and 12A). An additional group of mice were enrolled to chemotherapy (carboplatin plus paclitaxel) as the standard-of-care regimen for comparison. No significant weight loss was observed in all treatment groups (FIG. 12B). All vehicle-treated mice displayed aggressive disease, with tumor volumes doubled after a 2-week period (FIGS. 5B-5D). While chemotherapy showed no effect in inhibiting tumor growth, SHP099 or afatinib alone significantly shrank Kmt2d KO LUSC tumors. Notably, combining SHP099 and afatinib led to the most dramatic decrease of tumor volumes, with a reduction observed in all treated mice (n=9), and two thirds (6 of 9) of the mice having >50% reductions (FIGS. 5B-5D). Long term MRI follow-up revealed that tumors began to develop resistance to SHP099 and afatinib monotherapy after 4 weeks of treatment, and by 6 weeks, most mice in the monotherapy groups had progressive disease (FIG. 5E). This is in stark contrast to the mice in the combo treatment, which had a much longer anti-tumor inhibition, with 7 of 9 (77.78%) mice still undergoing tumor shrinkage after 6 weeks of treatment.

We next examined whether the impressive efficacy of SHP2 and pan-ERBB inhibition can also prolong the survival of Kmt2d KO LUSC tumor-bearing mice. As expected, compared with the vehicle group, chemotherapy failed to prolong overall survival (OS) (FIG. 5F). Afatinib monotherapy moderately prolonged animal survival, but the benefit was not statistically significant. Notably, SHP099 treatment markedly increased the median OS to 64 days, compared to the 41 days in the vehicle group. Most importantly, combining SHP099 and afatinib dramatically increased the OS of tumor-bearing mice in comparison to either SHP099 or afatinib alone. Compared with the vehicle, the combination treatment led to more than a 2-fold increase in median OS (84 days versus 41 days), with an added median OS benefit of 43 days. By contrast, the Kmt2d WT LUSC (Trp53$^{-/-}$; Pten$^{-/-}$) appeared to be less sensitive to SHP099 or afatinib monotherapy, and combination therapy (FIG. 12C), consistent with the in vitro drug treatment results (FIGS. 4B and 4C). To further validate the sensitivity is due to Kmt2d loss, we generated the Trp53$^{-/-}$; Pten$^{-/-}$; Kmt2d$^{-/-}$ model and directly compared the in vivo response to SHP2 and pan-ERBB inhibition between Trp53$^{-/-}$; Pten$^{-/-}$; Kmt2d$^{-/-}$ and Trp53$^{-/-}$; Pten$^{-/-}$ LUSC. The Trp53$^{-/-}$; Pten$^{-/-}$; Kmt2d$^{-/-}$ LUSC grew at similarly speed compared to that of the Trp53$^{-/-}$; Pten$^{-/-}$ LUSC in vivo. Remarkably, Trp53$^{-/-}$; Pten$^{-/-}$; Kmt2d$^{-/-}$ LUSC was particularly sensitive to the combination treatment (FIGS. 5G and 12D). All of the tumors (7/7, 100%) exhibited a volume reduction after 3 weeks of treatment (FIG. 12D). Thus, loss of Kmt2d in in murine Trp53$^{-/-}$; Pten$^{-/-}$ LUSC enhances their response to SHP2 and pan-ERBB inhibition.

We next sought to evaluate whether SHP2 and pan-ERBB inhibition might also lead to tumor inhibition in human LUSC with KMT2D mutation in vivo. LK2, a human LUSC cell line with the KMT2D nonsense mutation, was subcutaneously implanted into the flank of nude mice, which were then randomized to treatment with vehicle, SHP099, afatinib or in combination. SHP099 or afatinib alone moderately delayed LK2 tumor growth, whereas combining SHP099 with afatinib had the most significant antitumor effects (FIG. 12E). In line with this, the combination therapy led to the best OS benefit in LK2 tumor bearing mice with a median OS of 33.5 days from treatment initiation (FIG. 12F). By contrast, the vehicle, SHP099 and afatinib treated mice had a median OS of 14, 28 and 19 days, respectively. Additionally, we generated four patient-derived xenografts (PDXs, PDX-1 and 3 are KMT2D mutant; PDX-2 and 4 are Kmt2d WT) from LUSC patient specimens to further assess the responses to SHP099 and afatinib treatment. Likewise, SHP099 or afatinib alone markedly attenuated tumor growth in both KMT2D mutant PDXs (FIGS. 5I and 12G), whereas combining SHP099 with afatinib had the most significant antitumor effects. Notably, the combination treatment led to more than 30% decrease of tumor volume in all treated mice (n=7) in KMT2D mutant PDX-1 (FIG. 5H). By contrast, the Kmt2d WT PDXs were much less sensitive to SHP099 and afatinib treatment (FIGS. 5I and 12H). These findings further support that human LUSC with KMT2D mutation is hypersensitive to the RTK-Ras inhibition.

We next examined whether KMT2D loss would increase the sensitivity to SHP2 and pan-ERBB inhibition in human LUSC. We generated a pair of isogenic cell lines in the Kmt2d WT human LUSC, namely HARA-sgControl and HARA-sgKMT2D (FIG. 5J). HARA-sgControl and HARA-sgKMT2D tumors grew at a similar rate in the mice. Notably, HARA-sgKMT2D tumors responded the best to the SHP099 and afatinib treatment, in comparison to the Kmt2d WT counterparts (FIGS. 5J and 5K), highlighting again that KMT2D loss renders LUSC tumors hypersensitive to the RTK-Ras inhibition in vivo.

In summary, our extensive in vivo therapeutic studies demonstrate that SHP099 or afatinib alone significantly inhibits tumor growth and prolongs survival in multiple murine and human KMT2D-deficient LUSC models and combining SHP099 with afatinib offers superior antitumor efficacy and survival benefits.

Example 9

KMT2D Loss Reprograms the LUSC Epigenetic Landscape in LUSC

KMT2D-mediated H3K4 methylation is a prerequisite for activation of distal enhancers marked by H3K27 acetylation (H3K27ac) (Lai et al., 2017; Lee et al., 2013; Wang et al., 2016). Indeed, KMT2D loss has been associated with decreased H3K27ac at distal enhancers and reduced expression of their associated genes (Lai et al., 2017; Lee et al., 2013; Maitituoheti et al., 2020). To define how KMT2D loss affects gene enhancers in facilitating oncogenesis in LUSC, we performed H3K27ac chromatin immunoprecipitation sequencing (ChIP-seq) in Kmt2d KO and Kmt2d WT cell lines. The resulting H3K27ac sites (or "peaks") were classified into lost, gained and unaffected peaks in Kmt2d KO versus the Kmt2d WT cells (FIGS. 6A and 6B). As expected, the majority of H3K27ac sites (26,835 sites, 76.57%) were not significantly perturbed. Notably, we found 5,301 H3K27ac sites lost (15.11%) and 2,938 gained (8.37%) in Kmt2d KO cells. The finding of more lost sites than gained ones is consistent with previous work, supporting that KMT2D primarily functions as an activator of H3K27ac (Froimchuk et al., 2017).

We then explored the relationship between Kmt2d loss-affected H3K27ac peaks and gene expression changes (FIG. 6C). In particular, we assigned the closest genes to the affected H3K27ac peaks and examined their expression changes in response to Kmt2d loss. The results showed that genes associated with H3K27ac lost sites had significant overlap (n=796) with genes that are downregulated in Kmt2d KO cells (FIGS. 6C-6E). On the other hand, genes associated with H3K27ac gained sites exhibited significant overlap (n=564) with genes that are upregulated in Kmt2d KO cells (FIGS. 6C-6E). These data suggest that KMT2D loss reprograms enhancer activity to affect gene expression in LUSC cells.

Example 10

KMT2D Deletion Suppresses Receptor Tyrosine Phosphatase Expression Potentiating RTK-Ras Signaling Given that KMT2D deficiency is associated with lost H3K27ac sites and reduced gene transcription, we sought to further characterize the alterations in chromatin organization upon Kmt2d loss. We performed the assay of transposase accessible chromatin-sequencing (ATAC-seq) to profile the genome-wide chromatin accessibility in Kmt2d KO and Kmt2d WT cells. Similar to the H3K27ac ChIP-seq data, ATAC-seq analysis revealed that there were 35,883 unaffected sites, 3,721 lost sites, and 3,276 gained sites in Kmt2d KO cells compared to Kmt2d WT cells (FIG. 6F). To define the potential target genes downregulated by Kmt2d loss, we combined RNA-seq downregulated genes, H3K27ac lost sites-associated genes, and ATAC-seq lost sites-associated genes in Kmt2d KO, resulting in 359 high-confidence candidate Kmt2d-target genes (FIG. 6G, Table 3). Gene ontology (GO) analysis of the 359 genes showed marked enrichment in the "Phosphoric ester hydrolase activity" and "Phosphatase activity" molecular functions (FIG. 6H). Most notable among the phosphatase genes were members of receptor-like protein tyrosine phosphatases (RPTP) (FIG. 6I). RPTP family genes are frequently mutated in multiple types of cancers and mainly act as tumor suppressors (Meeusen and Janssens, 2018; Ostman et al., 2006). RPTPs have been reported to directly dephosphorylate ERBB to repress the RTK-Ras signaling (Meeusen and Janssens, 2018; Tonks, 2006). In line with the reduction in gene expression, H3K27ac levels were significantly downregulated at the enhancer regions for Ptprb, Ptprf, Ptprs and Ptpru (FIGS. 7A-7D). Consistently, ATAC-seq analysis revealed that overall chromatin accessibility was also reduced at these regions. We next performed CUT&Tag profiling to examine the alterations of H3K4me1 and H3K4me3, both which are known direct targets of KMT2D (FIGS. 13A-13D). Likewise, H3K4me1 levels were significantly reduced at the enhancer regions for Ptprb, Ptprf, Ptprs and Ptpru, whereas a notable reduction in H3K4me3 signals at promoter regions of Ptprs and Ptpru, to a lesser extent at Ptprb or Ptprf, was observed (FIGS. 7A-7D). Together, these findings highlight KMT2D as an important epigenetic regulator in RPTPs expression.

TABLE 3

Overlapped genes of H3K27ac lost sites-associated genes, ATAC lost sites-associated genes, and RNA-seq downregulated genes Mbtps1
Zfp532
Ogdh
Rnf145
Smad6
Tcf7l1
Map3k14
Gipc1
Inpp5f
Slc30a6
Dhrs3
Man2b1
Chchd6
Zfp750
Mbnl1
Kif26b
Tk1
Nphp3
Tspan12
Mmp15
Smyd2
Marveld3
Tnks
Lipm
Pmaip1
Dhx8
Slc15a4
Gpatch2
Slc24a3
Dnajc11
Rxra
Pink1
Aspscr1
Lpin2
Tmem63a
Igf2r
Elac2
Usp43
Atp8b1
Clip4
Ptprf
Mfsd11
Cdh3
Akap13
Slc6a6
Atp6v1b2
Ube2o
Zfp958
Tns3
Sec14l1
Fam53b
Tm2d2
Galnt2
Thumpd2
Sulf2
Mettl21a
Ndst1
Maml3
Eva1a
Carnmt1
Cyth1
Thra
Pex10
Cnksr3
Stmn1
Irx5
Sh2d4a
Gaa
Thrb
Nt5dc2
Slc27a1
Tpgs2
Thbs1
Tnc
Zbtb7c
Phkb
Ccdc126
Aifm2
Mok
Fzd8

TABLE 3-continued

Overlapped genes of H3K27ac lost sites-associated genes, ATAC lost sites-associated genes, and RNA-seq downregulated genes Fgfr1
Prorsd1
Kazn
Mtus1
Azin2
Flnc
Adgrg1
Fat2
Dsg3
Ephx1
Noct
St3gal2
Btbd3
Arl5b
Tmem14a
Foxo6
Fech
Atp6v1c2
Eya2
Rcn1
Prickle1
Gadd45g
Map2k6
Ankrd6
Sox11
Gab1
Ugt1a6a
Gramd3
Slc25a29
Faap20
Ptpn14
Tram2
Hspg2
Sh3bp2
E130308A19Rik
Plcg2
Klrg2
Adcy3
Fggy
Has3
Eml1
Pik3r1
Syce2
Rassf10
Adamts16
Cdc42ep3
Il15
Csrp2
Fbxo40
Tyro3
Prdm1
Mcc
Rhob
Jun
Vegfc
Ctnnbip1
Sorcs2
Psd3
Ttc39c
Cat
Gpt
Plekhg5
Egr1
Stra6
Pramef12
Synpo
Grhl3
Setbp1
Ass1
Ablim3
Bdh1
Togaram2
Lrig3
Diras2
Pitx1
Aldh3a1
Axin2
Spsb1
Clic5
Kctd1
Nfix
Drc3
Rnls
E130311K13Rik
Tmem265
Kank1
Tbc1d9
Itgb3
Hs3st3b1
Nudt7
Crybg2
Cpm
Lipg
Sorbs2
Il23r
Wwp2
Edar
Socs3
Atp11a
Cavin3
Ago4
Fam171a2
Mab21l3
Tgfb2
E2f2
Cnih3
Fgfr2
Clic3
Zfp948
Plcxd1
Timp3
Pmp22
Nkd2
Afap1l2
Wnt11
Lrrc75b
D7Ertd443e
Calr4
Slc46a2
Lmo1
Lbh
Tfcp2l1
Emx2
Arl4d
Fhod3
Rnf222
Chst11
Btg2
Cercam
Bcl11b
Stpg1
Egr3
Nacad
Prkar1b
Sipa1l2
Chst3
Osr1
Itgb8
Bbox1
Plxdc2
Dsc1
Gfra1
Dysf
Apcdd1
Zfp185
Moxd1
Runx3
Wnt5b
Atp2b4
Mtmr7
Rs1
Zfp536
Ptgfr
Efs

TABLE 3-continued

Overlapped genes of H3K27ac lost sites-associated genes, ATAC lost sites-associated genes, and RNA-seq downregulated genes Sox5
Gsta3
Ptprb
Mylk3
Tmem62
Morn1
Dsc3
Fxyd4
Dact2
Fam110b
Mroh4
Tbc1d30
1190005I06Rik
Smim5
Slc8a1
Kcnj2
Gas6
Cdo1
Bnc2
Adm
Robo2
Zeb1
Hsd17b2
Anpep
Slc1a3
Car12
Kcnk2
Lrguk
Vdr
Cbs
St6galnac2
Spock2
Fbln5
Ucp3
Slc16a9
Cytip
Cers4
Cldn1
Mpped2
Mgat5b
Col9a3
Ophn1
Megf6
Nrep
Rgs17
Eya4
Nos1
Ebf1
Mrc2
Robo1
Bambi
Ptpru
Wnt10b
Slc7a2
Sp8
Asxl3
Spink5
Ntng1
Dsg1c
Tbx15
Fgf16
Mmp2
Trabd2b
Cspg4
Ppp1r3c
Tmod1
Evl
Inhbb
Fam189a2
Dmbt1
Hspb1
Fam180a
Kcnh1
Hhipl1
Fyb
Frmd7
Myh10
Naaladl2
Sspn
Scube3
Capns2
Adamtsl1
Arhgef15
Col4a6
Dact1
Podnl1
Gucy2f
Grm8
Podn
Itga11
Fstl1
Prtg
Dclk1
Tmem108
Cyp4b1
Mia
Dgki
Tenm3
Slc25a18
Gpc6
Plcl2
Bcl11a
Prelp
Mxra7
Adamts3
B3galt2
Sema3d
Slc24a2
Gabrb3
Cntln
Gli2
Ctnnd2
Igf1
Igfbp2
Arhgap24
Gucy1a2
Tlr5
Wnt3a
Uty
Htra4
Eif2s3y
Cacna1c
Postn
Dync1i1
Cntn2

To examine the association between KMT2D and RPTPs in human LUSC samples, we analyzed the expression of KMT2D versus the RPTPs in TCGA LUSC dataset. KMT2D expression was significantly and positively correlated with the expression of PTPRB, PTPRF, PTPRS and PTPRU (FIGS. 7E-H). This data supports that KMT2D loss is associated with downregulation of RPTPs, which are negative regulators of the oncogenic RTK-Ras signaling. To confirm KMT2D regulates RPTPs expression in LUSC, we performed qRT-PCR on Kmt2d KO and Kmt2d WT cells. Consistent with the RNA-seq and epigenetic analysis, Kmt2d loss significantly reduced the expression of Ptprb, Ptprf, Pqifs and Ptpru in Kmt2d KO murine and human LUSC cells (FIGS. 7I, 7J and 13E).

In order to elucidate which specific RPTP(s) might be responsible for the elevated RTK-Ras signaling in LUSC, we knocked down each of the RPTPs (Ptprb, Ptprf, Ptprs or Ptpru) individually in the Kmt2d WT LUSC cells (FIGS. 13F-I). Western blot showed that both shRNA targeting Ptprf led to a robust increase in pEGFR and pERK levels, phenocopying the loss of KMT2D (FIG. 7K). Interestingly, knocking down Ptprb and Ptpru_increased pERK but not pEGFR levels, suggesting that Ptprb and Ptpru might contribute to the activated Ras signaling through other RTKs. Future studies are needed to evaluate whether these RPTPs could function together to regulate RTK-Ras signaling in the development KMT2D-deficient LUSC.

Collectively, our findings indicate that KMT2D loss leads to decreased expression of RPTPs, which in turn activate the oncogenic RTK-Ras signaling to promote tumorigenesis in LUSC. Functional analysis revealed that Ptprf plays an important role in regulating the RTK-Ras (EGRF/ERK) signaling in LUSC oncogenesis.

While the invention has been described through embodiments, routine modifications to the disclosure here will be apparent to those skilled in the art. Such modifications are intended to be within the scope of this disclosure.

What is claimed is:

1. A method for treatment of an individual who has been diagnosed with lung squamous cell carcinoma (LUSC) and wherein a KMT2D loss of function mutation has been identified in a sample of carcinoma cells of the LUSC from the individual prior to treatment, the method of treatment comprising administering to the individual in need of the treatment a combination of inhibitors of RTK-Ras signaling pathway, and wherein said combination comprises afatinib and one of SHP099 or TNO155.

2. The method of claim 1, wherein a combination of SHP099 and afatinib is administered to the individual.

3. The method of claim 1, wherein a combination of TNO155 and afatinib is administered to the individual.

* * * * *